(12) United States Patent
Velcheva et al.

(10) Patent No.: US 9,145,562 B2
(45) Date of Patent: Sep. 29, 2015

(54) VARIEGATION IN PLANTS

(75) Inventors: Margarita Velcheva, Edmonton (CA); John Vidmar, Edmonton (CA); Jurgen Quandt, Edmonton (CA)

(73) Assignee: ALBERTA INNOVATES—TECHNOLOGY FUTURES, Edmonton, Alberta (CA)

( * ) Notice: Subject to any disclaimer, the term of this patent is extended or adjusted under 35 U.S.C. 154(b) by 794 days.

(21) Appl. No.: 12/592,195

(22) Filed: Nov. 20, 2009

(65) Prior Publication Data

US 2011/0126311 A1    May 26, 2011

(51) Int. Cl.
  *C12N 15/82*    (2006.01)
  *C12N 15/113*    (2010.01)

(52) U.S. Cl.
  CPC .......... *C12N 15/8218* (2013.01); *C12N 15/825* (2013.01); *C12N 15/8212* (2013.01)

(58) Field of Classification Search
  USPC ....................................................... 800/285
  See application file for complete search history.

(56) References Cited

U.S. PATENT DOCUMENTS

| | | | |
|---|---|---|---|
| 5,639,952 | A | 6/1997 | Quail et al. |
| 5,656,496 | A | 8/1997 | Quail et al. |
| 5,750,385 | A | 5/1998 | Shewmaker et al. |
| 5,824,872 | A | 10/1998 | Miki et al. |
| 6,479,260 | B1 | 11/2002 | Takayama et al. |
| 6,784,340 | B1 | 8/2004 | Aoyama et al. |

FOREIGN PATENT DOCUMENTS

| | | |
|---|---|---|
| AU | 765413 | 10/2000 |
| CA | 2328139 | 9/2000 |
| WO | WO 93/18169 | 9/1993 |
| WO | WO 98/00533 | 1/1998 |
| WO | WO 99/67389 | 12/1999 |
| WO | WO 01/18211 A1 | 3/2001 |
| WO | WO 02/36786 A2 | 5/2002 |
| WO | WO 02/50291 A1 | 6/2002 |
| WO | WO 02/077248 A1 | 10/2002 |
| WO | WO 2005/085449 A2 | 9/2005 |
| WO | WO 2006/066193 A2 | 6/2006 |

OTHER PUBLICATIONS

Caddick et al. An ethaniol inducible gene switch for plants used to manipulate carbon metabolism (1998) Nat. Biotechnol. 16: 177-180.*
Hanania et al. Silencing of chaperonin 21, that was differentially expressed in infloresence of seedless and seeded grapes, promoted seed abortion in tobacco and tomato fruits (2007) Transgen. Res. 16: 515-525.*
Liu et al. Virus-induced gene silencing in tomato (2002) Plant J. 31: 777-786.*
Smith et al. An SNF2 protein associated with nuclear RNA silencing and the spread of a silencing signal between cells in *Arabidopsis* (2007) 19: 1507-1521.*
Zabaleta et al. Antisense expression of chaperonin 60B in transgenic tobacco plants leads to abnormal phenotypes and altered distribution of photoassimilates (1994) 6:425-432.*
NCBI GenBank Accession No. AF428366.*
Hanania et al (2007) Transgen. Res. 16: 515-525.*
GenBank Accession No. NM_001247494.1 (2011).*
GenBank Accession No. AY680699.1; Hanania et al., (2004).*
Stout et al. (1940) Proc. Amer. Soc. for Hort. Sci. 37: 627-629.*
Rathjen et al. (1992) Plant Physiol. 99: 1619-1625.*
Emershad et al. (1994) Plant Cell Rep. 14: 6-12.*
Min and Kamiya, GenBank Accession No. AF233745.1, 2000.*
Abe et al., "Utilization of heavy ion beam as a mutagen in plants," *The 14th Symposium on Accelerator Science and Technology* (2003) Tsukuba, Japan.
Aluru et al., "*Arabidopsis* variegation mutants: new insights into chloroplast biogenesis," *Journal of Experimental Botany* (2006) 57 (9): 1871-1881.
Aluru et al., "The *Arabidopsis* immutans mutation affects plastid differentiation and the morphogenesis of white and green sectors in variegated plants," *Plant Physiology* (2001) 127: 67-77.
Aoyama et al., "A glucocorticoid-mediated transcriptional induction system in transgenic plants," *The Plant Journal* (1997) 11 (3): 605-612.
Apuya et al., "The *Arabidopsis* embryo mutant schlepperless has a defect in the Chaperonin-60α gene," *Plant Physiology* (2001) 126: 717-730.
Baneyx et al., "Spinach chloroplast cpn21 co-chaperonin possesses two functional domains fused together in a toroidal structure and exhibits nucleotide-dependent binding to plastid chaperonin 60," *The Journal of Biological Chemistry* (1995) 270 (18): 10695-10702.
Beilmann et al., "Activation of a truncated PR-1 promoter by endogenous enhancers in transgenic plants," *Plant Molecular Biology* (1992) 18: 65-78.
Bertsch et al., "Identification, characterization, and DNA sequence of a functional "double" groES-like chaperonin from chloroplasts of higher plants," *Proc. Natl. Acad. Sci.* (1992) 89: 8696-8700.
Brandstatter et al., "Two genes with similarity to bacterial response regulators are rapidly and specifically induced by cytokinin in *Arabidopsis*," *The Plant Cell* (1998) 10: 1009-1019.
Büttner et al., "AtSTP3, a green leaf-specific, low affinity monosaccharide—H+ symporter of *Arabidopsis thaliana*," *Plant, Cell and Environment* (2000) 23: 175-184.
Caddick et al., "An ethanol inducible gene switch for plants used to manipulate carbon metabolism," *Nature Biotechnology* (1998) 16: 177-180.
Canevascini et al., "Tissue-specific expression and promoter analysis of the tobacco ltp1 gene," *Plant Physiol* (1996) 112: 513-524.
Chen et al., "Identification of genes subject to positive selection in uropathogenic strains of *Escherichia coli*: A comparative genomics approach," *PNAS* (2006) 103: 5977-5982.

(Continued)

*Primary Examiner* — Russell Kallis
*Assistant Examiner* — Steven Bernacki
(74) *Attorney, Agent, or Firm* — Merchant & Gould P.C.

(57) ABSTRACT

A variegated plant comprising a nucleic acid operatively linked to a regulatory region, the nucleic acid disrupts the expression of Cpn21. The nucleic acid is typically an antisense Cpn21 and the regulatory region may be an inducible regulatory region, a tissue specific regulatory region, or a developmental regulatory region.

15 Claims, 29 Drawing Sheets
(6 of 29 Drawing Sheet(s) Filed in Color)

(56) References Cited

OTHER PUBLICATIONS

Cornejo et al., "Activity of a maize ubiquitin promoter in transgenic mice," *Plant Molecular Biology* (1993) 23: 567-581.
Emlyn-Jones et al., "RbcX can function as a rubisco Chaperonin, but is non-essential in *Synechococcus* PCC7942," *Plant Cell Physiol.* (2006) 47 (12): 1630-1640.
Fromm et al., "An octopine synthase enhance element directs tissue-specific expression and binds ASF-1, a factor from tobacco nuclear extracts," *The Plant Cell* (1989) 1: 977-984.
Garoosi et al., "Characterization of the ethanol-inducible alc gene expression system in tomato," *Journal of Experimental Botany* (2005) 56 (416): 1635-1642.
Gatz et al,. "Promoters that respond to chemical inducers," *Trends in Plant Sci.* (1998) 3: 352-358.
Gatz, C., "Chemical control of gene expression," *Annu. Rev. Plant Physiol. Plant Mol. Biol.* (1997) 48: 89-108.
Giri et al., "Distribution of RuBisCO genotypes along a redox gradient in Mono Lake, California," *Applied and Environmental Microbiology* (2004) 70 (6): 3443-3448.
Guerche et al., "Differential expression of the *Arabidopsis* 2S Albumin genes and the effect of increasing gene family size," *The Plant Cell* (1990) 2: 469-478.
Hanania et al., "Silencing of chaperonin 21, that was differently expressed in inflorescence of seedless grapes and seeded grapes, promoted seed abortion in tobacco and tomato fruits," *Transgenic Res.* (2007) 16: 515-525.
Hellens et al., "A guide to *Agrobacterium* binary Ti vectors," *Trends in Plant Science* (2000) 5 (10): 446-451.
Hellens et al., "pGreen: a versatile and flexible binary Ti vector for *Agrobacterium*-mediated plant transformation," *Plant Molecular Biology* (2000) 42: 819-832.
Hill et al., "cpnDB: A chaperonin sequence database," *Genome Research* (2004) 14:1669-1675.
Hirohashi et al., "cDNA sequence and overexpression of chloroplast chaperonin 21 from *Arabidopsis thaliana*," *Biochimica et Biophysica Acta* (1999) 1429: 512-515.
Höfgen et al., "A visible marker for antisense mRNA with a glutamate-1-semialdehyde aminotransferase antisense gene," *Proc. Natl. Acad. Sci. USA* (1994) 91: 1726-1730.
Holtorf et al., "Comparison of different constitutive and inducible promoters for the overexpression of transgenes in *Arabidopsis thaliana*," *Plant Molecular Biology* (1995) 29: 637-646.
Husebye et al., "Guard cell-and phloem idioblast specific expression of thioglucoside glucohydrolase 1 (myrosinase) in *Arabidopsis*," *Plant Physiology* (2002) 128: 1-9.
Imlau et al., "Cell-to-cell and long-distance trafficking of the green fluorescent protein in the phloem and symplastic unloading of the protein into sink tissues," *The Plant Cell* (1999) 11: 309-322.
Ishikawa et al., "The transposon Tip100 from the common morning glory is an autonomous element that can transpose in tobacco plants," *Mol. Genet Geonomics* (2002) 266: 732-739.
Itoh et al., "Excision of transposable elements from the chalcone isomerase and dihydroflavonol 4-reductase genes may contribute to the variegation of the yellow-flavored carnation (*Dianthus caryophyllus*)," *Plant Cell Physiol.* (2002) 43 (5): 578-585.
Kakimoto et al., "CKI1, a histidine kinase homolog implicated in cytokinin signal transduction," *Science* (1996) 274:982-985.
Karimi et al., "Gateway™ vectors for *Agrobacterium*-mediated plant transformation," *Trends in Plant Science* (2002) 7 (5): 193-195.
Koch et al., "Molecular systematics of the brassicaceae: Evidence from coding plastidic MATK and nuclear CHS sequences," *American Journal of Botany* (2001) 88 (2): 534-544.
Kontár, K., "Dissertation Summary: Genetic analysis of a *Medicago truncatula* mutation causing variegated leaf phenotype," *Acta Biologica Szegediensis* (2004) 48: 59.
Lam et al., "Tetramer of a 21-base pair synthetic element confers seed expression and transcriptional enhancement in response to water stress and abscisic acid," *The Journal of Biological Chemistry* (1991) 266 (26): 17131-17135.

Mandel et al., "Definition of constitutive gene expression in plants: the translation initiation factor 4A gene as a model," *Plant Molecular Biology* (1995) 29: 995-1004.
Matsuki et al., "Tissue-specific expression of the rolC promoter of the Ri plasmid in transgenic rice plants," *Mol Gen Genet* (1989) 220: 12-16.
Michel et al., "Analysis of a desiccation and ABA-responsive promoter isolated from the resurrection plant *Craterostigma plantagineum*," *The Plant Journal* (1993) 4 (1): 29-40.
Odell et al., "Identification of DNA sequences required for activity of the cauliflower mosaic virus 35S promoter," *Nature* (1985) 313: 810-812.
Panguluri et al., "Isolation and characterization of a green tissue-specific promoter from pigeonpea [*Cajanus cajan* (L.) Millsp.]," *Indian Journal of Experimental Biology* (2005) 43: 369-372.
Plesch et al., "Cloning of regulatory sequences mediating guard-cell-specific gene expression," *Gene* (2000) 249: 83-89.
Renckens et al., "*Petunia* plants escape from negative selection against a transgene by silencing the foreign DNS via methylation," *Mol Gen Genet* (1992) 233: 53-64.
Roberts et al., "The alc-GR system. A modified alc gene switch designed for use in plant tissue culture," *Plant Physiology* (2005) 138: 1259-1267.
Roslan et al., "Characterization of the ethanol-inducible alc gene-expression system in *Arabidopsis thaliana*," *The Plant Journal* (2001) 28 (2): 225-235.
Sablowski et al., "A homolog of No Apical Meristem is an immediate target of the floral homeotic genes APETALA3-PISTILLATA," *Cell* (1998) 92: 93-103.
Sakamoto et al., "The VAR1 locus of *Arabidopsis* encodes a chloroplastic FtsH and is responsible for leaf varigation in the mutant alleles," *Genes to Cells* (2002) 7: 769-780.
Salter et al., "Characterisation of the ethanol-inducible alc gene expression system for transgenic plants," *The Plant Journal* (1998) 16 (1): 127-132.
Sjögren et al., "Inactivation of the c1pC1 gene encoding a chloroplast Hsp100 molecular chaperone causes growth retardation, leaf chlorosis, lower photosynthetic activity, and a specific reduction in photosystem content," *Plant Phsyiology* (2004) : 1-13.
Stockhaus et al., "Analysis of cis-active sequences involved in the leaf-specific expression of a potato gene in transgenic plants," *Proc. Natl. Acad. Sci.* (1987) 84: 7943-7947.
Ulmasov et al., "Aux/IAA proteins repress expression of reporter genes containing natural and highly active synthetic auxin response elements," *The Plant Cell* (1997) 9: 1963-1971.
Wang et al., "Tobacco VDL gene encodes a plastid DEAD box RNA helicase and is involved in chloroplast differentiation and plant morphogenesis," *The Plant Cell* (2000) 12: 2129-2142.
Wielopolska et al., "A high-throughput inducible RNAi vector for plants " *Plant Biotechnology Journal* (2005) 3: 583-590.
Xu et al., "Rice triosephosphate isomerase gene 5' sequence directs β-glucuronidase activity in transgenic tobacco but requires an intron for expression in rice," *Plant Physiol.* (1994) 106: 459-467.
Zabaleta et al., "Antisense expression of chaperonin 60β in transgenic tobacco plants leads to abnormal phenotypes and altered distribution of phtoassimilates," *The Plant Journal* (1994) 6 (3): 425-432.
Zhang et al., "Analysis of rice Act1 5' region activity in transgenic rice plants," *The Plant Cell* (1991) 3: 1155-1165.
Zuo et al., "An estrogen receptor-based transactivator XVE mediates highly inducible gene expression in transgenic plants," *The Plant Journal* (2000) 24 (2): 265-273.
Form PCT/ISA/237 for corresponding International Application No. PCT/CA2010/001853.
Form PCT/ISA/210 for corresponding International Application No. PCT/CA2010/001853.
Form PCT/ISA/220 for corresponding International Application No. PCT/CA2010/001853.

\* cited by examiner

Figure 8A

SEQ ID NO: 1 gi|16226910|gb|AF428366.1|AF428366 Arabidopsis thaliana AT5g20720/T1M15_120 mRNA, complete cds AACTCTCTCTACTGCAATTTTTAGGGTTTTATCCTCCGAAAGTCTCAACCTTTTTCTTATCCT
CAACAAGGAGAAATGGCGGCGACTCAACTTACAGCGTCACCAGTGACTATGTCAGCAAGGAG
CTTAGCCTCGCTGGATGGTCTCAGAGCTTCGAGTGTCAAGTTTTCATCTTTGAAACCAGGGAC
CCTTAGACAGAGCCAGTTCCGTCGTTTGGTTGTCAAAGCTGCTTCTGTTGTTGCCCCTAAGTAT
ACTTCAATTAAGCCATTGGGAGATCGAGTTTTGGTGAAGATCAAGGAGGCAGAGGAGAAGAC
TTTAGGTGGTATCTTACTTCCATCCACTGCTCAATCAAAACCTCAAGGAGGTGAAGTCGTTGC
CGTGGGTGAAGGAAGAACTATTGGGAAGAACAAAATTGATATCACTGTCCCTACTGGAGCAC
AAATTATCTACTCCAAATACGCAGGAACTGAGGTGGAGTTCAATGATGTGAAGCATCTTATCC
TCAAGGAAGATGATATTGTTGGCATTCTTGAGACAGAGGACATCAAAGATCTCAAACCTTTGA
ATGACCGAGTCTTTATTAAGGTTGCTGAGGCGGAGGAGAAAACAGCTGGAGGGTTGTTGTTA
ACCGAGACTACCAAAGAGAAGCCTTCTATTGGCACGGTGATAGCAGTTGGACCGGGTTCCCTA
GACGAGGAAGGTAAAATTACGCCTCTACCAGTATCAACCGGAAGCACAGTACTTTACTCCAA
GTATGCTGGTAACGACTTCAAGGGCAAAGATGGTTCCAACTACATTGCCCTCAGAGCTTCAGA
TGTGATGGCTATACTTTCTTAGTTATGTTATATCTTTGTAATCTGCAACTTGTATCCCAATTGTG
GAAATTTTTTCCGTAAACGGCCTGAGCATAATCTGGAATAAAGACTTGAGTTTGAAAATGTGA
TTTTATTGCC

Figure 8B
SEQ ID NO: 4
Cpn21 Antisense 35S

TGACCATGGTAGATCTGACTAGTCCAGATTATGCTCAGGCCGTTTACGGAAAAAATTTCCACA
ATTGGGATACAAGTTGCAGATTACAAAGATATAACATAACTAAGAAAGTATAGCCATCACAT
CTGAAGCTCTGAGGGCAATGTAGTTGGAACCATCTTTGCCCTTGAAGTCGTTACCAGCATACT
TGGAGTAAAGTACTGTGCTTCCGGTTGATACTGGTAGAGGCGTAATTTTACCTTCCTCGTCTAG
GGAACCCGGTCCAACTGCTATCACCGTGCCAATAGAAGGCTTCTCTTTGGTAGTCTCGGTTAA
CAACAACCCTCCAGCTGTTTTCTCCTCCGCCTCAGCAACCTTAATAAAGACTCGGTCATTCAAA
GGTTTGAGATCTTTGATGTCCTCTGTCTCAAGAATGCCAACAATATCATCTTCCTTGAGGATAA
GATGCTTCACATCATTGAACTCCACCTCAGTTCCTGCGTATTTGGAGTAGATAATTTGTGCTCC
AGTAGGGACAGTGATATCAATTTTGTTCTTCCCAATAGTTCTTCCTTCACCCACGGCAACGACT
TCACCTCCTTGAGGTTTTGATTGAGCAGTGGATGGAAGTAAGATACCACCTAAAGTCTTCTCC
TCTGCCTCCTTGATCTTCACCAAAACTCGATCTCCCAATGGCTTAATTGAAGTATACTTAGGGG
CAACAACAGAAGCAGCTTTGACAACCAAACGACGGAACTGGCTCTGTCTAAGGGTCCCTGGT
TTCAAAGATGAAAACTTGACACTCGAAGCTCTGAGACCATCCAGCGAGGCTAAGCTCCTTGCT
GACATAGTCACTGGTGACGCTGTAAGTTGAGTCGCCGCCATTTCACGTGTGAATTGGTGACCA
GCTCGAATTTCCCCGATCGTTCAAACATTTGGCAATAAAGTTTCTTAAGATTGAATCCTGTTGC
CGGTCTTGCGATGATTATCATATAATTTCTGTTGAATTACGTTAAGCATGTAATAATTAACATG
TAATGCATGACGTTATTTATGAGATGGGTTTTTATGATTAGAGTCCCGCAATTATACATTTAAT
ACGCGATAGAAAACAAAATATAGCGCGCAAACTAGGATAAATTATCGCGCGCGGTGTCATCT
ATGTTACTAGATCGGGAATTAAACTATCAGTGTTTGACAGGATATATTGGCGGGTAAACCTAA
GAGAAAAGAGCGTTTATTAGAATAACGGATATTTAAAAGGGCGTGAAAAGGTTTATCCGTTC
GTCCATTTGTATGTGCATGCCAACCACAGGGTTCCCCTCGGGATCAAAGTACTTTGATCCAAC
CCCTCCGCTGCTATAGTGCAGTCGGCTTCTGACGTTCAGTGCAGCCGTCTTCTGAAAACGACA
TGTCGCACAAGTCCTAAGTTACGCGACAGGCTGCCGCCCTGCCCTTTTCCTGGCGTTTTCTTGT
CGCGTGTTTTAGTCGCATAAAGTAGAATACTTGCGACTAGAACCGGAGACATTACGCCATGAA
CAAGAGCGCCGCCGCTGGCCTGCTGGGCTATGCCCGCGTCAGCACCGACGACCAGGACTTGA
CCAACCAACGGGCCGAACTGCACGCGGCCGGCTGCACCAAGCTGTTTTCCGAGAAGATCACC
GGCACCAGGCGCGACCGCCCGGAGCTGGCCAGGATGCTTGACCACCTACGCCCTGGCGACGT
TGTGACAGTGACCAGGCTAGACCGCCTGGCCCGCAGCACCCGCGACCTACTGGACATTGCCG
AGCGCATCCAGGAGGCCGGCGCGGGCCTGCGTAGCCTGGCAGAGCCGTGGGCCGACACCACC
ACGCCGGCCGGCCGCATGGTGTTGACCGTGTTCGCCGGCATTGCCGAGTTCGAGCGTTCCCTA
ATCATCGACCGCACCCGGAGCGGGCGCGAGGCCGCCAAGGCCCGAGGCGTGAAGTTTGGCCC
CCGCCCTACCCTCACCCCGGCACAGATCGCGCACGCCCGCGAGCTGATCGACCAGGAAGGCC
GCACCGTGAAAGAGGCGGCTGCACTGCTTGGCGTGCATCGCTCGACCCTGTACCGCGCACTTG
AGCGCAGCGAGGAAGTGACGCCCACCGAGGCCAGGCGGCGCGGTGCCTTCCGTGAGGACGCA
TTGACCGAGGCCGACGCCCTGGCGGCCGCCGAGAATGAACGCCAAGAGGAACAAGCATGAA
ACCGCACCAGGACGGCCAGGACGAACCGTTTTTCATTACCGAAGAGATCGAGGCGGAGATGA
TCGCGGCCGGGTACGTGTTCGAGCCGCCCGCGCACGTCTCAACCGTGCGGCTGCATGAAATCC
TGGCCGGTTTGTCTGATGCCAAGCTGGCGGCCTGGCCGGCCAGCTTGGCCGCTGAAGAAACCG
AGCGCCGCCGTCTAAAAAGGTGATGTGTATTTGAGTAAAACAGCTTGCGTCATGCGGTCGCTG
CGTATATGATGCGATGAGTAAATAAACAAATACGCAAGGGGAACGCATGAAGGTTATCGCTG
TACTTAACCAGAAAGGCGGGTCAGGCAAGACGACCATCGCAACCCATCTAGCCCGCGCCCTG
CAACTCGCCGGGGCCGATGTTCTGTTAGTCGATTCCGATCCCCAGGGCAGTGCCCGCGATTGG
GCGGCCGTGCGGAAGATCAACCGCTAACCGTTGTCGGCATCGACCGCCCGACGATTGACCG
CGACGTGAAGGCCATCGGCCGGCGCGACTTCGTAGTGATCGACGGAGCGCCCCAGGCGGCGG
ACTTGGCTGTGTCCGCGATCAAGGCAGCCGACTTCGTGCTGATTCCGGTGCAGCCAAGCCCTT
ACGACATATGGGCCACCGCCGACCTGGTGGAGCTGGTTAAGCAGCGCATTGAGGTCACGGAT
GGAAGGCTACAAGCGGCCTTTGTCGTGTCGCGGGCGATCAAAGGCACGCGCATCGGCGGTGA
GGTTGCCGAGGCGCTGGCCGGGTACGAGCTGCCCATTCTTGAGTCCCGTATCACGCAGCGCGT
GAGCTACCCAGGCACTGCCGCCGCCGGCACAACCGTTCTTGAATCAGAACCCGAGGGCGACG
CTGCCCGCGAGGTCCAGGCGCTGGCCGCTGAAATTAAATCAAAACTCATTTGAGTTAATGAGG
TAAAGAGAAAATGAGCAAAAGCACAAACACGCTAAGTGCCGGCCGTCCGAGCGCACGCAGC
AGCAAGGCTGCAACGTTGGCCAGCCTGGCAGACACGCCAGCCATGAAGCGGGTCAACTTTCA

Figure 8B continued

```
GTTGCCGGCGGAGGATCACACCAAGCTGAAGATGTACGCGGTACGCCAAGGCAAGACCATTA
CCGAGCTGCTATCTGAATACATCGCGCAGCTACCAGAGTAAATGAGCAAATGAATAAATGAG
TAGATGAATTTTAGCGGCTAAAGGAGGCGGCATGGAAAATCAAGAACAACCAGGCACCGACG
CCGTGGAATGCCCCATGTGTGGAGGAACGGGCGGTTGGCCAGGCGTAAGCGGCTGGGTTGTC
TGCCGGCCCTGCAATGGCACTGGAACCCCCAAGCCCGAGGAATCGGCGTGACGGTCGCAAAC
CATCCGGCCCGGTACAAATCGGCGCGGCGCTGGGTGATGACCTGGTGGAGAAGTTGAAGGCC
GCGCAGGCCGCCCAGCGGCAACGCATCGAGGCAGAAGCACGCCCCGGTGAATCGTGGCAAGC
GGCCGCTGATCGAATCCGCAAAGAATCCCGGCAACCGCCGGCAGCCGGTGCGCCGTCGATTA
GGAAGCCGCCCAAGGGCGACGAGCAACCAGATTTTTTCGTTCCGATGCTCTATGACGTGGGCA
CCCGCGATAGTCGCAGCATCATGGACGTGGCCGTTTCCGTCTGTCGAAGCGTGACCGACGAG
CTGGCGAGGTGATCCGCTACGAGCTTCCAGACGGGCACGTAGAGGTTTCCGCAGGGCCGGCC
GGCATGGCCAGTGTGTGGGATTACGACCTGGTACTGATGGCGGTTTCCCATCTAACCGAATCC
ATGAACCGATACCGGGAAGGGAAGGGAGACAAGCCCGGCCGCGTGTTCCGTCCACACGTTGC
GGACGTACTCAAGTTCTGCCGGCGAGCCGATGGCGGAAAGCAGAAAGACGACCTGGTAGAAA
CCTGCATTCGGTTAAACACCACGCACGTTGCCATGCAGCGTACGAAGAAGGCCAAGAACGGC
CGCCTGGTGACGGTATCCGAGGGTGAAGCCTTGATTAGCCGCTACAAGATCGTAAAGAGCGA
AACCGGGCGGCCGGAGTACATCGAGATCGAGCTAGCTGATTGGATGTACCGCGAGATCACAG
AAGGCAAGAACCCGGACGTGCTGACGGTTCACCCCGATTACTTTTTGATCGATCCCGGCATCG
GCCGTTTTCTCTACCGCCTGGCACGCCGCGCCGCAGGCAAGGCAGAAGCCAGATGGTTGTTCA
 AGACGATCTACGAACGCAGTGGCAGCGCCGGAGAGTTCAAGAAGTTCTGTTTCACCGTGCGC
AAGCTGATCGGGTCAAATGACCTGCCGGAGTACGATTTGAAGGAGGAGGCGGGGCAGGCTGG
CCCGATCCTAGTCATGCGCTACCGCAACCTGATCGAGGGCGAAGCATCCGCCGGTTCCTAATG
TACGGAGCAGATGCTAGGGCAAATTGCCCTAGCAGGGGAAAAAGGTCGAAAAGGTCTCTTTC
 CTGTGGATAGCACGTACATTGGGAACCCAAAGCCGTACATTGGGAACCGGAACCCGTACATT
GGGAACCCAAAGCCGTACATTGGGAACCGGTCACACATGTAAGTGACTGATATAAAAGAGAA
AAAAGGCGATTTTTCCGCCTAAAACTCTTTAAAACTTATTAAAACTCTTAAAACCCGCCTGGC
CTGTGCATAACTGTCTGGCCAGCGCACAGCCGAAGAGCTGCAAAAAGCGCCTACCCTTCGGTC
GCTGCGCTCCCTACGCCCCGCCGCTTCGCGTCGGCCTATCGCGGCCGCTGGCCGCTCAAAAAT
GGCTGGCCTACGGCCAGGCAATCTACCAGGGCGCGGACAAGCCGCGCCGTCGCCACTCGACC
GCCGGCGCCCACATCAAGGCACCCTGCCTCGCGCGTTTCGGTGATGACGGTGAAAACCTCTGA
CACATGCAGCTCCCGGAGACGGTCACAGCTTGTCTGTAAGCGGATGCCGGGAGCAGACAAGC
CCGTCAGGGCGCGTCAGCGGGTGTTGGCGGGTGTCGGGGCGCAGCCATGACCCAGTCACGTA
GCGATAGCGGAGTGTATACTGGCTTAACTATGCGGCATCAGAGCAGATTGTACTGAGAGTGC
ACCATATGCGGTGTGAAATACCGCACAGATGCGTAAGGAGAAAATACCGCATCAGGCGCTCT
TCCGCTTCCTCGCTCACTGACTCGCTGCGCTCGGTCGTTCGGCTGCGGCGAGCGGTATCAGCTC
ACTCAAAGGCGGTAATACGGTTATCCACAGAATCAGGGGATAACGCAGGAAAGAACATGTGA
GCAAAAGGCCAGCAAAAGGCCAGGAACCGTAAAAAGGCCGCGTTGCTGGCGTTTTTCCATAG
GCTCCGCCCCCTGACGAGCATCACAAAAATCGACGCTCAAGTCAGAGGTGGCGAAACCCGA
CAGGACTATAAAGATACCAGGCGTTTCCCCCTGGAAGCTCCCTCGTGCGCTCTCCTGTTCCGA
CCCTGCCGCTTACCGGATACCTGTCCGCCTTTCTCCCTTCGGGAAGCGTGGCGCTTTCTCATAG
CTCACGCTGTAGGTATCTCAGTTCGGTGTAGGTCGTTCGCTCCAAGCTGGGCTGTGTGCACGA
ACCCCCCGTTCAGCCCGACCGCTGCGCCTTATCCGGTAACTATCGTCTTGAGTCCAACCCGGT
AAGACACGACTTATCGCCACTGGCAGCAGCCACTGGTAACAGGATTAGCAGAGCGAGGTATG
TAGGCGGTGCTACAGAGTTCTTGAAGTGGTGGCCTAACTACGGCTACACTAGAAGGACAGTAT
TTGGTATCTGCGCTCTGCTGAAGCCAGTTACCTTCGGAAAAGAGTTGGTAGCTCTTGATCCG
GCAAACAAACCACCGCTGGTAGCGGTGGTTTTTTGTTTGCAAGCAGCAGATTACGCGCAGAA
AAAAAGGATCTCAAGAAGATCCTTTGATCTTTTCTACGGGGTCTGACGCTCAGTGGAACGAAA
ACTCACGTTAAGGGATTTTGGTCATGCATTCTAGGTACTAAAACAATTCATCCAGTAAAATAT
AATATTTTATTTTCTCCCAATCAGGCTTGATCCCCAGTAAGTCAAAAAATAGCTCGACATACTG
TTCTTCCCCGATATCCTCCCTGATCGACCGGACGCAGAAGGCAATGTCATACCACTTGTCCGC
CCTGCCGCTTCTCCCAAGATCAATAAAGCCACTTACTTTGCCATCTTTCACAAAGATGTTGCTG
TCTCCCAGGTCGCCGTGGGAAAAGACAAGTTCCTCTTCGGGCTTTTCCGTCTTTAAAAAATCAT
ACAGCTCGCGCGGATCTTTAAATGGAGTGTCTTCTTCCCAGTTTTCGCAATCCACATCGGCCAG
 ATCGTTATTCAGTAAGTAATCCAATTCGGCTAAGCGGCTGTCTAAGCTATTCGTATAGGGACA
```

Figure 8B cont'd

```
ATCCGATATGTCGATGGAGTGAAAGAGCCTGATGCACTCCGCATACAGCTCGATAATCTTTTC
AGGGCTTTGTTCATCTTCATACTCTTCCGAGCAAAGGACGCCATCGGCCTCACTCATGAGCAG
ATTGCTCCAGCCATCATGCCGTTCAAAGTGCAGGACCTTTGGAACAGGCAGCTTTCCTTCCAG
CCATAGCATCATGTCCTTTTCCCGTTCCACATCATAGGTGGTCCCTTTATACCGGCTGTCCGTC
ATTTTTAAATATAGGTTTTCATTTTCTCCCACCAGCTTATATACCTTAGCAGGAGACATTCCTT
CCGTATCTTTTACGCAGCGGTATTTTTCGATCAGTTTTTTCAATTCCGGTGATATTCTCATTTTA
GCCATTTATTATTTCCTTCCTCTTTTCTACAGTATTTAAAGATACCCCAAGAAGCTAATTATAA
CAAGACGAACTCCAATTCACTGTTCCTTGCATTCTAAAACCTTAAATACCAGAAAACAGCTTT
TTCAAAGTTGTTTTCAAAGTTGGCGTATAACATAGTATCGACGGAGCCGATTTTGAAACCGCG
GTGATCACAGGCAGCAACGCTCTGTCATCGTTACAATCAACATGCTACCCTCCGCGAGATCAT
CCGTGTTTCAAACCCGGCAGCTTAGTTGCCGTTCTTCCGAATAGCATCGGTAACATGAGCAAA
GTCTGCCGCCTTACAACGGCTCTCCCGCTGACGCCGTCCCGGACTGATGGGCTGCCTGTATCG
AGTGGTGATTTTGTGCCGAGCTGCCGGTCGGGGAGCTGTTGGCTGGCTGGTGGCAGGATATAT
TGTGGTGTAAACAAATTGACGCTTAGACAACTTAATAACACATTGCGGACGTTTTTAATGTAC
TGAATTAACGCCGAATTAATTCGGGGGATCTGGATTTTAGTACTGGATTTTGGTTTTAGGAATT
AGAAATTTTATTGATAGAAGTATTTTACAAATACAAATACATACTAAGGGTTTCTTATATGCTC
AACACATGAGCGAAACCCTATAGGAACCCTAATTCCCTTATCTGGGAACTACTCACACATTAT
TATGGAGAAACTCGAGCTTGTCGATCGACAGATCCGGTCGGCATCTACTCTATTTCTTTGCCCT
CGGACGAGTGCTGGGGCGTCGGTTTCCACTATCGGCGAGTACTTCTACACAGCCATCGGTCCA
GACGGCCGCGCTTCTGCGGGCGATTTGTGTACGCCCGACAGTCCCGGCTCCGGATCGGACGAT
TGCGTCGCATCGACCCTGCGCCCAAGCTGCATCATCGAAATTGCCGTCAACCAAGCTCTGATA
GAGTTGGTCAAGACCAATGCGGAGCATATACGCCCGGAGTCGTGGCGATCCTGCAAGCTCCG
GATGCCTCCGCTCGAAGTAGCGCGTCTGCTGCTCCATACAAGCCAACCACGGCCTCCAGAAGA
AGATGTTGGCGACCTCGTATTGGGAATCCCCGAACATCGCCTCGCTCCAGTCAATGACCGCTG
TTATGCGGCCATTGTCCGTCAGGACATTGTTGGAGCCGAAATCCGCGTGCACGAGGTGCCGGA
CTTCGGGGCAGTCCTCGGCCCAAAGCATCAGCTCATCGAGAGCCTGCGCGACGGACGCACTG
ACGGTGTCGTCCATCACAGTTTGCCAGTGATACACATGGGGATCAGCAATCGCGCATATGAAA
TCACGCCATGTAGTGTATTGACCGATTCCTTGCGGTCCGAATGGGCCGAACCCGCTCGTCTGG
CTAAGATCGGCCGCAGCGATCGCATCCATAGCCTCCGCGACCGGTTGTAGAACAGCGGGCAG
TTCGGTTTCAGGCAGGTCTTGCAACGTGACACCCTGTGCACGGCGGGAGATGCAATAGGTCAG
GCTCTCGCTAAACTCCCCAATGTCAAGCACTTCCGGAATCGGGAGCGCGGCCGATGCAAAGTG
CCGATAAACATAACGATCTTTGTAGAAACCATCGGCGCAGCTATTTACCCGCAGGACATATCC
ACGCCCTCCTACATCGAAGCTGAAAGCACGAGATTCTTCGCCCTCCGAGAGCTGCATCAGGTC
GGAGACGCTGTCGAACTTTTCGATCAGAAACTTCTCGACAGACGTCGCGGTGAGTTCAGGCTT
TTTCATATCTCATTGCCCCCGGGATCTGCGAAAGCTCGAGAGAGATAGATTTGTAGAGAGAG
ACTGGTGATTTCAGCGTGTCCTCTCCAAATGAAATGAACTTCCTTATATAGAGGAAGGTCTTG
CGAAGGATAGTGGGATTGTGCGTCATCCCTTACGTCAGTGGAGATATCACATCAATCCACTTG
CTTTGAAGACGTGGTTGGAACGTCTTCTTTTTCCACGATGCTCCTCGTGGGTGGGGTCCATCT
TTGGGACCACTGTCGGCAGAGGCATCTTGAACGATAGCCTTTCCTTTATCGCAATGATGGCAT
TTGTAGGTGCCACCTTCCTTTTCTACTGTCCTTTTGATGAAGTGACAGATAGCTGGGCAATGGA
ATCCGAGGAGGTTTCCCGATATTACCCTTTGTTGAAAAGTCTCAATAGCCCTTTGGTCTTCTGA
GACTGTATCTTTGATATTCTTGGAGTAGACGAGAGTGTCGTGCTCCACCATGTTATCACATCAA
TCCACTTGCTTTGAAGACGTGGTTGGAACGTCTTCTTTTTCCACGATGCTCCTCGTGGGTGGGG
GTCCATCTTTGGGACCACTGTCGGCAGAGGCATCTTGAACGATAGCCTTTCCTTTATCGCAATG
ATGGCATTTGTAGGTGCCACCTTCCTTTTCTACTGTCCTTTTGATGAAGTGACAGATAGCTGGG
CAATGGAATCCGAGGAGGTTTCCCGATATTACCCTTTGTTGAAAAGTCTCAATAGCCCTTTGG
TCTTCTGAGACTGTATCTTTGATATTCTTGGAGTAGACGAGAGTGTCGTGCTCCACCATGTTGG
CAAGCTGCTCTAGCCAATACGCAAACCGCCTCTCCCCGCGCGTTGGCCGATTCATTAATGCAG
CTGGCACGACAGGTTTCCCGACTGGAAAGCGGGCAGTGAGCGCAACGCAATTAATGTGAGTT
AGCTCACTCATTAGGCACCCCAGGCTTTACACTTTATGCTTCCGGCTCGTATGTTGTGTGGAAT
TGTGAGCGGATAACAATTTCACACAGGAAACAGCTATGACCATGATTACGAATTCGAGCTCG
GTACCCGGGGATCCTCTAGAGTCGACCTGCAGGCATGCAAGCTTGGCACTGGCCGTCGTTTTA
CAACGTCGTGACTGGGAAAACCCTGGCGTTACCCAACTTAATCGCCTTGCAGCACATCCCCCT
TTCGCCAGCTGGCGTAATAGCGAAGAGGCCCGCACCGATCGCCCTTCCCAACAGTTGCGCAGC
```

Figure 8B cont'd

CTGAATGGCGAATGCTAGAGCAGCTTGAGCTTGGATCAGATTGTCGTTTCCCGCCTTCAGTTT
AGCTTCATGGAGTCAAAGATTCAAATAGAGGACCTAACAGAACTCGCCGTAAAGACTGGCGA
ACAGTTCATACAGAGTCTCTTACGACTCAATGACAAGAAGAAAATCTTCGTCAACATGGTGGA
GCACGACACACTTGTCTACTCCAAAAATATCAAAGATACAGTCTCAGAAGACCAAAGGGCAA
TTGAGACTTTTCAACAAGGGTAATATCCGGAAACCTCCTCGGATTCCATTGCCCAGCTATCT
GTCACTTTATTGTGAAGATAGTGGAAAAGGAAGGTGGCTCCTACAAATGCCATCATTGCGATA
AAGGAAAGGCCATCGTTGAAGATGCCTCTGCCGACAGTGGTCCCAAAGATGGACCCCCACCC
ACGAGGAGCATCGTGGAAAAAGAAGACGTTCCAACCACGTCTTCAAAGCAAGTGGATTGATG
TGATATCTCCACTGACGTAAGGGATGACGCACAATCCCACTATCCTTCGCAAGACCCTTCCTC
TATATAAGGAAGTTCATTTCATTTGGAGAGAACACGGGGGACTCT

Figure 8 C
SEQ ID NO: 5
Cpn21 RNAi fragment with intron

CTAGTACAAAAAAGCAGGCTGGGGAGGCAGAGGAGAAGACTTTAGGTGGTATCTTACTTCCA
TCCACTGCTCAATCAAAACCTCAAGGAGGTGAAGTCGTTGCCGTGGGTGAAGGAAGAACTAT
TGGGAAGAACAAAATTGATATCACTGTCCCTACTGGAGCACAAATTATCTACTCCAAATACGC
AGGAACTGAGGTGGAGTTCAATGATGTGAAGCATCTTATCCTCAAGGAAGATGATATTGTTGG
CATTCTTGAGACAGAGGACATCAAAGATCTCAAACCTTTGAATGACCGAGTCTTTATTAAGGT
TGCTGAGGCGGAGGAGAAAACAGCTGGAGGGTTGTTGTTAACCGAGACTACCAAAGAGAAGC
CTTCTATTGGCACGGTGATAGCAGTTGGACCGGGTTCCCTAGACGAGGAAGGTAAAATTACGC
CTCTACCAGTATCAACCGGAAGCACCCAGCTTTCATAGTGACTGGATATGTTGTGTTTTACAGT
ATTATGTAGTCTGTTTTTTATGCAAAATCTAATTTAATATATTGATATTTATATCATTTTACGTT
TCTCGTTCAGCTTTCTTGTACAAAGTGGTGATATCACTAGTGCGGCCGCCTGCAGGTCGACCAT
ATGGTCGACCTGCAGGCGGCCGCACTAGTGATGCTGTTATGTTCAGTGTCAAGCTGACCTGCA
AACACGTTAAATGCTAAGAAGTTAGAATATATGAGACACGTTAACTGGTATATGAATAAGCT
GTAAATAACCGAGTATAAACTCATTAACTAATATCACCTCTAGAGTATAATATAATCAAATTC
GACAATTTGACTTTCAAGAGTAGGCTAATGTAAAATCTTTATATATTTCTACAATGTTCAAAG
AAACAGTTGCATCTAAACCCCTATGGCCATCAAATTCAATGAACGCTAAGCTGATCCGGCGAG
ATTTTCAGGAGCTAAGGAAGCTAAAATGGAGAAAAAAATCACTGGATATACCACCGTTGATA
TATCCCAATGGCATCGTAAAGAACATTTTGAGGCATTTCAGTCAGTTGCTCAATGTACCTATA
ACCAGACCGTTCAGCTGGATATTACGGCCTTTTTAAAGACCGTAAAGAAAAATAAGCACAAG
TTTTATCCGGCCTTTATTCACATTCTTGCCCGCCTGATGAATGCTCATCCGGAATTCCGTATGG
CAATGAAAGACGGTGAGCTGGTGATATGGGATAGTGTTCACCCTTGTTACACCGTTTTCCATG
AGCAAACTGAAACGTTTTCATCGCTCTGGAGTGAATACCACGACGATTTCCGGCAGTTTCTAC
ACATATATTCGCAAGATGTGGCGTGTTACGGTGAAAACCTGGCCTATTTCCCTAAAGGGTTTA
TTGAGAATATGTTTTTCGTCTCAGCCAATCCCTGGGTGAGTTTCACCAGTTTTGATTTAAACGT
GGCCAATATGGACAACTTCTTCGCCCCCGTTTTCACCATGGGCAAATATTATACGCAAGGCGA
CAAGGTGCTGATGCCGCTGGCGATTCAGGTTCATCATGCCGTCTGTGATGGCTTCCATGTCGG
CAGAATGCTTAATGAATTACAACAGTACTGCGATGAGTGGCAGGGCGGGGCGTAAACGCGTG
GATCAGCTTAATATGACTCTCAATAAAGTCTCATACCAACAAGTGCCACCTTATTCAACCATC
AAGAAAAAAGCCAAAATTTATGCTACTCTAAGGAAAACTTCACTAAAGAAGACGATTTAGAG
TGTTTTACCAAGAATTTCTGTCATCTTACTAAACAACTAAAGATCGGTGTGATACAAAACCTA
ATCTCATTAAAGTTTATGCTAAAATAAGCATAATTTTACCCACTAAGCGTGACCAGATAAACA
TAACTCAGCACACCAGAGCATATATATTGGTGGCTCAAATCATAGAAACTTACAGTGAAGAC
ACAGAAAGCCGTAAGAAGAGGCAAGAGTATGAAACCTTACCTCATCATTTCCATGAGGTTGC
TTCTGATCCCGCGGGATATCACCACTTTGTACAAGAAAGCTGAACGAGAAACGTAAAATGAT
ATAAATATCAATATATTAAATTAGATTTTGCATAAAAAACAGACTACATAATACTGTAAAACA
CAACATATCCAGTCACTATGAAAGCTGGGTGCTTCCGGTTGATACTGGTAGAGGCGTAATTTT
ACCTTCCTCGTCTAGGGAACCCGGTCCAACTGCTATCACCGTGCCAATAGAAGGCTTCTCTTTG
GTAGTCTCGGTTAACAACAACCCTCCAGCTGTTTTCTCCTCCGCCTCAGCAACCTTAATAAAGA
CTCGGTCATTCAAAGGTTTGAGATCTTTGATGTCCTCTGTCTCAAGAATGCCAACAATATCATC
TTCCTTGAGGATAAGATGCTTCACATCATTGAACTCCACCTCAGTTCCTGCGTATTTGGAGTAG
ATAATTTGTGCTCCAGTAGGGACAGTGATATCAATTTTGTTCTTCCCAATAGTTCTTCCTTCAC
CCACGGCAACGACTTCACCTCCTTGAGGTTTTGATTGAGCAGTGGATGGAAGTAAGATACCAC
CTAAAGTCTTCTCCTCTGCCTCCCCAGCCTGCTTTTTTGTACTAGTG

Figure 8 D
SEQ ID NO: 6
Cpn21 RNAi 35S

AGGATCCCCGGGTACCCTCGAATTATCATACATGAGAATTAAGGGAGTCACGTTATGACCCCC
GCCGATGACGCGGGACAAGCCGTTTTACGTTTGGAACTGACAGAACCGCAACGTTGAAGGAG
CCACTCAGCCGCGGGTTTCTGGAGTTTAATGAGCTAAGCACATACGTCAGAAACCATTATTGC
GCGTTCAAAAGTCGCCTAAGGTCACTATCAGCTAGCAAATATTTCTTGTCAAAAATGCTCCAC
TGACGTTCCATAAATTCCCCTCGGTATCCAATTAGAGTCTCATATTCACTCTCAACTCGATCGA
GGCATGATTGAACAAGATGGATTGCACGCAGGTTCTCCGGCCGCTTGGGTGGAGAGGCTATTC
GGCTATGACTGGGCACAACAGACAATCGGCTGCTCTGATGCCGCCGTGTTCCGGCTGTCAGCG
CAGGGGCGCCCGGTTCTTTTTGTCAAGACCGACCTGTCCGGTGCCCTGAATGAACTCCAAGAC
GAGGCAGCGCGGCTATCGTGGCTGGCCACGACGGGCGTTCCTTGCGCAGCTGTGCTCGACGTT
GTCACTGAAGCGGGAAGGGACTGGCTGCTATTGGGCGAAGTGCCGGGGCAGGATCTCCTGTC
ATCTCACCTTGCTCCTGCCGAGAAAGTATCCATCATGGCTGATGCAATGCGGCGGCTGCATAC
GCTTGATCCGGCTACCTGCCCATTCGACCACCAAGCGAAACATCGCATCGAGCGAGCACGTAC
TCGGATGGAAGCCGGTCTTGTCGATCAGGATGATCTGGACGAAGAGCATCAGGGGCTCGCGC
CAGCCGAACTGTTCGCCAGGCTCAAGGCGCGGATGCCCGACGGCGAGGATCTCGTCGTGACC
CACGGCGATGCCTGCTTGCCGAATATCATGGTGGAAAATGGCCGCTTTTCTGGATTCATCGAC
TGTGGCCGGCTGGGTGTGGCGGACCGCTATCAGGACATAGCGTTGGCTACCCGTGATATTGCT
GAAGAGCTTGGCGGCGAATGGGCTGACCGCTTCCTCGTGCTTTACGGTATCGCCGCTCCCGAT
TCGCAGCGCATCGCCTTCTATCGCCTTCTTGACGAGTTCTTCTGAGCGGGACTCTGGGGTTCGG
ACTCTAGCTAGAGTCAAGCAGATCGTTCAAACATTTGGCAATAAAGTTTCTTAAGATTGAATC
CTGTTGCCGGTCTTGCGATGATTATCATATAATTTCTGTTGAATTACGTTAAGCATGTAATAAT
TAACATGTAATGCATGACGTTATTTATGAGATGGGTTTTTATGATTAGAGTCCCGCAATTATAC
ATTTAATACGCGATAGAAAACAAAATATAGCGCGCAAACTAGGATAAATTATCGCGCGCGGT
GTCATCTATGTTACTAGATCGACCGGCATGCAAGCTGATAATTCAATTCGGCGTTAATTCAGT
ACATTAAAAACGTCCGCAATGTGTTATTAAGTTGTCTAAGCGTCAATTTGTTTACACCACAAT
ATATCCTGCCACCAGCCAGCCAACAGCTCCCCGACCGGCAGCTCGGCACAAAATCACCACTCG
ATACAGGCAGCCCATCAGTCCGGGACGGCGTCAGCGGGAGAGCCGTTGTAAGGCGGCAGACT
TTGCTCATGTTACCGATGCTATTCGGAAGAACGGCAACTAAGCTGCCGGGTTTGAAACACGGA
TGATCTCGCGGAGGGTAGCATGTTGATTGTAACGATGACAGAGCGTTGCTGCCTGTGATCAAT
TCGGGCACGAACCCAGTGGACATAAGCCTCGTTCGGTCGTAAGCTGTAATGCAAGTAGCGTA
ACTGCCGTCACGCAACTGGTCCAGAACCTTGACCGAACGCAGCGGTGGTAACGGCGCAGTGG
CGGTTTTCATGGCTTCTTGTTATGACATGTTTTTTTGGGGTACAGTCTATGCCTCGGGCATCCA
AGCAGCAAGCGCGTTACGCCGTGGGTCGATGTTTGATGTTATGGAGCAGCAACGATGTTACGC
AGCAGGGCAGTCGCCCTAAAACAAAGTTAAACATCATGGGGGAAGCGGTGATCGCCGAAGTA
TCGACTCAACTATCAGAGGTAGTTGGCGTCATCGAGCGCCATCTCGAACCGACGTTGCTGGCC
GTACATTTGTACGGCTCCGCAGTGGATGGCGGCCTGAAGCCACACAGTGATATTGATTTGCTG
GTTACGGTGACCGTAAGGCTTGATGAAACAACGCGGCGAGCTTTGATCAACGACCTTTTGGAA
ACTTCGGCTTCCCCTGGAGAGAGCGAGATTCTCCGCGCTGTAGAAGTCACCATTGTTGTGCAC
GACGACATCATTCCGTGGCGTTATCCAGCTAAGCGCGAACTGCAATTTGGAGAATGGCAGCGC
AATGACATTCTTGCAGGTATCTTCGAGCCAGCCACGATCGACATTGATCTGGCTATCTTGCTG
ACAAAAGCAAGAGAACATAGCGTTGCCTTGGTAGGTCCAGCGGCGGAGGAACTCTTTGATCC
GGTTCCTGAACAGGATCTATTTGAGGCGCTAAATGAAACCTTAACGCTATGGAACTCGCCGCC
CGACTGGGCTGGCGATGAGCGAAATGTAGTGCTTACGTTGTCCCGCATTTGGTACAGCGCAGT
AACCGGCAAAATCGCGCCGAAGGATGTCGCTGCCGACTGGGCAATGGAGCGCCTGCCGGCCC
AGTATCAGCCCGTCATACTTGAAGCTAGACAGGCTTATCTTGGACAAGAAGAAGATCGCTTGG
CCTCGCGCGCAGATCAGTTGGAAGAATTTGTCCACTACGTGAAAGGCGAGATCACCAAGGTA
GTCGGCAAATAATGTCTAGCTAGAAATTCGTTCAAGCCGACGCCGCTTCGCCGGCGTTAACTC
AAGCGATTAGATGCACTAAGCACATAATTGCTCACAGCCAAACTATCAGGTCAAGTCTGCTTT
TATTATTTTTAAGCGTGCATAATAAGCCCTACACAAATTGGGAGATATATCATGCATGACCAA
AATCCCTTAACGTGAGTTTTCGTTCCACTGAGCGTCAGACCCCGTAGAAAAGATCAAAGGATC
TTCTTGAGATCCTTTTTTTCTGCGCGTAATCTGCTGCTTGCAAACAAAAAAACCACCGCTACCA
GCGGTGGTTTGTTTGCCGGATCAAGAGCTACCAACTCTTTTTCCGAAGGTAACTGGCTTCAGC
AGAGCGCAGATACCAAATACTGTCCTTCTAGTGTAGCCGTAGTTAGGCCACCACTTCAAGAAC

Figure 8D cont'd

```
TCTGTAGCACCGCCTACATACCTCGCTCTGCTAATCCTGTTACCAGTGGCTGCTGCCAGTGGCG
ATAAGTCGTGTCTTACCGGGTTGGACTCAAGACGATAGTTACCGGATAAGGCGCAGCGGTCG
GGCTGAACGGGGGGTTCGTGCACACAGCCCAGCTTGGAGCGAACGACCTACACCGAACTGAG
ATACCTACAGCGTGAGCTATGAGAAAGCGCCACGCTTCCCGAAGGGAGAAAGGCGGACAGGT
ATCCGGTAAGCGGCAGGGTCGGAACAGGAGAGCGCACGAGGGAGCTTCCAGGGGGAAACGC
CTGGTATCTTTATAGTCCTGTCGGGTTTCGCCACCTCTGACTTGAGCGTCGATTTTTGTGATGC
TCGTCAGGGGGGCGGAGCCTATGGAAAAACGCCAGCAACGCGGCCTTTTTACGGTTCCTGGCC
TTTTGCTGGCCTTTTGCTCACATGTTCTTTCCTGCGTTATCCCCTGATTCTGTGGATAACCGTAT
TACCGCCTTTGAGTGAGCTGATACCGCTCGCCGCAGCCGAACGACCGAGCGCAGCGAGTCAG
TGAGCGAGGAAGCGGAAGAGCGCCTGATGCGGTATTTTCTCCTTACGCATCTGTGCGGTATTT
CACACCGCATATGGTGCACTCTCAGTACAATCTGCTCTGATGCCGCATAGTTAAGCCAGTATA
CACTCCGCTATCGCTACGTGACTGGGTCATGGCTGCGCCCCGACACCCGCCAACACCCGCTGA
CGCGCCCTGACGGGCTTGTCTGCTCCCGGCATCCGCTTACAGACAAGCTGTGACCGTCTCCGG
GAGCTGCATGTGTCAGAGGTTTTCACCGTCATCACCGAAACGCGCGAGGCAGGGTGCCTTGAT
GTGGGCGCCGGCGGTCGAGTGGCGACGGCGCGGCTTGTCCGCGCCCTGGTAGATTGCCTGGCC
GTAGGCCAGCCATTTTTGAGCGGCCAGCGGCCGCGATAGGCCGACGCGAAGCGGCGGGGCGT
AGGGAGCGCAGCGACCGAAGGGTAGGCGCTTTTTGCAGCTCTTCGGCTGTGCGCTGGCCAGA
CAGTTATGCACAGGCCAGGCGGGTTTTAAGAGTTTTAATAAGTTTTAAAGAGTTTTAGGCGGA
AAAATCGCCTTTTTTCTCTTTTATATCAGTCACTTACATGTGTGACCGGTTCCCAATGTACGGC
TTTGGGTTCCCAATGTACGGGTTCCGGTTCCCAATGTACGGCTTTGGGTTCCCAATGTACGTGC
TATCCACAGGAAAGAGACCTTTTCGACCTTTTTCCCCTGCTAGGGCAATTTGCCCTAGCATCTG
CTCCGTACATTAGGAACCGGCGGATGCTTCGCCCTCGATCAGGTTGCGGTAGCGCATGACTAG
GATCGGGCCAGCCTGCCCCGCCTCCTCCTTCAAATCGTACTCCGGCAGGTCATTTGACCCGAT
CAGCTTGCGCACGGTGAAACAGAACTTCTTGAACTCTCCGGCGCTGCCACTGCGTTCGTAGAT
CGTCTTGAACAACCATCTGGCTTCTGCCTTGCCTGCGGCGCGGCGTGCCAGGCGGTAGAGAAA
ACGGCCGATGCCGGGATCGATCAAAAAGTAATCGGGGTGAACCGTCAGCACGTCCGGGTTCT
TGCCTTCTGTGATCTCGCGGTACATCCAATCAGCTAGCTCGATCTCGATGTACTCCGGCCGCCC
GGTTTCGCTCTTTACGATCTTGTAGCGGCTAATCAAGGCTTCACCCTCGGATACCGTCACCAGG
CGGCCGTTCTTGGCCTTCTTCGTACGCTGCATGGCAACGTGCGTGGTGTTTAACCGAATGCAG
GTTTCTACCAGGTCGTCTTTCTGCTTTCCGCCATCGGCTCGCCGGCAGAACTTGAGTACGTCCG
CAACGTGTGGACGGAACACGCGGCCGGGCTTGTCTCCCTTCCCTTCCCGGTATCGGTTCATGG
ATTCGGTTAGATGGGAAACCGCCATCAGTACCAGGTCGTAATCCCACACACTGGCCATGCCGG
CCGGCCCTGCGGAAACCTCTACGTGCCCGTCTGGAAGCTCGTAGCGGATCACCTCGCCAGCTC
GTCGGTCACGCTTCGACAGACGGAAAACGGCCACGTCCATGATGCTGCGACTATCGCGGGTG
CCCACGTCATAGAGCATCGGAACGAAAAAATCTGGTTGCTCGTCGCCCTTGGGCGGCTTCCTA
ATCGACGGCGCACCGGCTGCCGGCGGTTGCCGGGATTCTTTGCGGATTCGATCAGCGGCCGCT
TGCCACGATTCACCGGGGCGTGCTTCTGCCTCGATGCGTTGCCGCTGGGCGGCCTGCGCGGCC
TTCAACTTCTCCACCAGGTCATCACCCAGCGCCGCGCCGATTTGTACCGGGCCGGATGGTTTG
CGACCGTCACGCCGATTCCTCGGGCTTGGGGGTTCCAGTGCCATTGCAGGGCCGGCAGACAAC
CCAGCCGCTTACGCCTGGCCAACCGCCCGTTCCTCCACACATGGGGCATTCCACGGCGTCGGT
GCCTGGTTGTTCTTGATTTTCCATGCCGCCTCCTTTAGCCGCTAAAATTCATCTACTCATTTATT
CATTTGCTCATTTACTCTGGTAGCTGCGCGATGTATTCAGATAGCAGCTCGGTAATGGTCTTGC
CTTGGCGTACCGCGTACATCTTCAGCTTGGTGTGATCCTCCGCCGGCAACTGAAAGTTGACCC
GCTTCATGGCTGGCGTGTCTGCCAGGCTGGCCAACGTTGCAGCCTTGCTGCTGCGTGCGCTCG
GACGGCCGGCACTTAGCGTGTTTGTGCTTTTGCTCATTTTCTCTTTACCTCATTAACTCAAATG
AGTTTTGATTTAATTTCAGCGGCCAGCGCCTGGACCTCGCGGGCAGCGTCGCCCTCGGGTTCT
GATTCAAGAACGGTTGTGCCGGCGGCGGCAGTGCCTGGGTAGCTCACGCGCTGCGTGATACG
GGACTCAAGAATGGGCAGCTCGTACCCGGCCAGCGCCTCGGCAACCTCACCGCCGATGCGCG
TGCCTTTGATCGCCCGCGACACGACAAAGGCCGCTTGTAGCCTTCCATCCGTGACCTCAATGC
GCTGCTTAACCAGCTCCACCAGGTCGGCGGTGGCCCATATGTCGTAAGGGCTTGGCTGCACCG
GAATCAGCACGAAGTCGGCTGCCTTGATCGCGGACACAGCCAAGTCCGCCGCCTGGGGCGCT
CCGTCGATCACTACGAAGTCGCGCCGGCCGATGGCCTTCACGTCGCGGTCAATCGTCGGGCGG
TCGATGCCGACAACGGTTAGCGGTTGATCTTCCCGCACGGCCGCCCAATCGCGGGCACTGCCC
TGGGGATCGGAATCGACTAACAGAACATCGGCCCCGGCGAGTTGCAGGGCGCGGGCTAGATG
```

Figure 8D cont'd

```
GGTTGCGATGGTCGTCTTGCCTGACCCGCCTTTCTGGTTAAGTACAGCGATAACCTTCATGCGT
TCCCCTTGCGTATTTGTTTATTTACTCATCGCATCATATACGCAGCGACCGCATGACGCAAGCT
GTTTTACTCAAATACACATCACCTTTTTAGACGGCGGCGCTCGGTTTCTTCAGCGGCCAAGCTG
GCCGGCCAGGCCGCCAGCTTGGCATCAGACAAACCGGCCAGGATTTCATGCAGCCGCACGGT
TGAGACGTGCGCGGGCGGCTCGAACACGTACCCGGCCGCGATCATCTCCGCCTCGATCTCTTC
GGTAATGAAAAACGGTTCGTCCTGGCCGTCCTGGTGCGGTTTCATGCTTGTTCCTCTTGGCGTT
CATTCTCGGCGGCCGCCAGGGCGTCGGCCTCGGTCAATGCGTCCTCACGGAAGGCACCGCGCC
GCCTGGCCTCGGTGGGCGTCACTTCCTCGCTGCGCTCAAGTGCGCGGTACAGGGTCGAGCGAT
GCACGCCAAGCAGTGCAGCCGCCTCTTTCACGGTGCGGCCTTCCTGGTCGATCAGCTCGCGGG
CGTGCGCGATCTGTGCCGGGGTGAGGGTAGGGCGGGGGCCAAACTTCACGCCTCGGGCCTTG
GCGGCCTCGCGCCCGCTCCGGGTGCGGTCGATGATTAGGGAACGCTCGAACTCGGCAATGCC
GGCGAACACGGTCAACACCATGCGGCCGGCCGGCGTGGTGGTGTCGGCCCACGGCTCTGCCA
GGCTACGCAGGCCCGCGCCGGCCTCCTGGATGCGCTCGGCAATGTCCAGTAGGTCGCGGGTGC
TGCGGGCCAGGCGGTCTAGCCTGGTCACTGTCACAACGTCGCCAGGGCGTAGGTGGTCAAGC
ATCCTGGCCAGCTCCGGGCGGTCGCGCCTGGTGCCGGTGATCTTCTCGGAAAACAGCTTGGTG
CAGCCGGCCGCGTGCAGTTCGGCCCGTTGGTTGGTCAAGTCCTGGTCGTCGGTGCTGACGCGG
GCATAGCCCAGCAGGCCAGCGGCGGCGCTCTTGTTCATGGCGTAATGTCTCCGGTTCTAGTCG
CAAGTATTCTACTTTATGCGACTAAAACACGCGACAAGAAAACGCCAGGAAAAGGGCAGGGC
GGCAGCCTGTCGCGTAACTTAGGACTTGTGCGACATGTCGTTTTCAGAAGACGGCTGCACTGA
ACGTCAGAAGCCGACTGCACTATAGCAGCGGAGGGGTTGGATCAAAGTACTTTGATCCCGAG
GGGAACCCTGTGGTTGGCATGCACATACAAATGGACGAACGGATAAACCTTTTCACGCCCTTT
TAAATATCCGTTATTCTAATAAACGCTCTTTTCTCTTAGGTTTACCCGCCAATATATCCTGTCA
AACACTGATAGTTTAAACTGAAGGCGGGAAACGACAATCTGATCCAAGCTCAAGCTAAGCTT
GAGCTCTCCCATATGGTCGACTAGAGCCAAGCTGATCTCCTTTGCCCCGGAGATCACCATGGA
CGACTTTCTCTATCTCTACGATCTAGGAAGAAAGTTCGACGGAGAAGGTGACGATACCATGTT
CACCACCGATAATGAGAAGATTAGCCTCTTCAATTTCAGAAAGAATGCTGACCCACAGATGGT
TAGAGAGGCCTACGCGGCAGGTCTCATCAAGACGATCTACCCGAGTAATAATCTCCAGGAGA
TCAAATACCTTCCCAAGAAGGTTAAAGATGCAGTCAAAAGATTCAGGACTAACTGCATCAAG
AACACAGAGAAAGATATATTTCTCAAGATCAGAAGTACTATTCCAGTATGGACGATTCAAGG
CTTGCTTCATAAACCAAGGCAAGTAATAGAGATTGGAGTCTCTAAGAAAGTAGTTCCTACTGA
ATCAAAGGCCATGGAGTCAAAAATTCAGATCGAGGATCTAACAGAACTCGCCGTGAAGACTG
GCGAACAGTTCATACAGAGTCTTTTACGACTCAATGACAAGAAGAAAATCTTCGTCAACATGG
TGGAGCACGACACTCTCGTCTACTCCAAGAATATCAAAGATACAGTCTCAGAAGACCAAAGG
GCTATTGAGACTTTTCAACAAAGGGTAATATCGGGAAACCTCCTCGGATTCCATTGCCCAGCT
ATCTGTCACTTCATCAAAAGGACAGTAGAAAAGGAAGGTGGCACCTACAAATGCCATCATTG
CGATAAAGGAAAGGCTATCGTTCAAGATGCCTCTGCCGACAGTGGTCCCAAAGATGGACCCC
CACCCACGAGGAGCATCGTGGAAAAAGAAGACGTTCCAACCACGTCTTCAAAGCAAGTGGAT
TGATGTGATATCTCCACTGACGTAAGGGATGACGCACAATCCCACTATCCTTCGCAAGACCCT
TCCTCTATATAAGGAAGTTCATTTCATTTGGAGAGGACTGCAGGACGATCCGTATTTTTACAA
CAATTACCACAACAAAACAAACAACAAACAACATTACAATTTACTATTCTAGTCGACCTGCAG
GCGGCCGCACTAGTGATATCACAAGTTTGTACAAAAAAGCTGAACGAGAAACGTAAAATGAT
ATAAATATCAATATATTAAATTAGATTTTGCATAAAAAACAGACTACATAATACTGTAAAACA
CAACATATCCAGTCACTAGTACAAAAAAGCAGGCTGGGGAGGCAGAGGAGAAGACTTAGGT
GGTATCTTACTTCCATCCACTGCTCAATCAAAACCTCAAGGAGGTGAAGTCGTTGCCGTGGGT
GAAGGAAGAACTATTGGGAAGAACAAAATTGATATCACTGTCCCTACTGGAGCACAAATTAT
CTACTCCAAATACGCAGGAACTGAGGTGGAGTTCAATGATGTGAAGCATCTTATCCTCAAGGA
AGATGATATTGTTGGCATTCTTGAGACAGAGGACATCAAAGATCTCAAACCTTTGAATGACCG
AGTCTTTATTAAGGTTGCTGAGGCGGAGGAGAAAACAGCTGGAGGGTTGTTGTTAACCGAGA
CTACCAAAGAGAAGCCTTCTATTGGCACGGTGATAGCAGTTGGACCGGGTTCCCTAGACGAG
GAAGGTAAAATTACGCCTCTACCAGTATCAACCGGAAGCACCCAGCTTTCATAGTGACTGGAT
ATGTTGTGTTTTACAGTATTATGTAGTCTGTTTTTATGCAAAATCTAATTTAATATATTGATAT
TTATATCATTTTACGTTTCTCGTTCAGCTTTCTTGTACAAAGTGGTGATATCCCGCGGGATCAG
AAGCAACCTCATGGAAATGATGAGGTAAGGTTTCATACTCTTGCCTCTTCTTACGGCTTTCTGT
GTCTTCACTGTAAGTTTCTATGATTTGAGCCACCAATATATATGCTCTGGTGTGCTGAGTTATG
```

Figure 8D cont'd

TTTATCTGGTCACGCTTAGTGGGTAAAATTATGCTTATTTTAGCATAAACTTTAATGAGATTAG
GTTTTGTATCACACCGATCTTTAGTTGTTTAGTAAGATGACAGAAATTCTTGGTAAAACACTCT
AAATCGTCTTCTTTAGTGAAGTTTTCCTTAGAGTAGCATAAATTTTGGCTTTTTTCTTGATGGTT
GAATAAGGTGGCACTTGTTGGTATGAGACTTTATTGAGAGTCATATTAAGCTGATCCACGCGT
TTACGCCCCGCCCTGCCACTCATCGCAGTACTGTTGTAATTCATTAAGCATTCTGCCGACATGG
AAGCCATCACAGACGGCATGATGAACCTGAATCGCCAGCGGCATCAGCACCTTGTCGCCTTGC
GTATAATATTTGCCCATGGTGAAAACGGGGGCGAAGAAGTTGTCCATATTGGCCACGTTTAAA
TCAAAACTGGTGAAACTCACCCAGGGATTGGCTGAGACGAAAAACATATTCTCAATAAACCC
TTTAGGGAAATAGGCCAGGTTTTCACCGTAACACGCCACATCTTGCGAATATATGTGTAGAAA
CTGCCGGAAATCGTCGTGGTATTCACTCCAGAGCGATGAAAACGTTTCAGTTTGCTCATGGAA
AACGGTGTAACAAGGGTGAACACTATCCCATATCACCAGCTCACCGTCTTTCATTGCCATACG
GAATTCCGGATGAGCATTCATCAGGCGGGCAAGAATGTGAATAAAGGCCGGATAAAACTTGT
GCTTATTTTTCTTTACGGTCTTTAAAAAGGCCGTAATATCCAGCTGAACGGTCTGGTTATAGGT
ACATTGAGCAACTGACTGAAATGCCTCAAAATGTTCTTTACGATGCCATTGGGATATATCAAC
GGTGGTATATCCAGTGATTTTTTTCTCCATTTTAGCTTCCTTAGCTCCTGAAAATCTCGCCGGA
TCAGCTTAGCGTTCATTGAATTTGATGGCCATAGGGGTTTAGATGCAACTGTTTCTTTGAACAT
TGTAGAAATATATAAAGATTTTACATTAGCCTACTCTTGAAAGTCAAATTGTCGAATTTGATTA
TATTATACTCTAGAGGTGATATTAGTTAATGAGTTTATACTCGGTTATTTACAGCTTATTCATA
TACCAGTTAACGTGTCTCATATATTCTAACTTCTTAGCATTTAACGTGTTTGCAGGTCAGCTTG
ACACTGAACATAACAGCATCACTAGTGCGGCCGCCTGCAGGTCGACCATATGGTCGACCTGCA
GGCGGCCGCACTAGTGATATCACCACTTTGTACAAGAAAGCTGAACGAGAAACGTAAAATGA
TATAAATATCAATATATTAAATTAGATTTTGCATAAAAAACAGACTACATAATACTGTAAAAC
ACAACATATCCAGTCACTATGAAAGCTGGGTGCTTCCGGTTGATACTGGTAGAGGCGTAATTT
TACCTTCCTCGTCTAGGGAACCCGGTCCAACTGCTATCACCGTGCCAATAGAAGGCTTCTCTTT
GGTAGTCTCGGTTAACAACAACCCTCCAGCTGTTTTCTCCTCCGCCTCAGCAACCTTAATAAAG
ACTCGGTCATTCAAAGGTTTGAGATCTTTGATGTCCTCTGTCTCAAGAATGCCAACAATATCAT
CTTCCTTGAGGATAAGATGCTTCACATCATTGAACTCCACCTCAGTTCCTGCGTATTTGGAGTA
GATAATTTGTGCTCCAGTAGGGACAGTGATATCAATTTTGTTCTTCCCAATAGTTCTTCCTTCA
CCCACGGCAACGACTTCACCTCCTTGAGGTTTTGATTGAGCAGTGGATGGAAGTAAGATACCA
CCTAAAGTCTTCTCCTCTGCCTCCCCAGCCTGCTTTTTGTACATAGTGACTGGATATGTTGTGT
TTTACAGTATTATGTAGTCTGTTTTTTATGCAAAATCTAATTTAATATATTGATATTTATATCAT
TTTACGTTTCTCGTTCAGCTTTTTTGTACAAACTTGTGATATCCCGCGGCCATGCTAGAGTCCG
CAAAAATCACCAGTCTCTCTCTACAAATCTATCTCTCTATTTTTCTCCAGAATAATGTGTGA
GTAGTTCCCAGATAAGGGAATTAGGGTTCTTATAGGGTTTCGCTCATGTGTTGAGCATATAAG
AAACCCTTAGTATGTATTTGTATTTGTAAAATACTTCTATCAATAAAATTTCTAATTCCTAAAA
CCAAAATCCAGTGACCTGCAGGCATGCGACGTCGGGCCCTCTAG

Figure 8 E
SEQ ID NO: 7
RBC Cpn21 RNAi Sequence

```
GATAAGCTTGTGGGAACGAGATAAGGGCGAAGTGCGCTAGTAGCCTGCTATTTAAAATATAT
CCACAATTTATAATGTATTTGAAGATTAGTCAATTCGTCCAAAATTCAGGACTAAGTATCTTG
AATTTTTGTATCCTGAATTTTTGGGCTACTAATTTGGAACTCAGGACTTAATGTCCTAAATTTT
TGAGCCGCTAATTTGAAATTCAGGACTAAGTGTTTTGAATTTTTGAACTGCTTATTCGAAATGC
AAGACTAAGTGACATGAATTTTTGAACTGCTAATTTAAAATTCAGGACATAAGATTTGAATTT
TCAAACATAATTTTTTAACTTTAGGGCACGATGTCCTGAAGTTTGAATCTTGAGATCTAAACTT
CAAGATGCAGCGTCTTGAAGTTTGAGTGAACTGGCTAATCTTTAAATACTTGTAAACTGTGGA
TACATTTTTAAATAATATATTTAAAAGCGGCTACCTGGTATCATCTTCACGAGAATTTTCCAAG
TTAATTGTAAAGGAAATAGTGGTGTTGCATCAAGTTATGGACAATATAAGGAAGCAAACAGT
ACTCTAGCTATCAAATTAGTTTCCACTTCTAAACCATGAATATTAGGAAAAACAAGAAACAAA
ACAAATATACATAAACAATACGGCTAAAGCCAAGGAAAAGGGACTCTAAAAAAATTAACCAA
CCTCAATCACACATTCATATCCTCTTCCTACCCCATCTAGGATGAGATAAGATTACTAGGTCTT
ACACGTGGCACCTCCATTGTGGTGACTAAATGAAGAGTGGCTTAGCTCAAAATATAATTTTCC
AACCTTTCATGTGTGGATATTAAGTTTTGTGTAGTGAATCAAGAACCACATAATCCAATGGTT
AGCTTTATTCCAAGATGAGGGGGTTGTTGATTTTGTCCGTCAGATATAGGAAATATGTAAAA
CCTTATCATTATATATAGGGTGGTGGGCAACTATGCAATGACCATATTGGAAGTTAAAGGAAA
AGAGAGAAAGAGAAATTCTTCGTCAACATGGTGGAGCACGACACTCTCGTCTACTCCAAGAA
TATCAAAGATACAGTCTCAGAAGACCAAAGGGCTATTGAGACTTTTCAACAAAGGGTAATAT
CGGGAAACCTCCTCGGATTCCATTGCCCAGCTATCTGTCACTTCATCAAAAGGACAGTAGAAA
AAATAATGATTTTATTTTGACTGATAGTGACCTGTTCGTTGCAACACATTGATGAGCAATGCTT
TTTTATAATGCCAACTTTGTACAAAAAAGCAGGCTGGGGAGGCAGAGGAGAAGACTTTAGGT
GGTATCTTACTTCCATCCACTGCTCAATCAAAACCTCAAGGAGGTGAAGTCGTTGCCGTGGGT
GAAGGAAGAACTATTGGGAAGAACAAAATTGATATCACTGTCCCTACTGGAGCACAAATTAT
CTACTCCAAATACGCAGGAACTGAGGTGGAGTTCAATGATGTGAAGCATCTTATCCTCAAGGA
AGATGATATTGTTGGCATTCTTGAGACAGAGGACATCAAAGATCTCAAACCTTTGAATGACCG
AGTCTTTATTAAGGTTGCTGAGGCGGAGGAGAAAACAGCTGGAGGGTTGTTGTTAACCGAGA
CTACCAAAGAGAAGCCTTCTATTGGCACGGTGATAGCAGTTGGACCGGGTTCCCTAGACGAG
GAAGGTAAAATTACGCCTCTACCAGTATCAACCGGAAGCACCCAGCTTTCTTGTACAAAGTTG
GCATTATAAGAAAGCATTGCTTATCAATTTGTTGCAACGAACAGGTCACTATCAGTCAAAATA
AAATCATTATTTATCAGAAGCAACCTCATGGAAATGATGAGGTAAGGTTTCATACTCTTGCCT
CTTCTTACGGCTTTCTGTGTCTTCACTGTAAGTTTCTATGATTTGAGCCACCAATATATATGCTC
TGGTGTGCTGAGTTATGTTTATCTGGTCACGCTTAGTGGGTAAAATTATGCTTATTTTAGCATA
AACTTTAATGAGATTAGGTTTTGTATCACACCGATCTTTAGTTGTTTAGTAAGATGACAGAAAT
TCTTGGTAAAACACTCTAAATCGTCTTCTTTAGTGAAGTTTTCCTTAGAGTAGCATAAATTTTG
GCTTTTTTCTTGATGGTTGAATAAGGTGGCACTTGTTGGTATGAGACTTTATTGAGAGTCATAT
TAAGCTGATCCACGCGTTTACGCCCCGCCCTGCCACTCATCGCAGTACTGTTGTAATTCATTAA
GCATTCTGCCGACATGGAAGCCATCACAGACGGCATGATGAACCTGAATCGCCAGCGGCATC
AGCACCTTGTCGCCTTGCGTATAATATTTGCCCATGGTGAAAACGGGGGCGAAGAAGTTGTCC
ATATTGGCCACGTTTAAATCAAAACTGGTGAAACTCACCCAGGGATTGGCTGAGACGAAAAA
CATATTCTCAATAAACCCTTTAGGGAAATAGGCCAGGTTTTCACCGTAACACGCCACATCTTG
CGAATATATGTGTAGAAACTGCCGGAAATCGTCGTGGTATTCACTCCAGAGCGATGAAAACGT
TTCAGTTTGCTCATGGAAACGGTGTAACAAGGGTGAACACTATCCCATATCACCAGCTCACC
GTCTTTCATTGCCATACGGAATTCCGGATGAGCATTCATCAGGCGGGCAAGAATGTGAATAAA
GGCCGGATAAAACTTGTGCTTATTTTCTTTACGGTCTTTAAAAAGGCCGTAATATCCAGCTGA
ACGGTCTGGTTATAGGTACATTGAGCAACTGACTGAAATGCCTCAAAATGTTCTTTACGATGC
CATTGGGATATATCAACGGTGGTATATCCAGTGATTTTTTCTCCATTTTAGCTTCCTTAGCTCC
TGAAAATCTCGCCGGATCAGCTTAGCGTTCATTGAATTTGATGGCCATAGGGGTTTAGATGCA
ACTGTTTCTTTGAACATTGTAGAAATATATAAAGATTTTACATTAGCCTACTCTTGAAAGTCAA
ATTGTCGAATTTGATTATATTATACTCTAGAGGTGATATTAGTTAATGAGTTTATACTCGGTTA
TTTACAGCTTATTCATATACCAGTTAACGTGTCTCATATATTCTAACTTCTTAGCATTTAACGT
GTTTGCAGGTCAGCTTGACACTGAACATAACAGCATCACTAGTGCGGCCGCCTGCAGGTCGAC
```

Figure 8E cont'd

```
CATATGGTCGACCTGCAGGCGGCCGCACTAGTGATATCAAATAATGATTTTATTTTGACTGAT
AGTGACCTGTTCGTTGCAACAAATTGATAAGCAATGCTTTCTTATAATGCCAACTTTGTACAA
GAAAGCTGGGTGCTTCCGGTTGATACTGGTAGAGGCGTAATTTTACCTTCCTCGTCTAGGGAA
CCCGGTCCAACTGCTATCACCGTGCCAATAGAAGGCTTCTCTTTGGTAGTCTCGGTTAACAAC
AACCCTCCAGCTGTTTTCTCCTCCGCCTCAGCAACCTTAATAAAGACTCGGTCATTCAAAGGTT
TGAGATCTTTGATGTCCTCTGTCTCAAGAATGCCAACAATATCATCTTCCTTGAGGATAAGATG
CTTCACATCATTGAACTCCACCTCAGTTCCTGCGTATTTGGAGTAGATAATTTGTGCTCCAGTA
GGGACAGTGATATCAATTTTGTTCTTCCCAATAGTTCTTCCTTCACCCACGGCAACGACTTCAC
CTCCTTGAGGTTTTGATTGAGCAGTGGATGGAAGTAAGATACCACCTAAAGTCTTCTCCTCTG
CCTCCCCAGCCTGCTTTTTTGTACAAAGTTGGCATTATAAAAAAGCATTGCTCATCAATGTGTT
GCAACGAACAGGTCACTATCAGTCAAAATAAAATCATTATTTGATATCCCGCGGCCATGCTAG
AGTCCGCAAAAATCACCAGTCTCTCTACAAATCTATCTCTCTATTTTCTCCAGAATAAT
GTGTGAGTAGTTCCCAGATAAGGGAATTAGGGTTCTTATAGGGTTTCGCTCATGTGTTGAGCA
TATAAGAAACCCTTAGTATGTATTTGTATTTGTAAAATACTTCTATCAATAAAATTTCTAATTC
CTAAAACCAAAATCCAGTGACCTGCAGGCATGCGACGTCGGGCCCTCTAGAGGATCCCCGGG
GGATCCACTAGTTCTAGAGCGGCCGCCACCGCGGTGGAGCTCCAGCTTTTGTTCCCTTTAGTG
AGGGTTAATTCCGAGCTTGGCGTAATCATGGTCATAGCTGTTTCCTGTGTGAAATTGTTATCCG
CTCACAATTCCACACAACATACGAGCCGGAAGHCATAAAGTGTAAAGCCTGGGGTGCCTAAT
GAGTGAGCTAACTCACATTAATTGCGTTGCGCTCACTGCCCGCTTTCCAGTCGGGAAACCTGT
CGTGCCAGCTGCATTAATGAATCGGCCAACGCGCGGGGAGAGGCGGTTTGCGTATTGGGCGC
TCTTCCGCTTCCTCGCTCACTGACTCGCTGCGCTCGGTCGTTCGGCTGCGGCGAGCGGTATCAG
CTCACTCAAAGGCGGTAATACGGTTATCCACAGAATCAGGGGATAACGCAGGAAAGAACATG
AAGGCCTTGACAGGATATATTGGCGGGTAAACTAAGTCGCTGTATGTGTTTGTTTGAGATCTC
ATGTGAGCAAAAGGCCAGCAAAAGGCCAGGAACCG2AAAAAGGCCGCGTTGCTGGCGTTTTT
CCATAGGCTCCGCCCCCTGACGAGCATCACAAAAATCGACGCTCAAGTCAGAGGTGGCGAA
ACCCGACAGGACTATAAAGATACCAGGCGTTTCCCCCTGGAAGCTCCCTCGTGCGCTCTCCTG
TTCCGACCCTGCCGCTTACCGGATACCTGTCCGCCTTTCTCCCTTCGGGAAGCGTGGCGCTTTC
TCATAGCTCACGCTGTAGGTATCTCAGTTCGGTGTAGGTCGTTCGCTCCAAGCTGGGCTGTGTG
CACGAACCCCCCGTTCAGCCCGACCGCTGCGCCTTATCCGGTAACTATCGTCTTGAGTCCAAC
CCGGTAAGACACGACTTATCGCCACTGGCAGCAGCCACTGGTAACAGGATTAGCAGAGCGAG
GTATGTAGGCGGTGCTACAGAGTTCTTGAAGTGGTGGCCTAACTACGGCTACACTAGAAGAAC
AGTATTTGGTATCTGCGCTCTGCTGAAGCCAGTTACCTTCGGAAGAAGAGTTGGTAGCTCTTG
ATCCGGCAAACAAACCACCGCTGGTAGCGGTGGTTTTTTTGTTTGCAAGCAGCAGATTACGCG
CAGAAAAAAAGGATCTCAAGAAGATCCTTTGATCTTTTCTACGGGGTCTGACGCTCAGTGGAA
CGAAAACTCACGTTAAGGGATTTTGGTCATGAGATTATCAAAAAGGATCTTCACCTAGATCCT
TTTAAATTAAAAATGAAGTTTTAAATCAATCTAAAGTATATATGTGTAACATTGGTCTAGTGA
TTAGAAAAACTCATCGAGCATCAAATGAAACTGCAATTTATTCATATCAGGATTATCAATACC
ATATTTTTGAAAAAGCCGTTTCTGTAATGAAGGAGAAAACTCACCGAGGCAGTTCCATAGGAT
GGCAAGATCCTGGTATCGGTCTGCGATTCCGACTCGTCCAACATCAATACAACCTATTAATTT
CCCCTCGTCAAAAATAAGGTTATCAAGTGAGAAATCACCATGAGTGACGACTGAATCCGGTG
AGAATGGCAAAAGTTTATGCATTTCTTTCCAGACTTGTTCAACAGGCCAGCCATTACGCTCGT
CATCAAAATCACTCGCATCAACCAAACCGTTATTCATTCGTGATTGCGCCTGAGCGAGACGAA
ATACGCGATCGCTGTTAAAAGGACAATTACAAACAGGAATCGAATGCAACCGGCGCAGGAAC
ACTGCCAGCGCATCAACAATATTTTCACCTGAATCAGGATATTCTTCTAATACCTGGAATGCT
GTTTTCCCTGGGATCGCAGTGGTGAGTAACCATGCATCATCAGGAGTACGGATAAAATGCTTG
ATGGTCGGAAGAGGCATAAATTCCGTCAGCCAGTTTAGTCTGACCATCTCATCTGTAACAACA
TTGGCAACGCTACCTTTGCCATGTTTCAGAAACAACTCTGGCGCATCGGGCTTCCCATACAAT
CGGTAGATTGTCGCACCTGATTGCCCGACATTATCGCGAGCCCATTTATACCCATATAAATCA
GCATCCATGTTGGAATTTAATCGCGGCCTTGAGCAAGACGTTTCCCGTTGAATATGGCTCATA
ACACCCCTTGTATTACTGTTTATGTAAGCAGACAGTTTTATTGTTCATGATGATATATTTTTATC
TTGTGCAATGTAACATCAGAGATTTTGAGACACAACGTGGCTTTGTTGAATAAATCGAACTTT
TGCTGAGTTGAAGGATCAGATCACGCATCTTCCCGACAACGCAGACCGTTCCGTGGCAAAGCA
AAAGTTCAAAATCACCAACTGGTCCACCTACAACAAAGCTCTCATCAACCGTGGCTCCCTCAC
TTTCTGGCTGGATGATGGGGCGATTCAGGCGATCCCCATCCAACAGCCCGCCGTCGAGCGGGC
TTTTTTATCCCCGGAAGCCTGTGGATAGAGGGTAGTTATCCACGTGAAACCGCTAATGCCCCG
```

Figure 8E cont'd
CAAAGCCTTGATTCACGGGGCTTTCCGGCCCGCTCCAAAAACTATCCACGTGAAATCGCTAAT
CAGGGTACGTGAAATCGCTAATCGGAGTACGTGAAATCGCTAATAAGGTCACGTGAAATCGC
TAATCAAAAAGGCACGTGAGAACGCTAATAGCCCTTTCAGATCAACAGCTTGCAAACACCCCT
CGCTCCGGCAAGTAGTTACAGCAAGTAGTATGTTCAATTAGCTTTTCAATTATGAATATATAT
ATCAATTATTGGTCGCCCTTGGCTTGTGGACAATGCGCTACGCGCACCGGCTCCGCCCGTGGA
CAACCGCAAGCGGTTGCCCACCGTCGAGCGCCAGCGCCTTTGCCCACAACCCGGCGGCCGGC
CGCAACAGATCGTTTTATAAATTTTTTTTTTGAAAAAGAAAAAGCCCGAAAGGCGGCAACCT
CTCGGGCTTCTGGATTTCCGATCCCCGGAATTAGAGATCTTGGCAGGATATATTGTGGTGTAA
CGTTATCAGCTTGCATGCCGGTCGATCTAGTAACATAGATGACACCGCGCGATAATTTATC
CTAGTTTGCGCGCTATATTTTGTTTTCTATCGCGTATTAAATGTATAATTGCGGGACTCTAATC
AAAAAACCCATCTCATAAATAACGTCATGCATTACATGTTAATTATTACATGCTTAACGTAAT
TCAACAGAAATTATATGATAATCATCGCAAGACCGGCAACAGGATTCAATCTTAAGAAACTTT
ATTGCCAAATGTTTGAACGATCTGCTTGACTCTAGCTAGAGTCCGAACCCCAGAGTCCCGCTC
AGAAGAACTCGTCAAGAAGGCGATAGAAGGCGATGCGCTGCGAATCGGGAGCGGCGATACC
GTAAAGCACGAGGAAGCGGTCAGCCCATTCGCCGCCAAGCTCTTCAGCAATATCACGGGTAG
CCAACGCTATGTCCTGATAGCGGTCCGCCACACCCAGCCGGCCACAGTCGATGAATCCAGAA
AAGCGGCCATTTTCCACCATGATATTCGGCAAGCAGGCATCGCCCTGGGTCACGACGAGATCC
TCGCCGTCGGGCATCCGCGCCTTGAGCCTGGCGAACAGTTCGGCTGGCGCGAGCCCCTGATGC
TCTTCGTCCAGATCATCCTGATCGACAAGACCGGCTTCCATCCGAGTACGTCCTCGCTCGATGC
GATGTTTCGCTTGGTGGTCGAATGGGCAGGTAGCCGGATCAAGCGTATGCAGCCGCCGCATTG
CATCAGCCATGATGGATACTTTCTCGGCAGGAGCAAGGTGAGATGACAGGAGATCCTGCCCC
GGCACTTCGCCCAATAGCAGCCAGTCCCTTCCCGCTTCAGTGACAACGTCGAGCACAGCTGCG
CAAGGAACGCCCGTCGTGGCCAGCCACGATAGCCGCGCTGCCTCGTCTTGGAGTTCATTCAGG
GCACCGGACAGGTCGGTCTTGACAAAAAGAACCGGGCGCCCTGCGCTGACAGCCGGAACAC
GGCGGCATCAGAGCAGCCGATTGTCTGTTGTGCCCAGTCATAGCCGAATAGCCTCTCCACCCA
AGCGGCCGGAGAACCTGCGTGCAATCCATCTTGTTCAATCATGCCTCGATCGAGTTGAGAGTG
AATATGAGACTCTAATTGGATACCGAGGGGAATTTATGGAACGTCAGTGGAGCATTTTTGACA
AGAAATATTTGCTAGCTGATAGTGACCTTAGGCGACTTTTGAACGCGCAATAATGGTTTCTGA
CGTATGTGCTTAGCTCATTAAACTCCAGAAACCCGCGGCTGAGTGGCTCCTTCAACGTTGCGG
TTCTGTCAGTTCCAAACGTAAAACGGCTTGTCCCGCGTCATCGGCGGGGGTCATAACGTGACT
CCCCTTAATTCTCATGTATCGATAACATTAACGTTTACAATTTCGCGCCATTCGCCATTCAGGCT
GCGCAACTGTTGGGAAGGGCGATCGGTGCGGGCCTCTTCGCTATTACGCCAGCTGGCGAAAG
GGGGATGTGCTGCAAGGCGATTAAGTTGGGTAACGCCAGGGTTTTCCCAGTCACGACGTTGTA
AAACGACGGCCAGTGAATTGTAATACGACTCACTATAGGGCGAATTGGGTACCGGGCCCCCC
CTCGAGGTCGACGGTATCGATAAGCTTGATATCGAATTCCTGCA

Figure 8 F
SEQ ID NO: 8
AlcR Cpn21 RNAi Sequence
ATTCAGGGCACCGGACAGGTCGGTCTTGACAAAAAGAACCGGGCGCCCCTGCGCTGACAGCC
GGAACACGGCGGCATCAGAGCAGCCGATTGTCTGTTGTGCCCAGTCATAGCCGAATAGCCTCT
CCACCCAAGCGGCCGGAGAACCTGCGTGCAATCCATCTTGTTCAATCATGCCTCGATCGAGTT
GAGAGTGAATATGAGACTCTAATTGGATACCGAGGGGAATTTATGGAACGTCAGTGGAGCAT
TTTTGACAAGAAATATTTGCTAGCTGATAGTGACCTTAGGCGACTTTTGAACGCGCAATAATG
GTTTCTGACGTATGTGCTTAGCTCATTAAACTCCAGAAACCCGCGGCTGAGTGGCTCCTTCAA
CGTTGCGGTTCTGTCAGTTCCAAACGTAAAACGGCTTGTCCCGCGTCATCGGCGGGGGTCATA
ACGTGACTCCCTTAATTCTCATGTATCGATAACATTAACGTTTACAATTTCGCGCCATTCGCCA
TTCAGGCTGCGCAACTGTTGGGAAGGGCGATCGGTGCGGGCCTCTTCGCTATTACGCCAGCTG
GCGAAAGGGGGATGTGCTGCAAGGCGATTAAGTTGGGTAACGCCAGGGTTTTCCCAGTCACG
ACGTTGTAAAACGACGGCCAGTGAATTGTAATACGACTCACTATAGGGCGAATTGGGTACCG
GCCCCCCCTCGAGGTCGACTGCCAACATGGTGGAGCACGACACTCTCGTCTACTCCAAGAAT
ATCAAAGATACAGTCTCAGAAGACCAAAGGGCTATTGAGACTTTTCAACAAAGGGTAATATC

Figure 8F cont'd

```
GGGAAACCTCCTCGGATTCCATTGCCCAGCTATCTGTCACTTCATCAAAAGGACAGTAGAAAA
GGAAGGTGGCACCTACAAATGCCATCATTGCGATAAAGGAAAGGCTATCGTTCAAGATGCCT
CTGCCGACAGTGGTCCCAAAGATGGACCCCCACCCACGAGGAGCATCGTGGAAAAAGAAGAC
GTTCCAACCACGTCTTCAAAGCAAGTGGATTGATGTGATAACATGGTGGAGCACGACACTCTC
GTCTACTCCAAGAATATCAAAGATACAGTCTCAGAAGACCAAAGGGCTATTGAGACTTTTCAA
CAAAGGGTAATATCGGGAAACCTCCTCGGATTCCATTGCCCAGCTATCTGTCACTTCATCAAA
AGGACAGTAGAAAAGGAAGGTGGCACCTACAAATGCCATCATTGCGATAAAGGAAAGGCTAT
CGTTCAAGATGCCTCTGCCGACAGTGGTCCCAAAGATGGACCCCCACCCACGAGGAGCATCGT
GGAAAAAGAAGACGTTCCAACCACGTCTTCAAAGCAAGTGGATTGATGTGATATCTCCACTG
ACGTAAGGGATGACGCACAATCCCACTATCCTTCGCAAGACCTTCCTCTATATAAGGAAGTTC
ATTTCATTTGGAGAGGACACGCTGAAATCACCAGTCTCTCTACAAATCTATCTCTCTCGAGC
TTTCGCAGATCCCGGGGAGTACTATGTGCTGGAACCCCGCATGCTCCAGGCCTCATTCCCCAG
ATTTCGACTCCATGGCTGACAGCATCCAGACCGCACGTTTTGGACTTCTGATACCATCTATAC
AGATATCACTGTCGATATTCTCCTGCACACAGCATGGCAGATACGCGCCGACGCCAGAATCAT
AGCTGCGATCCCTGTCGCAAGGGCAAGCGACGCTGTGATGCCCCGAAACGAGGCCAATGAAA
ACGGCTGGGTTTCGTGTTCAAATTGCAAGCGTTGGAACAAGGATTGTACCTTCAATTGGCTCT
CATCCCAACGCTCCAAGGCAAAAGGGGCTGCACCTAGAGCGAGAACAAAGAAAGCCAGGAC
CGCAACAACCACCAGTGAACCATCAACTTCAGCTGCAACAATCCCTACACCGGAAAGTGACA
ATCACGATGCGCCTCCAGTCATAAACTCTCACGACGCGCTCCCGAGCTGGACTCAGGGGCTAC
TCTCCCACCCCGGCGACCTTTTCGATTTCAGCCACTCTGCTATTCCCGCAAATGCAGAAGATGC
GGCCAACGTGCAGTCAGACGCACCTTTTCCGTGGGATCTAGCCATCCCCGGTGATTTCAGCAT
GGGCCAACAGCTCGAGAAACCTCTCAGTCCGCTCAGTTTTCAAGCAGTCCTTCTTCCGCCCCA
TAGCCCGAACACGGATGACCTCATTCGCGAGCTGGAAGAGCAGACTACGGATCCGGACTCGG
TTACCGATACTAATAGTGTACAACAGGTCGCTCAAGATGGATCGCTATGGTCTGATCGGCAGT
CGCCGCTACTGCCTGAGAACAGTCTGTGCATGGCCTCAGACAGCACAGCACGGCGATATGCCC
GTTCCACAATGACGAAGAATCTGATGCGAATCTACCACGATAGTATGGAGAATGCACTGTCCT
GCTGGCTGACAGAGCACAATTGTCCATACTCCGACCAGATCAGCTACCTGCCGCCCAAGCAGC
GGGCGGAATGGGGCCCGAACTGGTCAAACAGGATGTGCATCCGGGTGTGCCGGCTAGATCGC
GTATCTACCTCATTACGCGGGCGCGCCCTGAGTGCGGAAGAGGACAAAGCCGCAGCCCGAGC
CCTGCATCTGGCGATCGTAGCTTTTGCGTCGCAATGGACGCAGCATGCGCAGAGGGGGCTGG
GCTAAATGTTCCTGCAGACATAGCCGCCGATGAGAGGTCCATCCGGAGGAACGCCTGGAATG
AAGCACGCCATGCCTTGCAGCACACGACAGGGATTCCATCATTCCGGGTTATATTTGCGAATA
TCATCTTTTCTCTCACGCAGAGTGTGCTGGATGATGATGAGCAGCACGGTATGGGTGCACGTC
TAGACAAGCTACTCGAAAATGACGGTGCGCCCGTGTTCCTGGAAACCGCGAACCGTCAGCTTT
ATACATTCCGACATAAGTTTGCACGAATGCAACGCCGCGGTAAGGCTTTCAACAGGCTCCCGG
GAGGATCTGTCGCATCGACATTCGCCGGTATTTTCGAGACACCGACGCCGTCGTCTGAAAGCC
CACAGCTTGACCCGGTTGTGGCCAGTGAGGAGCATCGCAGTACATTAAGCCTTATGTTCTGGC
TAGGGATCATGTTCGATACACTAAGCGCTGCAATGTACCAGCGACCACTCGTGGTGTCAGATG
AGGATAGCCAGATATCATCGGCATCTCCACCAAGGCGCGGCGCTGAAACGCCGATCAACCTA
GACTGCTGGGAGCCCCGAGACAGGTCCCGAGCAATCAAGAAAAGAGCGACGTATGGGGCG
ACCTCTTCCTCCGCACCTCGGACTCTCTCCCAGATCACGAATCCCACACACAAATCTCTCAGCC
AGCGGCTCGATGGCCCTGCACCTACGAACAGGCCGCCGCCGCTCTCTCCTCTGCAACGCCCGT
CAAAGTCCTCCTCTACCGCCGCGTCACGCAGCTCCAAACCCTCCTCTATCGCGGCGCCAGCCC
TGCCCGCCTTGAAGCGGCCATCCAGAGAACGCTCTACGTTTATAATCACTGGACAGCGAAGTA
CCAACCATTTATGCAGGACTGCGTTGCTAACCACGAGCTCCTCCCTTCGCGCATCCAGTCTTGG
TACGTCATTCTAGACGGTCACTGGCATCTAGCCGCGATGTTGCTAGCGGACGTTTTGGAGAGC
ATCGACCGCGATTCGTACTCTGATATCAACCACATCGACCTTGTAACAAAGCTAAGGCTCGAT
AATGCACTAGCAGTTAGTGCCCTTGCGCGCTCTTCACTCCGAGGCCAGGAGCTGGACCCGGGC
AAAGCATCTCCGATGTATCGCCATTTCCATGATTCTCTGACCGAGGTGGCATTCCTGGTAGAA
CCGTGGACCGTCGTTCTTATTCACTCGTTTGCCAAAGCTGCGTATATCTTGCTGGACTGTTTAG
ATCTGGACGGCCAAGGAAATGCACTAGCGGGGTACCTGCAGCTGCGGCAAAATTGCAACTAC
TGCATTCGGGCGCTGCAATTTCTGGGCAGGAAGTCGGATATGGCGGCGCTGGTTGCGAAGGAT
TTAGAGAGAGGGTTTGAATGGGAAAGTTGACAGCTTTTTGTAGGGAGCGGGACTCTGGGGTTCG
GACTCTAGCTAGAGTCAAGCAGATCGTTCAAACATTTGGCAATAAAGTTTCTTAAGATTGAAT
CCTGTTGCCGGTCTTGCGATGATTATCATATAATTTCTGTTGAATTACGTTAAGCATGTAATAA
```

Figure 8F cont'd

```
TTAACATGTAATGCATGACGTTATTTATGAGATGGGTTTTTTGATTAGAGTCCCGCAATTATAC
ATTTAATACGCGATAGAAAACAAAATATAGCGCGCAAACTAGGATAAAAAGCTTCCGGGATA
GTTCCGACCTAGGATTGGATGCATGCGGAACCGCACGAGGGCGGGGCGGAAATTGACACACC
ACTCCTCTCCACGCAGCCGTTCAAGAGGTACGCGTATAGAGCCGTATAGAGCAGAGACGGAG
CACTTTCTGGTACTGTCCGCACGGGATGTCCGCACGGAGAGCCACAAACGAGCGGGGCCCCG
TACGTGCTCTCCTACCCCAGGATCGCATCCTCGCATAGCTGAACATCTATATAAGGAAGTTCA
TTTCATTTGGAGAGGACACGCTGAAATCACCAGTCTCTCTCTACAAATCTATCTCTCTCGAGCT
TTCGCAGATCCCGGGGAGTACTCGAAGTACTTCAGATATCGAATTCCTGCAGCGGATCCACTA
GTTCTAGACACGTGATTTAAATGGTTTCTTCGTCAACATGGTGGAGCACGACACTCTCGTCTAC
TCCAAGAATATCAAAGATACAGTCTCAGAAGACCAAAGGGCTATTGAGACTTTTCAACAAAG
GGTAATATCGGGAAACCTCCTCGGATTCCATTGCCCAGCTATCTGTCACTTCATCAAAAGGAC
AGTAGAAAAAATAATGATTTTATTTTGACTGATAGTGACCTGTTCGTTGCAACACATTGATGA
GCAATGCTTTTTTATAATGCCAACTTTGTACAAAAAAGCAGGCTGGGGAGGCAGAGGAGAAG
ACTTTAGGTGGTATCTTACTTCCATCCACTGCTCAATCAAAACCTCAAGGAGGTGAAGTCGTT
GCCGTGGGTGAAGGAAGAACTATTGGGAAGAACAAAATTGATATCACTGTCCCTACTGGAGC
ACAAATTATCTACTCCAAATACGCAGGAACTGAGGTGGAGTTCAATGATGTGAAGCATCTTAT
CCTCAAGGAAGATGATATTGTTGGCATTCTTGAGACAGAGGACATCAAAGATCTCAAACCTTT
GAATGACCGAGTCTTTATTAAGGTTGCTGAGGCGGAGGAGAAAACAGCTGGAGGGTTGTTGT
TAACCGAGACTACCAAAGAGAAGCCTTCTATTGGCACGGTGATAGCAGTTGGACCGGGTTCCC
TAGACGAGGAAGGTAAAATTACGCCTCTACCAGTATCAACCGGAAGCACCCAGCTTTCTTGTA
CAAAGTTGGCATTATAAGAAAGCATTGCTTATCAATTTGTTGCAACGAACAGGTCACTATCAG
TCAAAATAAAATCATTATTTATCAGAAGCAACCTCATGGAAATGATGAGGTAAGGTTTCATAC
TCTTGCCTCTTCTTACGGCTTTCTGTGTCTTCACTGTAAGTTTCTATGATTTGAGCCACCAATAT
ATATGCTCTGGTGTGCTGAGTTATGTTTATCTGGTCACGCTTAGTGGGTAAAATTATGCTTATT
TTAGCATAAACTTTAATGAGATTAGGTTTTGTATCACACCGATCTTTAGTTGTTTAGTAAGATG
ACAGAAATTCTTGGTAAAACACTCTAAATCGTCTTCTTTAGTGAAGTTTTCCTTAGAGTAGCAT
AAATTTTGGCTTTTTTCTTGATGGTTGAATAAGGTGGCACTTGTTGGTATGAGACTTTATTGAG
AGTCATATTAAGCTGATCCACGCGTTTACGCCCCGCCCTGCCACTCATCGCAGTACTGTTGTAA
TTCATTAAGCATTCTGCCGACATGGAAGCCATCACAGACGGCATGATGAACCTGAATCGCCAG
CGGCATCAGCACCTTGTCGCCTTGCGTATAATATTTGCCCATGGTGAAAACGGGGGCGAAGAA
GTTGTCCATATTGGCCACGTTTAAATCAAAACTGGTGAAACTCACCCAGGGATTGGCTGAGAC
GAAAAACATATTCTCAATAAACCCTTTAGGGAAATAGGCCAGGTTTTCACCGTAACACGCCAC
ATCTTGCGAATATATGTGTAGAAACTGCCGGAAATCGTCGTGGTATTCACTCCAGAGCGATGA
AAACGTTTCAGTTTGCTCATGGAAAACGGTGTAACAAGGGTGAACACTATCCCATATCACCAG
CTCACCGTCTTTCATTGCCATACGGAATTCCGGATGAGCATTCATCAGGCGGGCAAGAATGTG
AATAAAGGCCGGATAAAACTTGTGCTTATTTTTCTTTACGGTCTTTAAAAAGGCCGTAATATCC
AGCTGAACGGTCTGGTTATAGGTACATTGAGCAACTGACTGAAATGCCTCAAAATGTTCTTTA
CGATGCCATTGGGATATATCAACGGTGGTATATCCAGTGATTTTTTCTCCATTTTAGCTTCCT
TAGCTCCTGAAAATCTCGCCGGATCAGCTTAGCGTTCATTGAATTTGATGGCCATAGGGGTTT
AGATGCAACTGTTTCTTTGAACATTGTAGAAATATATAAAGATTTTACATTAGCCTACTCTTGA
AAGTCAAATTGTCGAATTTGATTATATTATACTCTAGAGGTGATATTAGTTAATGAGTTTATAC
TCGGTTATTTACAGCTTATTCATATACCAGTTAACGTGTCTCATATATTCTAACTTCTTAGCATT
TAACGTGTTTGCAGGTCAGCTTGACACTGAACATAACAGCATCACTAGTGCGGCCGCCTGCAG
GTCGACCATATGGTCGACCTGCAGGCGGCCGCACTAGTGATATCAAATAATGATTTTATTTTG
ACTGATAGTGACCTGTTCGTTGCAACAAATTGATAAGCAATGCTTTCTTATAATGCCAACTTTG
TACAAGAAAGCTGGGTGCTTCCGGTTGATACTGGTAGAGGCGTAATTTTACCTTCCTCGTCTA
GGGAACCCGGTCCAACTGCTATCACCGTGCCAATAGAAGGCTTCTCTTTGGTAGTCTCGGTTA
ACAACAACCCTCCAGCTGTTTTCTCCTCCGCCTCAGCAACCTTAATAAAGACTCGGTCATTCAA
AGGTTTGAGATCTTTGATGTCCTCTGTCTCAAGAATGCCAACAATATCATCTTCCTTGAGGATA
AGATGCTTCACATCATTGAACTCCACCTCAGTTCCTGCGTATTTGGAGTAGATAATTTGTGCTC
CAGTAGGGACAGTGATATCAATTTTGTTCTTCCCAATAGTTCTTCCTTCACCCACGGCAACGAC
TTCACCTCCTTGAGGTTTTGATTGAGCAGTGGATGGAAGTAAGATACCACCTAAAGTCTTCTC
CTCTGCCTCCCCAGCCTGCTTTTTGTACAAAGTTGGCATTATAAAAAGCATTGCTCATCAAT
GTGTTGCAACGAACAGGTCACTATCAGTCAAAATAAAATCATTATTTGATATCCCGCGGCCAT
GCTAGAGTCCGCAAAAATCACCAGTCTCTCTCTACAAATCTATCTCTCTCTATTTTTCTCCAGA
```

Figure 8F cont'd

```
ATAATGTGTGAGTAGTTCCCAGATAAGGGAATTAGGGTTCTTATAGGGTTTCGCTCATGTGTT
GAGCATATAAGAAACCCTTAGTATGTATTTGTATTTGTAAAATACTTCTATCAATAAAATTTCT
AATTCCTAAAACCAAAATCCAGTGACCTGCAGGCATGCGACGTCGGGCCCTCTAGAGGATCCC
CAACGACGCGTAGTTTAAACATTTATCCTAGTTTGCGCGCTATATTTTGTTTTCTATCGCGTAT
TAAATGTATAATTGCGGGACTCTAATCAAAAAACCCATCTCATAAATAACGTCATGCATTACA
TGTTAATTATTACATGCTTAACGTAATTCAACAGAAATTATATGATAATCATCGCAAGACCGG
CAACAGGATTCAATCTTAAGAAACTTTATTGCCAAATGTTTGAACGATCTGCTTGACTCTAGCT
AGAGTCCGAACCCCAGAGTCCCGCTCAGGCGGCCGCCACCGCGGTGGAGCTCCAGCTTTTGTT
CCCTTTAGTGAGGGTTAATTCCGAGCTTGGCGTAATCATGGTCATAGCTGTTTCCTGTGTGAAA
TTGTTATCCGCTCACAATTCCACACAACATACGAGCCGGAAGCATAAAGTGTAAAGCCTGGGG
TGCCTAATGAGTGAGCTAACTCACATTAATTGCGTTGCGCTCACTGCCCGCTTTCCAGTCGGG
AAACCTGTCGTGCCAGCTGCATTAATGAATCGGCCAACGCGCGGGGAGAGGCGGTTTGCGTA
TTGGGCGCTCTTCCGCTTCCTCGCTCACTGACTCGCTGCGCTCGGTCGTTCGGCTGCGGCGAGC
GGTATCAGCTCACTCAAAGGCGGTAATACGGTTATCCACAGAATCAGGGGATAACGCAGGAA
AGAACATGAAGGCCTTGACAGGATATATTGGCGGGTAAACTAAGTCGCTGTATGTGTTTGTTT
GAGATCTCATGTGAGCAAAAGGCCAGCAAAAGGCCAGGAACCGTAAAAAGGCCGCGTTGCTG
GCGTTTTTCCATAGGCTCCGCCCCCTGACGAGCATCACAAAAATCGACGCTCAAGTCAGAGG
TGGCGAAACCCGACAGGACTATAAAGATACCAGGCGTTTCCCCCTGGAAGCTCCCTCGTGCGC
TCTCCTGTTCCGACCCTGCCGCTTACCGGATACCTGTCCGCCTTTCTCCCTTCGGGAAGCGTGG
CGCTTTCTCATAGCTCACGCTGTAGGTATCTCAGTTCGGTGTAGGTCGTTCGCTCCAAGCTGGG
CTGTGTGCACGAACCCCCCGTTCAGCCCGACCGCTGCGCCTTATCCGGTAACTATCGTCTTGA
GTCCAACCCGGTAAGACACGACTTATCGCCACTGGCAGCAGCCACTGGTAACAGGATTAGCA
GAGCGAGGTATGTAGGCGGTGCTACAGAGTTCTTGAAGTGGTGGCCTAACTACGGCTACACTA
GAAGAACAGTATTTGGTATCTGCGCTCTGCTGAAGCCAGTTACCTTCGGAAGAAGAGTTGGTA
GCTCTTGATCCGGCAAACAAACCACCGCTGGTAGCGGTGGTTTTTTTGTTTGCAAGCAGCAGA
TTACGCGCAGAAAAAAAGGATCTCAAGAAGATCCTTTGATCTTTTCTACGGGGTCTGACGCTC
AGTGGAACGAAAACTCACGTTAAGGGATTTTGGTCATGAGATTATCAAAAAGGATCTTCACCT
AGATCCTTTTAAATTAAAAATGAAGTTTTAAATCAATCTAAAGTATATATGTGTAACATTGGT
CTAGTGATTAGAAAAACTCATCGAGCATCAAATGAAACTGCAATTTATTCATATCAGGATTAT
CAATACCATATTTTTGAAAAAGCCGTTTCTGTAATGAAGGAGAAAACTCACCGAGGCAGTTCC
ATAGGATGGCAAGATCCTGGTATCGGTCTGCGATTCCGACTCGTCCAACATCAATACAACCTA
TTAATTTCCCCTCGTCAAAAATAAGGTTATCAAGTGAGAAATCACCATGAGTGACGACTGAAT
CCGGTGAGAATGGCAAAAGTTTATGCATTTCTTTCCAGACTTGTTCAACAGGCCAGCCATTAC
GCTCGTCATCAAAATCACTCGCATCAACCAAACCGTTATTCATTCGTGATTGCGCCTGAGCGA
GACGAAATACGCGATCGCTGTTAAAAGGACAATTACAAACAGGAATCGAATGCAACCGGCGC
AGGAACACTGCCAGCGCATCAACAATATTTTCACCTGAATCAGGATATTCTTCTAATACCTGG
AATGCTGTTTTCCCTGGGATCGCAGTGGTGAGTAACCATGCATCATCAGGAGTACGGATAAAA
TGCTTGATGGTCGGAAGAGGCATAAATTCCGTCAGCCAGTTTAGTCTGACCATCTCATCTGTA
ACAACATTGGCAACGCTACCTTTGCCATGTTTCAGAAACAACTCTGGCGCATCGGGCTTCCCA
TACAATCGGTAGATTGTCGCACCTGATTGCCCGACATTATCGCGAGCCCATTTATACCCATAT
AAATCAGCATCCATGTTGGAATTTAATCGCGGCCTTGAGCAAGACGTTTCCCGTTGAATATGG
CTCATAACACCCCTTGTATTACTGTTTATGTAAGCAGACAGTTTTATTGTTCATGATGATATAT
TTTTATCTTGTGCAATGTAACATCAGAGATTTTGAGACACAACGTGGCTTTGTTGAATAAATCG
AACTTTTGCTGAGTTGAAGGATCAGATCACGCATCTTCCCGACAACGCAGACCGTTCCGTGGC
AAAGCAAAAGTTCAAAATCACCAACTGGTCCACCTACAACAAAGCTCTCATCAACCGTGGCTC
CCTCACTTTCTGGCTGGATGATGGGGCGATTCAGGCGATCCCCATCCAACAGCCCGCCGTCGA
GCGGGCTTTTTTATCCCCGGAAGCCTGTGGATAGAGGGTAGTTATCCACGTGAAACCGCTAAT
GCCCCGCAAAGCCTTGATTCACGGGCTTTCCGGCCCGCTCCAAAAACTATCCACGTGAAATC
GCTAATCAGGGTACGTGAAATCGCTAATCGGAGTACGTGAAATCGCTAATAAGGTCACGTGA
AATCGCTAATCAAAAAGGCACGTGAGAACGCTAATAGCCCTTTCAGATCAACAGCTTGCAAA
CACCCCTCGCTCCGGCAAGTAGTTACAGCAAGTAGTATGTTCAATTAGCTTTTCAATTATGAAT
ATATATATCAATTATTGGTCGCCCTTGGCTTGTGGACAATGCGCTACGCGCACCGGCTCCGCC
CGTGGACAACCGCAAGCGGTTGCCCACCGTCGAGCGCCAGCGCCTTTGCCCACAACCCGGCG
GCCGGCCGCAACAGATCGTTTTATAAATTTTTTTTTTGAAAAAGAAAAAGCCCGAAAGGCGG
CAACCTCTCGGGCTTCTGGATTTCCGATCCCCGGAATTAGAGATCTTGGCAGGATATATTGTG
```

Figure 8F cont'd

GTGTAACGTTATCAGCTTGCATGCCGGTCGATCTAGTAACATAGATGACACCGCGCGATAA
TTTATCCTAGTTTGCGCGCTATATTTTGTTTTCTATCGCGTATTAAATGTATAATTGCGGGACTC
TAATCAAAAAACCCATCTCATAAATAACGTCATGCATTACATGTTAATTATTACATGCTTAAC
GTAATTCAACAGAAATTATATGATAATCATCGCAAGACCGGCAACAGGATTCAATCTTAAGA
AACTTTATTGCCAAATGTTTGAACGATCTGCTTGACTCTAGCTAGAGTCCGAACCCCAGAGTC
CCGCTCAGAAGAACTCGTCAAGAAGGCGATAGAAGGCGATGCGCTGCGAATCGGGAGCGGCG
ATACCGTAAAGCACGAGGAAGCGGTCAGCCCATTCGCCGCCAAGCTCTTCAGCAATATCACG
GGTAGCCAACGCTATGTCCTGATAGCGGTCCGCCACACCCAGCCGGCCACAGTCGATGAATCC
AGAAAAGCGGCCATTTTCCACCATGATATTCGGCAAGCAGGCATCGCCCTGGGTCACGACGA
GATCCTCGCCGTCGGGCATCCGCGCCTTGAGCCTGGCGAACAGTTCGGCTGGCGCGAGCCCCT
GATGCTCTTCGTCCAGATCATCCTGATCGACAAGACCGGCTTCCATCCGAGTACGTCCTCGCTC
GATGCGATGTTTCGCTTGGTGGTCGAATGGGCAGGTAGCCGGATCAAGCGTATGCAGCCGCCG
CATTGCATCAGCCATGATGGATACTTTCTCGGCAGGAGCAAGGTGAGATGACAGGAGATCCT
GCCCCGGCACTTCGCCCAATAGCAGCCAGTCCCTTCCCGCTTCAGTGACAACGTCGAGCACAG
CTGCGCAAGGAACGCCCGTCGTGGCCAGCCACGATAGCCGCGCTGCCTCGTCTTGGAGTTC

Figure 8 G
SEQ ID NO: 9
35S Promoter

TCGACTAGAATAGTAAATTGTAATGTTGTTTGTTGTTTGTTTTGTTGTGGTAATTGTTGTAAAA
ATACGGATCGTCCTGCAGTCCTCTCCAAATGAAATGAACTTCCTTATATAGAGGAAGGGTCTT
GCGAAGGATAGTGGGATTGTGCGTCATCCCTTACGTCAGTGGAGATATCACATCAATCCACTT
GCTTTGAAGACGTGGTTGGAACGTCTTCTTTTTCCACGATGCTCCTCGTGGGTGGGGGTCCATC
TTTGGGACCACTGTCGGCAGAGGCATCTTGAACGATAGCCTTTCCTTTATCGCAATGATGGCA
TTTGTAGGTGCCACCTTCCTTTTCTACTGTCCTTTTGATGAAGTGACAGATAGCTGGGCAATGG
AATCCGAGGAGGTTTCCCGATATTACCCTTTGTTGAAAAGTCTCAATAGCCCTTTGGTCTTCTG
AGACTGTATCTTTGATATTCTTGGAGTAGACGAGAGTGTCGTGCTCCACCATGTTGACGAAGA
TTTTCTTCTTGTCATTGAGTCGTAAAAGACTCTGTATGAACTGTTCGCCAGTCTTCACGGCGAG
TTCTGTTAGATCCTCGATCTGAATTTTTGACTCCATGGCCTTTGATTCAGTAGGAACTACTTTCT
TAGAGACTCCAATCTCTATTACTTGCCTTGGTTTATGAAGCAAGCCTTGAATCGTCCATACTGG
AATAGTACTTCTGATCTTGAGAAATATATCTTTCTCTGTGTTCTTGATGCAGTTAGTCCTGAAT
CTTTTGACTGCATCTTTAACCTTCTTGGGAAGGTATTTGATCTCCTGGAGATTATTACTCGGGT
AGATCGTCTTGATGAGACCTGCCGCGTAGGCCTCTCTAACCATCTGTGGGTCAGCATTCTTTCT
GAAATTGAAGAGGCTAATCTTCTCATTATCGGTGGTGAACATGGTATCGTCACCTTCTCCGTC
GAACTTTCTTCCTAGATCGTAGAGATAGAGAAAGTCGTCCATGGTGATCTCCGGGGCAAAGGA
GATCAGCTTGGCTCTAG

Figure 8 H
SEQ ID NO: 10
AlcA promoter

CCGACCTAGGATTGGATGCATGCGGAACCGCACGAGG
GCGGGGCGGAAATTGACACACCACTCCTCTCCACGCAGCCGTTCAAGAGGTACGCGTATAGA
GCCGTATAGAGCAGAGACGGAGCACTTTCTGGTACTGTCCGCACGGGATGTCCGCACGGAGA
GCCACAAACGAGCGGGGCCCCGTACGTGCTCTCCTACCCCAGGATCGCATCCTCGCATAGCTG
AACATCTATATAAGGAAGTTCATTTCATTT
GGAGAGGACACGCTGAAATCACCAGTCTCTCTCTACAAATCTATCTCTCTCGAGCTTTCGCAG
ATCCCGGGGAGTACTC

Figure 8 I
SEQ ID NO: 11
RBC Promoter

AAGCTTGTGGGAACGAGATAAGGGCGAAGTGCGCTAGTAGCCTGCTATTTAAAATATATCCA
CAATTTATAATGTATTTGAAGATTAGTCAATTCGTCCAAAATTCAGGACTAAGTATCTTGAATT
TTTGTATCCTGAATTTTTGGGCTACTAATTTGGAACTCAGGACTTAATGTCCTAAATTTTTGAG
CCGCTAATTTGAAATTCAGGACTAAGTGTTTTGAATTTTTGAACTGCTTATTCGAAATGCAAGA
CTAAGTGACATGAATTTTTGAACTGCTAATTTAAAATTCAGGACATAAGATTTGAATTTTCAA
ACATAATTTTTTAACTTTAGGGCACGATGTCCTGAAGTTTGAATCTTGAGATCTAAACTTCAAG
ATGCAGCGTCTTGAAGTTTGAGTGAACTGGCTAATCTTTAAATACTTGTAAACTGTGGATACA
TTTTTAAATAATATATTTAAAAGCGGCTACCTGGTATCATCTTCACGAGAATTTTCCAAGTTAA
TTGTAAAGGAAATAGTGGTGTTGCATCAAGTTATGGACAATATAAGGAAGCAAACAGTACTC
TAGCTATCAAATTAGTTTCCACTTCTAAACCATGAATATTAGGAAAAACAAGAAACAAAACA
AATATACATAAACAATACGGCTAAAGCCAAGGAAAAGGGACTCTAAAAAAATTAACCAACCT
CAATCACACATTCATATCCTCTTCCTACCCCATCTAGGATGAGATAAGATTACTAGGTCTTACA
CGTGGCACCTCCATTGTGGTGACTAAATGAAGAGTGGCTTAGCTCAAAATATAATTTTCCAAC
CTTTCATGTGTGGATATTAAGTTTTGTGTAGTGAATCAAGAACCACATAATCCAATGGTTAGCT
TTATTCCAAGATGAGGGGGTTGTTGATTTTTGTCCGTCAGATATAGGAAATATGTAAAACCTT
ATCATTATATATAGGGTGGTGGGCAACTATGCAATGACCATATTGGAAGTTAAAGGAAAAGA
GAGAAAGAGAAAT

Figure 8 J
SEQ ID NO: 12
AlcR fragment with required 35s Promotor

CATGGTGGAGCACGACACTCTCGTCTACTCCAAGAATATCAAAGATACAGTCTCAGAAGACC
AAAGGGCTATTGAGACTTTTCAACAAAGGGTAATATCGGGAAACCTCCTCGGATTCCATTGCC
CAGCTATCTGTCACTTCATCAAAAGGACAGTAGAAAAGGAAGGTGGCACCTACAAATGCCAT
CATTGCGATAAAGGAAAGGCTATCGTTCAAGATGCCTCTGCCGACAGTGGTCCCAAAGATGG
ACCCCCACCCACGAGGAGCATCGTGGAAAAAGAAGACGTTCCAACCACGTCTTCAAAGCAAG
TGGATTGATGTGATAACATGGTGGAGCACGACACTCTCGTCTACTCCAAGAATATCAAAGATA
CAGTCTCAGAAGACCAAAGGGCTATTGAGACTTTTCAACAAAGGGTAATATCGGGAAACCTC
CTCGGATTCCATTGCCCAGCTATCTGTCACTTCATCAAAAGGACAGTAGAAAAGGAAGGTGGC
ACCTACAAATGCCATCATTGCGATAAAGGAAAGGCTATCGTTCAAGATGCCTCTGCCGACAGT
GGTCCCAAAGATGGACCCCCACCCACGAGGAGCATCGTGGAAAAAGAAGACGTTCCAACCAC
GTCTTCAAAGCAAGTGGATTGATGTGATATCTCCACTGACGTAAGGGATGACGCACAATCCCA
CTATCCTTCGCAAGACCTTCCTCTATATAAGGAAGTTCATTTCATTTGGAGAGGACACGCTGA
AATCACCAGTCTCTCTCTACAAATCTATCTCTCTCGAGCTTTCGCAGATCCCGGGGAGTACTAT
GTGCTGGAACCCCGCATGCTCCAGGCCTCATTCCCCAGATTTCGACTCCATGGCTGACAGCAT
CCAGACCGCACGTTTTTGGACTTCTGATACCATCTATACAGATATCACTGTCGATATTCTCCTG
CACACAGCATGGCAGATACGCGCCGACGCCAGAATCATAGCTGCGATCCCTGTCGCAAGGGC
AAGCGACGCTGTGATGCCCCGAAACGAGGCCAATGAAAACGGCTGGGTTTCGTGTTCAAATT
GCAAGCGTTGGAACAAGGATTGTACCTTCAATTGGCTCTCATCCCAACGCTCCAAGGCAAAAG
GGGCTGCACCTAGAGCGAGAACAAAGAAAGCCAGGACCGCAACAACCACCAGTGAACCATC
AACTTCAGCTGCAACAATCCCTACACCGGAAAGTGACAATCACGATGCGCCTCCAGTCATAAA
CTCTCACGACGCGCTCCCGAGCTGGACTCAGGGGCTACTCTCCCACCCCGGCGACCTTTTCGA
TTTCAGCCACTCTGCTATTCCCGCAAATGCAGAAGATGCGGCCAACGTGCAGTCAGACGCACC
TTTTCCGTGGGATCTAGCCATCCCCGGTGATTTCAGCATGGGCCAACAGCTCGAGAAACCTCT
CAGTCCGCTCAGTTTTCAAGCAGTCCTTCTTCCGCCCCATAGCCCGAACACGGATGACCTCATT
CGCGAGCTGGAAGAGCAGACTACGGATCCGGACTCGGTTACCGATACTAATAGTGTACAACA
GGTCGCTCAAGATGGATCGCTATGGTCTGATCGGCAGTCGCCGCTACTGCCTGAGAACAGTCT
GTGCATGGCCTCAGACAGCACAGCACGGCGATATGCCCGTTCCACAATGACGAAGAATCTGA
TGCGAATCTACCACGATAGTATGGAGAATGCACTGTCCTGCTGGCTGACAGAGCACAATTGTC

Figure 8J cont'd

CATACTCCGACCAGATCAGCTACCTGCCGCCCAAGCAGCGGGCGGAATGGGGCCCGAACTGG
TCAAACAGGATGTGCATCCGGGTGTGCCGGCTAGATCGCGTATCTACCTCATTACGCGGGCG
GCCCTGAGTGCGGAAGAGGACAAAGCCGCAGCCCGAGCCCTGCATCTGGCGATCGTAGCTTT
TGCGTCGCAATGGACGCAGCATGCGCAGAGGGGGGCTGGGCTAAATGTTCCTGCAGACATAG
CCGCCGATGAGAGGTCCATCCGGAGGAACGCCTGGAATGAAGCACGCCATGCCTTGCAGCAC
ACGACAGGGATTCCATCATTCCGGGTTATATTTGCGAATATCATCTTTTCTCTCACGCAGAGTG
TGCTGGATGATGAGCAGCACGGTATGGGTGCACGTCTAGACAAGCTACTCGAAAATGAC
GGTGCGCCCGTGTTCCTGGAAACCGCGAACCGTCAGCTTTATACATTCCGACATAAGTTTGCA
CGAATGCAACGCCGCGGTAAGGCTTTCAACAGGCTCCCGGGAGGATCTGTCGCATCGACATTC
GCCGGTATTTTCGAGACACCGACGCCGTCGTCTGAAAGCCCACAGCTTGACCCGGTTGTGGCC
AGTGAGGAGCATCGCAGTACATTAAGCCTTATGTTCTGGCTAGGGATCATGTTCGATACACTA
AGCGCTGCAATGTACCAGCGACCACTCGTGGTGTCAGATGAGGATAGCCAGATATCATCGGC
ATCTCCACCAAGGCGCGGCGCTGAAACGCCGATCAACCTAGACTGCTGGGAGCCCCCGAGAC
AGGTCCCGAGCAATCAAGAAAAGAGCGACGTATGGGGCGACCTCTTCCTCCGCACCTCGGAC
TCTCTCCCAGATCACGAATCCCACACACAAATCTCTCAGCCAGCGGCTCGATGGCCCTGCACC
TACGAACAGGCCGCCGCCGCTCTCTCCTCTGCAACGCCCGTCAAAGTCCTCCTCTACCGCCGC
GTCACGCAGCTCCAAACCCTCCTCTATCGCGGCGCCAGCCCTGCCCGCCTTGAAGCGGCCATC
CAGAGAACGCTCTACGTTTATAATCACTGGACAGCGAAGTACCAACCATTTATGCAGGACTGC
GTTGCTAACCACGAGCTCCTCCCTTCGCGCATCCAGTCTTGGTACGTCATTCTAGACGGTCACT
GGCATCTAGCCGCGATGTTGCTAGCGGACGTTTTGGAGAGCATCGACCGCGATTCGTACTCTG
ATATCAACCACATCGACCTTGTAACAAAGCTAAGGCTCGATAATGCACTAGCAGTTAGTGCCC
TTGCGCGCTCTTCACTCCGAGGCCAGGAGCTGGACCCGGGCAAAGCATCTCCGATGTATCGCC
ATTTCCATGATTCTCTGACCGAGGTGGCATTCCTGGTAGAACCGTGGACCGTCGTTCTTATTCA
CTCGTTTGCCAAAGCTGCGTATATCTTGCTGGACTGTTTAGATCTGGACGGCCAAGGAAATGC
ACTAGCGGGGTACCTGCAGCTGCGGCAAAATTGCAACTACTGCATTCGGGCGCTGCAATTTCT
GGGCAGGAAGTCGGATATGGCGGCGCTGGTTGCGAAGGATTTAGAGAGAGGTTTGAATGGGA
AAGTTGACAGCTTTTTGTA

Figure 8 K
SEQ ID NO: 23
Cpn21AS

CACACGTGCCAGATTATGCTCAGGCCGTTTACGGAAAAAATTTCCACAATTGGGATACAAGTT
GCAGATTACAAAGATATAACATAACTAAGAAAGTATAGCCATCACATCTGAAGCTCTGAGGG
CAATGTAGTTGGAACCATCTTTGCCCTTGAAGTCGTTACCAGCATACTTGGAGTAAAGTACTG
TGCTTCCGGTTGATACTGGTAGAGGCGTAATTTTACCTTCCTCGTCTAGGGAACCCGGTCCAAC
TGCTATCACCGTGCCAATAGAAGGCTTCTCTTTGGTAGTCTCGGTTAACAACAACCCTCCAGCT
GTTTTCTCCTCCGCCTCAGCAACCTTAATAAAGACTCGGTCATTCAAAGGTTTGAGATCTTTGA
TGTCCTCTGTCTCAAGAATGCCAACAATATCATCTTCCTTGAGGATAAGATGCTTCACATCATT
GAACTCCACCTCAGTTCCTGCGTATTTGGAGTAGATAATTTGTGCTCCAGTAGGGACAGTGAT
ATCAATTTTGTTCTTCCCAATAGTTCTTCCTTCACCCACGGCAACGACTTCACCTCCTTGAGGT
TTTGATTGAGCAGTGGATGGAAGTAAGATACCACCTAAAGTCTTCTCCTCTGCCTCCTTGATCT
TCACCAAAACTCGATCTCCCAATGGCTTAATTGAAGTATACTTAGGGCAACAACAGAAGCA
GCTTTGACAACCAAACGACGGAACTGGCTCTGTCTAAGGGTCCCTGGTTTCAAAGATGAAAAC
TTGACACTCGAAGCTCTGAGACCATCCAGCGAGGCTAAGCTCCTTGCTGACATAGTCACTGGT
GACGCTGTAAGTTGAGTCGCCGCCATT

Figure 8 L

SEQ ID NO: 2

AATGGCGGCGACTCAACTTACAGCGTCACCAGTGACTATGTCAGCAAGGAGCTTAGCCTCGCT
GGATGGTCTCAGAGCTTCGAGTGTCAAGTTTTCATCTTTGAAACCAGGGACCCTTAGACAGAG
CCAGTTCCGTCGTTTGGTTGTCAAAGCTGCTTCTGTTGTTGCCCCTAAGTATACTTCAATTAAG
CCATTGGGAGATCGAGTTTTGGTGAAGATCAAGGAGGCAGAGGAGAAGACTTTAGGTGGTAT
CTTACTTCCATCCACTGCTCAATCAAAACCTCAAGGAGGTGAAGTCGTTGCCGTGGGTGAAGG
AAGAACTATTGGGAAGAACAAAATTGATATCACTGTCCCTACTGGAGCACAAATTATCTACTC
CAAATACGCAGGAACTGAGGTGGAGTTCAATGATGTGAAGCATCTTATCCTCAAGGAAGATG
ATATTGTTGGCATTCTTGAGACAGAGGACATCAAAGATCTCAAACCTTTGAATGACCGAGTCT
TTATTAAGGTTGCTGAGGCGGAGGAGAAAACAGCTGGAGGGTTGTTGTTAACCGAGACTACC
AAAGAGAAGCCTTCTATTGGCACGGTGATAGCAGTTGGACCGGGTTCCCTAGACGAGGAAGG
TAAAATTACGCCTCTACCAGTATCAACCGGAAGCACAGTACTTTACTCCAAGTATGCTGGTAA
CGACTTCAAGGGCAAAGATGGTTCCAACTACATTGCCCTCAGAGCTTCAGATGTGATGGCTAT
ACTTTCTTAGTTATGTTATATCTTTGTAATCTGCAACTTGTATCCCAATTGTGGAAATTTTTTCC
GTAAACGGCCTGAGCATAATCTGGCACGTGTG

Figure 8M
SEQ ID NO: 28
pGreen0029-RBC

ATTCAGGGCACCGGACAGGTCGGTCTTGACAAAAAGAACCGGGCGCCCCTGCGCTGACAGCC
GGAACACGGCGGCATCAGAGCAGCCGATTGTCTGTTGTGCCCAGTCATAGCCGAATAGCCTCT
CCACCCAAGCGGCCGGAGAACCTGCGTGCAATCCATCTTGTTCAATCATGCCTCGATCGAGTT
GAGAGTGAATATGAGACTCTAATTGGATACCGAGGGGAATTTATGGAACGTCAGTGGAGCAT
TTTTGACAAGAAATATTTGCTAGCTGATAGTGACCTTAGGCGACTTTTGAACGCGCAATAATG
GTTTCTGACGTATGTGCTTAGCTCATTAAACTCCAGAAACCCGCGGCTGAGTGGCTCCTTCAA
CGTTGCGGTTCTGTCAGTTCCAAACGTAAAACGGCTTGTCCCGCGTCATCGGCGGGGTCATA
ACGTGACTCCCTTAATTCTCATGTATCGATAACATTAACGTTTACAATTTCGCGCCATTCGCCA
TTCAGGCTGCGCAACTGTTGGGAAGGGCGATCGGTGCGGGCCTCTTCGCTATTACGCCAGCTG
GCGAAAGGGGGATGTGCTGCAAGGCGATTAAGTTGGGTAACGCCAGGGTTTTCCCAGTCACG
ACGTTGTAAAACGACGGCCAGTGAATTGTAATACGACTCACTATAGGGCGAATTGGGTACCTC
TGCAGATAAGCTTGTGGGAACGAGATAAGGGCGAAGTGCGCTAGTAGCCTGCTATTTAAAAT
ATATCCACAATTTATAATGTATTTGAAGATTAGTCAATTCGTCCAAAATTCAGGACTAAGTAT
CTTGAATTTTTGTATCCTGAATTTTTGGGCTACTAATTTGGAACTCAGGACTTAATGTCCTAAA
TTTTTGAGCCGCTAATTTGAAATTCAGGACTAAGTGTTTTGAATTTTTGAACTGCTTATTCGAA
ATGCAAGACTAAGTGACATGAATTTTTGAACTGCTAATTTAAAATTCAGGACATAAGATTTGA
ATTTTCAAACATAATTTTTTAACTTTAGGGCACGATGTCCTGAAGTTTGAATCTTGAGATCTAA
ACTTCAAGATGCAGCGTCTTGAAGTTTGAGTGAACTGGCTAATCTTTAAATACTTGTAAACTG
TGGATACATTTTTAAATAATATATTTAAAAGCGGCTACCTGGTATCATCTTCACGAGAATTTTC
CAAGTTAATTGTAAAGGAAATAGTGGTGTTGCATCAAGTTATGGACAATATAAGGAAGCAAA
CAGTACTCTAGCTATCAAATTAGTTTCCACTTCTAAACCATGAATATTAGGAAAAACAAGAAA
CAAAACAAATATACATAAACAATACGGCTAAAGCCAAGGAAAAGGGACTCTAAAAAAATTA
ACCAACCTCAATCACACATTCATATCCTCTTCCTACCCCATCTAGGATGAGATAAGATTACTA
GGTCTTACACGTGGCACCTCCATTGTGGTGACTAAATGAAGAGTGGCTTAGCTCAAAATATAA
TTTTCCAACCTTTCATGTGTGGATATTAAGTTTTGTGTAGTGAATCAAGAACCACATAATCCAA
TGGTTAGCTTTATTCCAAGATGAGGGGGTTGTTGATTTTGTCCGTCAGATATAGGAAATATGT
AAAACCTTATCATTATATATAGGGTGGTGGGCAACTATGCAATGACCATATTGGAAGTTAAAG
GAAAAGAGAGAAAGAGAAATCTTTCTGTCTAAGTGTAATTAACTTCTAGATACATGTCTCGAG
CGGCCGCCAGTGTGATGGATATCGAATTCGCCCTTGGATCCTCACTAGTGGATCCGAGCTCAT
CGATAAGCTTGGCGTCGATCGTTCAAACATTTGGCAATAAAGTTTCTTAAGATTGAATCCTGTT
GCCGGTCTTGCGATGATTATCATATAATTTCTGTTGAATTACGTTAAGCATGTAATAATTAACA

Figure 8M cont'd

```
TGTAATGCATGACGTTATTTATGAGATGGGTTTTTATGATTAGAGTCCCGCAATTATACATTTA
ATACGCGATAGAAAACAAAATATAGCGCGCAAACTAGGATAAATTATCGCGCGGTGTCAT
CTATGTTACTAGATCGGGGAATTGATCCCCCCTCGACAGCTTCCCATGGTCCCCGGGGAGGGC
CCCCCCTCGAGGTCGACGGTATCGATAAGCTTGATATCGAATTCCTGCAGCCCGGGGGATCCA
CTAGTTCTAGAGCGGCCGCCACCGCGGTGGAGCTCCAGCTTTTGTTCCCTTTAGTGAGGGTTA
ATTCCGAGCTTGGCGTAATCATGGTCATAGCTGTTTCCTGTGTGAAATTGTTATCCGCTCACAA
TTCCACACAACATACGAGCCGGAAGHCATAAAGTGTAAAGCCTGGGGTGCCTAATGAGTGAG
CTAACTCACATTAATTGCGTTGCGCTCACTGCCCGCTTTCCAGTCGGGAAACCTGTCGTGCCAG
CTGCATTAATGAATCGGCCAACGCGCGGGGAGAGGCGGTTTGCGTATTGGGCGCTCTTCCGCT
TCCTCGCTCACTGACTCGCTGCGCTCGGTCGTTCGGCTGCGGCGAGCGGTATCAGCTCACTCA
AAGGCGGTAATACGGTTATCCACAGAATCAGGGGATAACGCAGGAAAGAACATGAAGGCCTT
GACAGGATATATTGGCGGGTAAACTAAGTCGCTGTATGTGTTTGTTTGAGATCTCATGTGAGC
AAAAGGCCAGCAAAAGGCCAGGAACCGTAAAAAGGCCGCGTTGCTGGCGTTTTTCCATAGGC
TCCGCCCCCTGACGAGCATCACAAAAATCGACGCTCAAGTCAGAGGTGGCGAAACCCGACA
GGACTATAAAGATACCAGGCGTTTCCCCCTGGAAGCTCCCTCGTGCGCTCTCCTGTTCCGACC
CTGCCGCTTACCGGATACCTGTCCGCCTTTCTCCCTTCGGGAAGCGTGGCGCTTTCTCATAGCT
CACGCTGTAGGTATCTCAGTTCGGTGTAGGTCGTTCGCTCCAAGCTGGGCTGTGTGCACGAAC
CCCCCGTTCAGCCCGACCGCTGCGCCTTATCCGGTAACTATCGTCTTGAGTCCAACCCGGTAA
GACACGACTTATCGCCACTGGCAGCAGCCACTGGTAACAGGATTAGCAGAGCGAGGTATGTA
GGCGGTGCTACAGAGTTCTTGAAGTGGTGGCCTAACTACGGCTACACTAGAAGAACAGTATTT
GGTATCTGCGCTCTGCTGAAGCCAGTTACCTTCGGAAGAAGAGTTGGTAGCTCTTGATCCGGC
AAACAAACCACCGCTGGTAGCGGTGGTTTTTTTGTTTGCAAGCAGCAGATTACGCGCAGAAAA
AAAGGATCTCAAGAAGATCCTTTGATCTTTTCTACGGGGTCTGACGCTCAGTGGAACGAAAAC
TCACGTTAAGGGATTTTGGTCATGAGATTATCAAAAAGGATCTTCACCTAGATCCTTTTAAATT
AAAAATGAAGTTTTAAATCAATCTAAAGTATATATGTGTAACATTGGTCTAGTGATTAGAAAA
ACTCATCGAGCATCAAATGAAACTGCAATTTATTCATATCAGGATTATCAATACCATATTTTTG
AAAAAGCCGTTTCTGTAATGAAGGAGAAAACTCACCGAGGCAGTTCCATAGGATGGCAAGAT
CCTGGTATCGGTCTGCGATTCCGACTCGTCCAACATCAATACAACCTATTAATTTCCCCTCGTC
AAAAATAAGGTTATCAAGTGAGAAATCACCATGAGTGACGACTGAATCCGGTGAGAATGGCA
AAAGTTTATGCATTTCTTTCCAGACTTGTTCAACAGGCCAGCCATTACGCTCGTCATCAAAATC
ACTCGCATCAACCAAACCGTTATTCATTCGTGATTGCGCCTGAGCGAGACGAAATACGCGATC
GCTGTTAAAAGGACAATTACAAACAGGAATCGAATGCAACCGGCGCAGGAACACTGCCAGCG
CATCAACAATATTTTCACCTGAATCAGGATATTCTTCTAATACCTGGAATGCTGTTTTCCCTGG
GATCGCAGTGGTGAGTAACCATGCATCATCAGGAGTACGGATAAAATGCTTGATGGTCGGAA
GAGGCATAAATTCCGTCAGCCAGTTTAGTCTGACCATCTCATCTGTAACAACATTGGCAACGC
TACCTTTGCCATGTTTCAGAAACAACTCTGGCGCATCGGGCTTCCCATACAATCGGTAGATTGT
CGCACCTGATTGCCCGACATTATCGCGAGCCCATTTATACCCATATAAATCAGCATCCATGTT
GGAATTTAATCGCGGCCTTGAGCAAGACGTTTCCCGTTGAATATGGCTCATAACACCCCTTGT
ATTACTGTTTATGTAAGCAGACAGTTTTATTGTTCATGATGATATATTTTTATCTTGTGCAATGT
AACATCAGAGATTTTGAGACACAACGTGGCTTTGTTGAATAAATCGAACTTTTGCTGAGTTGA
AGGATCAGATCACGCATCTTCCCGACAACGCAGACCGTTCCGTGGCAAAGCAAAAGTTCAAA
ATCACCAACTGGTCCACCTACAACAAAGCTCTCATCAACCGTGGCTCCCTCACTTTCTGGCTG
GATGATGGGGCGATTCAGGCGATCCCCATCCAACAGCCCGCCGTCGAGCGGGCTTTTTTATCC
CCGGAAGCCTGTGGATAGAGGGTAGTTATCCACGTGAAACCGCTAATGCCCCGCAAAGCCTT
GATTCACGGGGCTTTCCGGCCCGCTCCAAAAACTATCCACGTGAAATCGCTAATCAGGGTACG
TGAAATCGCTAATCGGAGTACGTGAAATCGCTAATAAGGTCACGTGAAATCGCTAATCAAAA
AGGCACGTGAGAACGCTAATAGCCCTTTCAGATCAACAGCTTGCAAACACCCCTCGCTCCGGC
AAGTAGTTACAGCAAGTAGTATGTTCAATTAGCTTTTCAATTATGAATATATATATCAATTATT
GGTCGCCCTTGGCTTGTGGACAATGCGCTACGCGCACCGGCTCCGCCCGTGGACAACCGCAAG
CGGTTGCCCACCGTCGAGCGCCAGCGCCTTTGCCCACAACCCGGCGGCCGGCCGCAACAGATC
GTTTTATAAATTTTTTTTTTTGAAAAAGAAAAAGCCCGAAAGGCGGCAACCTCTCGGGCTTCT
GGATTTCCGATCCCCGGAATTAGAGATCTTGGCAGGATATATTGTGGTGTAACGTTATCAGCT
TGCATGCCGGTCGATCTAGTAACATAGATGACACCGCGCGCGATAATTTATCCTAGTTTGCGC
GCTATATTTTGTTTTCTATCGCGTATTAAATGTATAATTGCGGGACTCTAATCAAAAAACCCAT
```

Figure 8M cont'd

CTCATAAATAACGTCATGCATTACATGTTAATTATTACATGCTTAACGTAATTCAACAGAAATT
ATATGATAATCATCGCAAGACCGGCAACAGGATTCAATCTTAAGAAACTTTATTGCCAAATGT
TTGAACGATCTGCTTGACTCTAGCTAGAGTCCGAACCCCAGAGTCCCGCTCAGAAGAACTCGT
CAAGAAGGCGATAGAAGGCGATGCGCTGCGAATCGGGAGCGGCGATACCGTAAAGCACGAG
GAAGCGGTCAGCCCATTCGCCGCCAAGCTCTTCAGCAATATCACGGGTAGCCAACGCTATGTC
CTGATAGCGGTCCGCCACACCCAGCCGGCCACAGTCGATGAATCCAGAAAAGCGGCCATTTTC
CACCATGATATTCGGCAAGCAGGCATCGCCCTGGGTCACGACGAGATCCTCGCCGTCGGGCAT
CCGCGCCTTGAGCCTGGCGAACAGTTCGGCTGGCGCGAGCCCTGATGCTCTTCGTCCAGATC
ATCCTGATCGACAAGACCGGCTTCCATCCGAGTACGTCCTCGCTCGATGCGATGTTTCGCTTG
GTGGTCGAATGGGCAGGTAGCCGGATCAAGCGTATGCAGCCGCCGCATTGCATCAGCCATGA
TGGATACTTTCTCGGCAGGAGCAAGGTGAGATGACAGGAGATCCTGCCCCGGCACTTCGCCCA
ATAGCAGCCAGTCCCTTCCCGCTTCAGTGACAACGTCGAGCACAGCTGCGCAAGGAACGCCC
GTCGTGGCCAGCCACGATAGCCGCGCTGCCTCGTCTTGGAGTTC

Figure 8N
SEQ ID NO :29
pUC57-RBC

TATGGGGTACCTCTGCAGATAAGCTTGTGGGAACGAGATAAGGGCGAAGTGCGCTAGTAGCC
TGCTATTTAAAATATATCCACAATTTATAATGTATTTGAAGATTAGTCAATTCGTCCAAAATTC
AGGACTAAGTATCTTGAATTTTTGTATCCTGAATTTTTGGGCTACTAATTTGGAACTCAGGACT
TAATGTCCTAAATTTTTGAGCCGCTAATTTGAAATTCAGGACTAAGTGTTTTGAATTTTTGAAC
TGCTTATTCGAAATGCAAGACTAAGTGACATGAATTTTTGAACTGCTAATTTAAAATTCAGGA
CATAAGATTTGAATTTTCAAACATAATTTTTTAACTTTAGGGCACGATGTCCTGAAGTTTGAAT
CTTGAGATCTAAACTTCAAGATGCAGCGTCTTGAAGTTTGAGTGAACTGGCTAATCTTTAAAT
ACTTGTAAACTGTGGATACATTTTTAAATAATATATTTAAAAGCGGCTACCTGGTATCATCTTC
ACGAGAATTTTCCAAGTTAATTGTAAAGGAAATAGTGGTGTTGCATCAAGTTATGGACAATAT
AAGGAAGCAAACAGTACTCTAGCTATCAAATTAGTTTCCACTTCTAAACCATGAATATTAGGA
AAAACAAGAAACAAAACAAATATACATAAACAATACGGCTAAAGCCAAGGAAAAGGGACTC
TAAAAAAATTAACCAACCTCAATCACACATTCATATCCTCTTCCTACCCCATCTAGGATGAGA
TAAGATTACTAGGTCTTACACGTGGCACCTCCATTGTGGTGACTAAATGAAGAGTGGCTTAGC
TCAAAATATAATTTTCCAACCTTTCATGTGTGGATATTAAGTTTTGTGTAGTGAATCAAGAACC
ACATAATCCAATGGTTAGCTTTATTCCAAGATGAGGGGGTTGTTGATTTTTGTCCGTCAGATAT
AGGAAATATGTAAAACCTTATCATTATATAGGGTGGTGGGCAACTATGCAATGACCATATT
GGAAGTTAAAGGAAAAGAGAGAAAGAGAAATCTTTCTGTCTAAGTGTAATTAACTTCTAGAT
ACATGTCTCGAGCGGCCGCCAGTGTGATGGATATCGAATTCGCCCTTGGATCCTCACTAGTGG
ATCCGAGCTCATCGATAAGCTTGGCGTCGATCGTTCAAACATTTGGCAATAAAGTTTCTTAAG
ATTGAATCCTGTTGCCGGTCTTGCGATGATTATCATATAATTTCTGTTGAATTACGTTAAGCAT
GTAATAATTAACATGTAATGCATGACGTTATTTATGAGATGGGTTTTTATGATTAGAGTCCCGC
AATTATACATTTAATACGCGATAGAAAACAAAATATAGCGCGCAAACTAGGATAAATTATCG
CGCGCGGTGTCATCTATGTTACTAGATCGGGGAATTGATCCCCCTCGACAGCTTCCCATGGT
CCCCGGGGAGGGCCCGGCATGCAAGCTTGGCGTAATCATGGTCATAGCTGTTTCCTGTGTGAA
ATTGTTATCCGCTCACAATTCCACACAACATACGAGCCGGAAGCATAAAGTGTAAAGCCTGGG
GTGCCTAATGAGTGAGCTAACTCACATTAATTGCGTTGCGCTCACTGCCCGCTTTCCAGTCGG
GAAACCTGTCGTGCCAGCTGCATTAATGAATCGGCCAACGCGCGGGGAGAGGCGGTTTGCGT
ATTGGGCGCTCTTCCGCTTCCTCGCTCACTGACTCGCTGCGCTCGGTCGTTCGGCTGCGGCGAG
CGGTATCAGCTCACTCAAAGGCGGTAATACGGTTATCCACAGAATCAGGGGATAACGCAGGA
AAGAACATGTGAGCAAAAGGCCAGCAAAAGGCCAGGAACCGTAAAAAGGCCGCGTTGCTGG
CGTTTTTCCATAGGCTCCGCCCCCCTGACGAGCATCACAAAAATCGACGCTCAAGTCAGAGGT
GGCGAAACCCGACAGGACTATAAAGATACCAGGCGTTTCCCCCTGGAAGCTCCCTCGTGCGCT
CTCCTGTTCCGACCCTGCCGCTTACCGGATACCTGTCCGCCTTTCTCCCTTCGGGAAGCGTGGC
GCTTTCTCATAGCTCACGCTGTAGGTATCTCAGTTCGGTGTAGGTCGTTCGCTCCAAGCTGGGC
TGTGTGCACGAACCCCCCGTTCAGCCCGACCGCTGCGCCTTATCCGGTAACTATCGTCTTGAGT
CCAACCCGGTAAGACACGACTTATCGCCACTGGCAGCAGCCACTGGTAACAGGATTAGCAGA

Figure 8N cont'd

```
GCGAGGTATGTAGGCGGTGCTACAGAGTTCTTGAAGTGGTGGCCTAACTACGGCTACACTAGA
AGAACAGTATTTGGTATCTGCGCTCTGCTGAAGCCAGTTACCTTCGGAAAAAGAGTTGGTAGC
TCTTGATCCGGCAAACAAACCACCGCTGGTAGCGGTGGTTTTTTTGTTTGCAAGCAGCAGATT
ACGCGCAGAAAAAAAGGATCTCAAGAAGATCCTTTGATCTTTTCTACGGGGTCTGACGCTCAG
TGGAACGAAAACTCACGTTAAGGGATTTTGGTCATGAGATTATCAAAAAGGATCTTCACCTAG
ATCCTTTTAAATTAAAAATGAAGTTTTAAATCAATCTAAAGTATATATGAGTAAACTTGGTCT
GACAGTTACCAATGCTTAATCAGTGAGGCACCTATCTCAGCGATCTGTCTATTTCGTTCATCCA
TAGTTGCCTGACTCCCCGTCGTGTAGATAACTACGATACGGGAGGGCTTACCATCTGGCCCCA
GTGCTGCAATGATACCGCGAGACCCACGCTCACCGGCTCCAGATTTATCAGCAATAAACCAGC
CAGCCGGAAGGGCCGAGCGCAGAAGTGGTCCTGCAACTTTATCCGCCTCCATCCAGTCTATTA
ATTGTTGCCGGGAAGCTAGAGTAAGTAGTTCGCCAGTTAATAGTTTGCGCAACGTTGTTGCCA
TTGCTACAGGCATCGTGGTGTCACGCTCGTCGTTTGGTATGGCTTCATTCAGCTCCGGTTCCCA
ACGATCAAGGCGAGTTACATGATCCCCATGTTGTGCAAAAAAGCGGTTAGCTCCTTCGGTCC
TCCGATCGTTGTCAGAAGTAAGTTGGCCGCAGTGTTATCACTCATGGTTATGGCAGCACTGCA
TAATTCTCTTACTGTCATGCCATCCGTAAGATGCTTTTCTGTGACTGGTGAGTACTCAACCAAG
TCATTCTGAGAATAGTGTATGCGGCGACCGAGTTGCTCTTGCCCGGCGTCAATACGGGATAAT
ACCGCGCCACATAGCAGAACTTTAAAAGTGCTCATCATTGGAAAACGTTCTTCGGGGCGAAA
ACTCTCAAGGATCTTACCGCTGTTGAGATCCAGTTCGATGTAACCCACTCGTGCACCCAACTG
ATCTTCAGCATCTTTTACTTTCACCAGCGTTTCTGGGTGAGCAAAAACAGGAAGGCAAAATGC
CGCAAAAAAGGGAATAAGGGCGACACGGAAATGTTGAATACTCATACTCTTCCTTTTTCAATA
TTATTGAAGCATTTATCAGGGTTATTGTCTCATGAGCGGATACATATTTGAATGTATTTAGAAA
AATAAACAAATAGGGGTTCCGCGCACATTTCCCCGAAAAGTGCCACCTGACGTCTAAGAAAC
CATTATTATCATGACATTAACCTATAAAAATAGGCGTATCACGAGGCCCTTTCGTCTCGCGCG
TTTCGGTGATGACGGTGAAAACCTCTGACACATGCAGCTCCCGGAGACGGTCACAGCTTGTCT
GTAAGCGGATGCCGGGAGCAGACAAGCCCGTCAGGGCGCGTCAGCGGGTGTTGGCGGGTGTC
GGGGCTGGCTTAACTATGCGGCATCAGAGCAGATTGTACTGAGAGTGCACCA
```

VARIEGATION IN PLANTS

FIELD OF INVENTION

The present invention relates to variegation in plants, and to methods of selecting plants based on this trait.

BACKGROUND OF THE INVENTION

Variegation in plants is defined as the normal green portion of the plant leaf being replaced by white, cream, yellow, or occasionally other colors, which may be in the form of blotches or stripes. The variegations can occur on the edge of the leaves (marginate variegation), or in the center of the leaf (medio variegation). Due to ornamental nature of variegated plants, these plants are desired by gardeners.

Variegations have been induced in plants by a variety of methods including the use of transposable elements (for example Itoh et al., 2002, Plant Cell Physiol. 43(5):578-8), plant transformation with variegated and distorted leaf (vdl) gene, located in the nucleus (Wang et al., 2000, Plant Cell. 12(11):2129-42), antisense glutamate 1-semialdehyde aminotransferase transformation, inhibiting chlorophyll synthesis with partial or complete suppression of the GSA-AT leading to severe plant damage (Hofgen et al., 1994, Proc Natl Acad Sci USA., 91:1726-1730), or spontaneous mutation in the nuclear genes that controlled organelle proteins or mutations in organelle genes (reviewed in Aluru et al., 2006, J. ExpBot. 57:1871-1881. Apuya et al., (2001, Plant Physiol. 126, 717-730) report that a T-DNA mutation in the chaperonin-60α gene (Cpn60) of Arabidopsis results in a defect in embryo development, causing developmental arrest before the heart stage.

Leaf bleaching, along with other abnormal phenotypes such as stunted growth, delayed flowering, reduced root development and the like have been observed in transgenic tobacco plants that constitutively express Arabidopsis Cpn60β transcripts in sense and antisense orientation (Zabaleta, E, et al. 1994, Plant Journal, Vol. 6, pp. 425-432).

Chaperonins are multi-subunit double-ring oligomeric proteins found in bacteria, mitochondria, and plastids. Chaperonins are abundant constitutive proteins that increase in amount after stresses, such as heat shock, bacterial infection of macrophages, and an increase in the cellular content of unfolded proteins.

Higher plant chloroplasts contain a 21-kDa protein, chaperonin 21 (Cpn21) (Hirohashi T. et al, Biochem Biophys Acta. 1999 1429(2):512-5). The chloroplast Cpn21 polypeptide consists of two Cpn10-like domains fused together in tandem. The cDNA sequence of the Cpn21 (AtCpn21) precursor protein from Arabidopsis thaliana is known, and the deduced amino acid sequence of the AtCpn21 precursor protein, 253 amino acids long, shows 61% identity with the spinach Cpn21 protein. The AtCpn21 precursor protein contains a typical chloroplast transit peptide of 51 amino acids at its amino terminus and two Cpn10-like domains, with these two domains exhibiting 46% sequence identity. The predicted, mature polypeptide of AtCpn21 was expressed in Escherichia coli as a soluble 21-kDa protein. Gel-filtration and chemical cross-linking analyses showed that the recombinant mature AtCpn21 protein forms a stable homo-oligomer composed of three or four polypeptides.

Hanania et al., 2007 (Transgenic Res. 16 :515-525) disclosed that Cpn21 was differentially disclosed in seeded and seedless grapes, and may have a role in seed abortion in some plants.

Sjogren et al., (2004, Plant Physiol, 136: 4114-4126), disclose Arabidopsis clpC1 T-DNA insertion mutants that lack on average 65% content of a stromal molecular chaperone (ClpC). Mutants display a retarded-growth phenotype, leaves with a homogenous chlorotic appearance throughout all developmental stages. Photosynthetic performance was impaired in knockout lines, with relatively fewer photosystem I and photosystem II complexes, but no changes in ATPase and RuBisCO content.

SUMMARY OF THE INVENTION

The present invention relates to variegation in plants, and to methods of selecting plants based on this trait.

It is an object of the invention to provide an improved variegated plant.

According to the present invention there is provided a variegated plant comprising a nucleic acid operatively linked to a regulatory region, wherein the nucleic acid disrupts the expression of a chaperonin. The chaperonin may be chaperonin 21 (Cpn21). The nucleic acid may be an antisense sequence of Cpn21, a nucleic acid that hybridizes under stringent conditions with the complement of antisense Cpn21 in vitro, or an RNAi that disrupts the expression of Cpn21. Furthermore, the regulatory region may be an inducible regulatory region, a tissue specific regulatory region, a developmental regulatory region, or a constitutive regulatory region.

The present invention also provides a method (A) of producing a variegated plant comprising, i) providing the plant comprising a nucleic acid operatively linked to a regulatory region, the nucleic acid disrupts the expression of Cpn21, and ii) growing the plant under conditions that results in the expression of the nucleic acid, thereby producing the variegated plant.

Preferably, the nucleic acid in the step of providing is an antisense Cpn21, a nucleic acid that hybridizes under stringent conditions with the complement of antisense Cpn21 in vitro, or an RNAi that disrupts the expression of Cpn21. Furthermore, the regulatory region may be an inducible regulatory region, a tissue specific regulatory region, a developmental regulatory region, or a constitutive regulatory region. The tissue specific regulatory region may be a RuBisCO promoter, or may be a vein-specific promoter. The constitutive regulatory region may comprise a Cauliflower Mosaic Virus 35S (CaMV 35S, or 35S) promoter sequence. The inducible regulatory region may comprise an AlcR sequence and an AlcA promoter.

The present invention also pertains to a method (B) of selecting a plant comprising a nucleic acid of interest comprising, i) providing the plant comprising a first nucleic acid operatively linked to a first regulatory region, the first nucleic acid disrupts the expression of Cpn21, and a second nucleic acid encoding a protein of interest and operatively linked to a second regulatory region, ii) growing the plant under conditions that result in the expression of the first and second nucleic acids, and iii) selecting plants that display a variegated phenotype.

The first nucleic acid in the step of providing may be an antisense Cpn21, a nucleic acid that hybridizes under stringent conditions with the complement of antisense Cpn21 in vitro, or an RNAi that disrupts the expression of Cpn21. Furthermore, the regulatory region may be an inducible regulatory region, a tissue specific regulatory region, a developmental regulatory region, or a constitutive regulatory region.

The second nucleic acid sequence encoding a protein of interest, may include any nucleic acid, for example, but not limited to, a nucleic acid sequence that encodes a pharmaceutically active protein, for example growth factors, growth regulators, antibodies, antigens, their derivatives useful for immunization or vaccination and the like, interleukins, insulin, G-CSF, GM-CSF, hPG-CSF, M-CSF or combinations thereof, interferons, for example, interferon-alpha, interferon-beta, interferon-gamma, blood clotting factors, for example, Factor VIII, Factor IX, or tPA or combinations thereof. The second nucleic acid sequence may also encode an industrial enzyme, a protein supplement, a nutraceutical, or a value-added product for feed, food, or both feed and food use. Examples of such proteins include, but are not limited to proteases, oxidases, phytases, chitinases, invertases, lipases, cellulases, xylanases, enzymes involved in oil biosynthesis etc.

The plants produced using the methods defined above exhibited variegated leaves. The methods as described herein may be used to produce plants with variegated leaves for ornamental purposes, or the occurrence of leaf variegation may be used to assist in plant selection, where leaf variegation is trait that is used as a selectable marker to indicate that transformation of a plant occurred. The methods of the present invention can be used within any plant including crop plants, ornamental plants, forage plants and the like, for example but not limited to *Nicotiana, Arabidopsis*, Canola, Flax, Hemp, *Brachypodium, Oryza, Brassica napus, Petunia* spp., *Cyclamen spp, Begonia* spp., *Azalea* spp, and *Spatifilium* spp., *Artemisia* spp., *Polar, Rosa* spp., Rose, *Musa* spp (e.g. Banana), *Coffea Arabica, Maize, Glycine* spp. (e.g. Soybean), and the like.

The present invention further provides a nucleic acid construct comprising a nucleic acid operatively linked to a regulatory region, wherein the nucleic acid disrupts the expression of Cpn21. The nucleic acid may be an antisense Cpn21, a nucleic acid that hybridizes under stringent conditions with the complement of antisense Cpn21 in vitro, or an RNAi that disrupts the expression of Cpn21. The regulatory region may be an inducible regulatory region, a tissue specific regulatory region, a developmental regulatory region, or a constitutive regulatory region.

The present invention also provides a nucleic acid construct comprising a first nucleic acid operatively linked to a first regulatory region, the first nucleic acid disrupts the expression of Cpn21, and a second nucleic acid encoding a protein of interest. The first nucleic acid may be an antisense Cpn21, a nucleic acid that hybridizes under stringent conditions with the complement of antisense Cpn21 in vitro, or an RNAi that disrupts the expression of Cpn21. The regulatory region may be an inducible regulatory region, a tissue specific regulatory region, a developmental regulatory region, or a constitutive regulatory region. The first regulatory region may comprise an AlcR sequence, and the second regulatory region may comprise an AlcA promoter.

The present invention also includes a vector comprising the nucleic acid construct of the present invention.

Genetically transformed plants expressing antisense chaperonin 21 exhibit a strong tendency to variegation of the leaves and flowers. An advantage of such a system is that the transformed plants and their progeny are free of heterologous nucleic acid sequences. The plants and methods described herein may be used to produce variegated plants for commercial use, including crop plants of for use within the ornamental market. Furthermore, the variegated phenotype obtained in plants using the methods described herein, may be used as a selectable marker. For example, variegated leaves may provide a visual criteria for selecting a plant encoding a protein of interest.

Linking the visual marker to a nucleic acid of interest may also be useful for identifying and segregating, or for the identity preservation of industrial or other genetically modified crops that express this trait. Tissue specific variegation (vein, leaf tip, stem etc), may be used so that the marker is expressed in desired parts of the plant to create different patterns in the same plant species and thus identifying and distinguish different genetically modified traits in the plant.

This summary of the invention does not necessarily describe all features of the invention. Other aspects and features of the present invention will become apparent to those of ordinary skill in the art upon review of the following description of specific embodiments of the invention.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

These and other features of the invention will become more apparent from the following description in which reference is made to the appended drawings wherein:

FIG. 8A: SEQ ID NO: 1—sequence encoding *A. thaliana* cpn21; FIG. 8B: SEQ ID NO: 4—Cpn21 antisense 35S; FIG. 8C: SEQ ID NO: 5—Cpn21 RNAi fragment with intron; FIG. 8D: SEQ ID NO: 6—Cpn21RNAi RBC; FIG. 8E: SEQ ID NO: 7—Cpn21 RNAiRBC; FIG. 8F: SEQ ID NO: 8—AlcR Cpn21 RNAi Sequence; FIG. 8G: SEQ ID NO: 935S promoter; FIG. 8H: SEQ ID NO: 10—AlcA promoter (nucleotides 1-232) with minimal; FIG. 8I: SEQ ID NO: 11—*N. tabacum* RuBisCO (RBC) promoter sequence; FIG. 8J: SEQ ID NO: 12—AlcR fragment with minimal 35S promoter sequence; FIG. 8K: SEQ ID NO: 23 Cpn21 Antisense; FIG. 8L: PCR—amplified fragment of *A. thaliana* Cpn21 (SEQ ID NO: 2); FIG. 8M: SEQ ID NO: 28—pGreen0029-RBC construct; FIG. 8N: SEQ ID NO: 29 pUC57-RBC construct. SEQ ID NO: 4—nucleotides 103-866 comprise an Acpn21 antisense sequence; nucleotides 904-1156 comprise a NOS terminator sequence; nucleotides 10232-10648 comprise a 35S promoter sequence. SEQ ID NO: 5—nucleotides 1-427 comprise ACpn RNAi fragment 1; nucleotides 938-2017 comprise an intron of the ACpn RNAi construct; nucleotides 2156-2627 comprise ACpn RNAi fragment 2. SEQ ID NO: 6—nucleotides 8140-9175 comprise a 35 S promoter sequence; nucleotides 9324-9795 comprise ACpn RNAi fragment 1; nucleotides 9934-11013 comprise an intron of the ACpn RNAi construct; nucleotides 11479-11948 comprise ACpn RNAi fragment 2. SEQ ID NO: 7—nucleotides 2-1026, RBC promoter; nucleotides 1280-1747 comprise ACpnRNAi fragment 1; nucleotides 1839-3193 comprise an intron of the ACpnRNAi construct; nucleotides 3349-3816 comprise ACpnRNAi fragment 2. SEQ ID NO: 8—nucleotides 717-1502 comprise a 35 S promoter sequence; nucleotides 1529-4123 comprise an AlcR sequence; nucleotides 4130-4388 comprise a NOS terminator sequence; nucleotides 4389-4406 comprise an AICA promoter sequence; nucleotides 5058-5525 comprise ACpnRNAi fragment 1; nucleotides 5617-6971 comprise an intron of the ACpnRNAi construct; nucleotides 7127-7594 comprise ACpnRNAi fragment 2.

DETAILED DESCRIPTION

Figure 1:
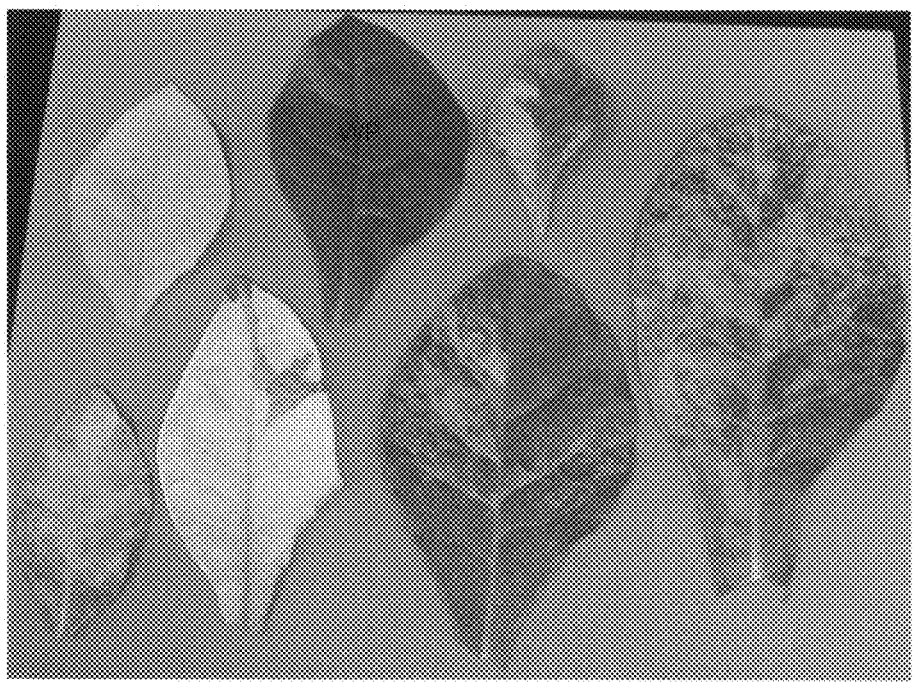
FIG. 1 shows patterns of variegated leaves from tobacco plants, transformed with Cpn21RNAi 35S. WP—wild type plant (non transformed)—top row, middle.
Figure 2:
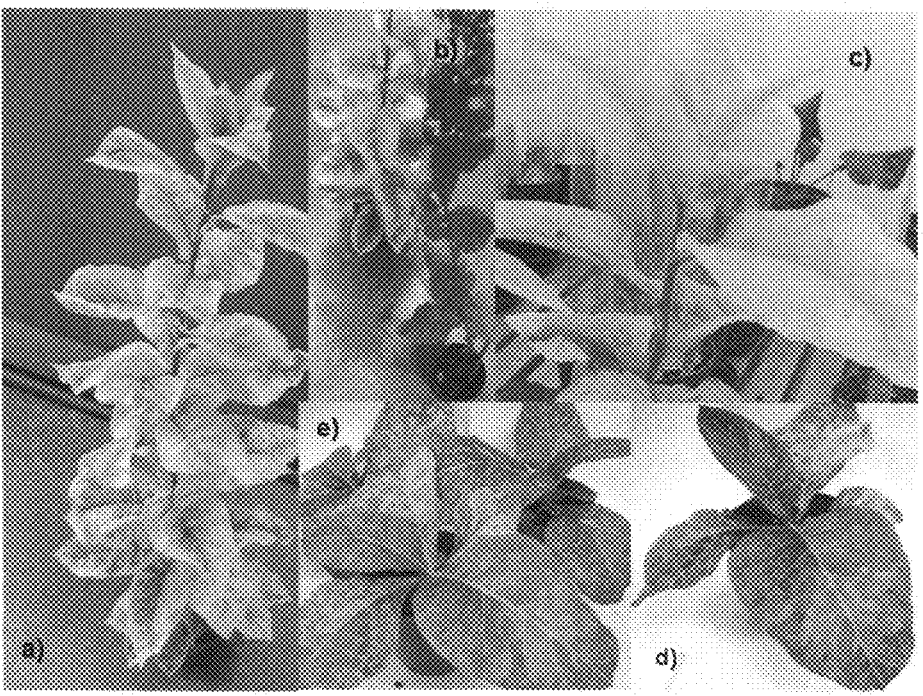
FIG. 2A-E shows T1 tobacco plants expressing Cpn21RNAi-35S constructs. A range of variegation pattern and color intensity is shown in plants. A control plant is shown in the right hand side of FIG. 2B.

The present invention relates to variegation in plants, and to methods of selecting plants based on this trait.

The present invention provides a variegated plant comprising a nucleic acid operatively linked to a regulatory region, wherein the nucleic acid disrupts the expression of chaperonin 21 (Cpn21), or a functional homologue of Cpn21, for example Cpn10. The nucleic acid that disrupts the expression of Cpn21 or a functional homologue of Cpn21, may include but is not limited to, an antisense sequence of Cpn21 or a functional homologue of Cpn21, a nucleic acid that hybridizes under stringent conditions with the complement of antisense Cpn21 or a functional homologue of Cpn21, in vitro, or an RNAi that disrupts the expression of Cpn21 or a functional homologue of Cpn21. The regulatory region may be an inducible regulatory region, a tissue specific regulatory region, a developmental regulatory region, or a constitutive regulatory region.

The Cpn21 sequence may comprise SEQ ID NO: 1, or a fragment of SEQ ID NO: 1 that exhibits Cpn21 activity. SEQ ID NO: 1 corresponds to an *Arabidopsis* chaperonin 21 (cpn21, Acpn21) sequence (NCBI GenBank Accession No. AF428366.1 gi:16226910 *Arabidopsis thaliana* AT5g20720/T1M15_120 mRNA). A fragment of SEQ ID NO. 1 may comprise nucleotides 77-842 of SEQ ID NO: 1. However, the chaperonin sequence may also comprise, for example, *Vitis vinifera* cpn21 (NCBI GenBank Accession No. AY680699), spinach Cpn21 (Baneyz et al. 1995, JBC 270:10695-10702). Furthermore, Cpn21 polypeptide consists of two Cpn10-like domains fused together in tandem, and Cpn21 is considered a functional homologue of Cpn10 (accession number: AF059037; Bertsch U., et al., 1992, PNAS 89:8696-8700; Hirohashi T., et al., 1999, Biochem Biophys Acta 1429:512-515), therefore, the chaperonin sequence of the present invention may also include spinach chaperonin cpn10 (NCBI GenBank Accession No. M87646), *Helicosporidium* sp. ex *Simulium jonesii* cpn10 (NCBI GenBank Accession No. AY596494), or RbcX (Emlyn-Jones et al., 2006 Plant & Cell Physiology 47:1630-1640), or other functional homologue of Cpn21. Other examples of chaperonins, from both prokaryotes and eukaryotes (including plants) may also be found in cpndb-A chaperonin database (for example at URL: cpndb.cbr.nrc.ca/; Hill et al 2004. Genome Research 14:1669-1657, herein incorporated by reference). Chaperonin 21 may be indicated by the abbreviation "cpn21" or "Cpn21".

The method as described herein involves the use of a nucleic acid sequence to disrupt or reduce or eliminates the expression of Cpn21, or a functional homologue of Cpn21, for example Cpn10. This may be achieved, for example but not limited to, by using a silencing nucleic acid as described below. An example of a silencing nucleic acid includes, but is not limited to, an antisense Cpn21, or a functional homologue of Cpn21, sequence, a nucleic acid that hybridizes under stringent conditions with the complement of an antisense Cpn21, or a functional homologue of Cpn21, sequence in vitro, or an RNAi that disrupts expression of Cpn21, or a functional homologue of Cpn21.

Examples of silencing nucleic acids include those comprising a sequence according to: a reverse-complement of SEQ ID NO: 1, 2, or a fragment thereof, SEQ ID NO: 4 or a fragment thereof, SEQ ID NO: 5 or a fragment thereof, SEQ ID NO: 23 or a fragment thereof, nucleotides 2078-2518 of SEQ ID NO: 5, or the reverse complement of nucleotides 223-663 of SEQ ID NO: 2. Sequences encoding Cpn10 may also be used as Cpn10 may be considered a fragment of cpn21 (Bertsch U., et al., 1992, PNAS 89:8696-8700; Hirohashi T., et. al., 1999, Biochem Biophys Acta 1429:512-515).

The regulatory region used in the method and construct described above may be a constitutive regulatory region, an inducible regulatory region, a tissue specific regulatory region, or a developmental regulatory region.

The present invention therefore provides a method for reducing the level of Cpn21 in a plant or a tissue within the plant comprising, i) introducing a nucleic acid sequence into a plant, the nucleic acid sequence comprising a regulatory region operatively associated with a silencing nucleotide sequence, wherein expression of the silencing nucleotide sequence reduces or eliminates the expression of Cpn21, and ii) expressing the silencing nucleotide sequence within the plant or the tissue within the plant. The amount of the Cpn21 may be determined by comparing the level of Cpn21 expression in the plant, or a tissue of the plant, with a level of Cpn21 expression in a second plant, or the tissue from the second plant, that does not express the silencing nucleic acid sequence. The amount of Cpn21 may be determined using standard techniques including northern analysis, western analysis, SDS-PAGE and the like.

The present invention further provides a method for producing a variegated plant, comprising, i) introducing a silencing nucleic acid sequence into the plant, the silencing nucleic acid sequence comprising a regulatory region operatively associated with the silencing nucleic acid sequence. The silencing nucleic acid sequence may comprise a reverse compliment of SEQ ID NO's: 1 or 2, a fragment of a reverse compliment of SEQ ID NO: 1, a sequence that hybridizes to the complement of the antisense of SEQ ID NO's: 1 or 2 or a sequence that hybridizes to a fragment of the complement of the antisense of SEQ ID NO: 1, and ii) growing the plant.

Other silencing nucleic acids may be used in the method above, including SEQ ID NO's: 4, 5 or 23, or fragment thereof, nucleotides 2078-2518 of SEQ ID NO: 5, or the reverse complement of nucleotides 223-663 of SEQ ID NO: 2. Sequences encoding Cpn10 may also be used.

The regulatory region may be a constitutive regulatory region, an inducible regulatory region, a tissue specific regulatory region, or a developmental regulatory region. If an inducible regulatory region is used, then the method further includes a step of subjecting the plant to a chemical agent or environmental condition that induces the regulatory region and results in expression of the silencing nucleic acid.

In embodiments where chaperonin expression is disrupted, the level of chaperonin expression may be reduced by about 10% to about 100%, or any amount therebetween, when compared to the level of chaperonin expression obtained from a second plant that does not express the silencing nucleotide sequence. For example, Cpn21 expression may be reduced by from about 10% to about 60% or any amount therebetween, about 10% to about 50% or any amount therebetween, about 10% to about 40% or any amount therebetween, or from about 10% to about 30%, or any amount therebetween, or about 10% to about 20% or any amount therebetween.

By the term "expression" it is meant the production of a functional RNA, protein or both, from a nucleic acid molecule.

A "silencing nucleotide sequence" or "silencing nucleic acid sequence" refers to a sequence that when transcribed results in disrupting, reducing or eliminating expression of a target sequence. A silencing nucleotide sequence may encode for example, but not limited to, an antisense nucleotide, an RNAi, or an siRNA.

By "reduction of gene expression" or "reduction of expression" "disruption of expression" or "elimination of expression", it is meant a decrease in the level of mRNA, protein, or both mRNA and protein, encoded by a nucleic acid sequence. Expression may be reduced by from 10 to about 100%, or any amount therebetween, for example, from about 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74 m 76 m 78 m 80, 82, 84, 86, 88, 90, 92, 94, 96, 98, and 100%, or any amount therebetween. Reduction of expression may arise as a result of the lack of production of full length RNA, for example mRNA, or through the expression of a silencing nucleic acid sequence, and result in cleaving mRNA, for example with a ribozyme (e.g. see Methods in Molecular Biology, vol 74 *Ribozyme Protocols*, P. C. Turner, ed, 1997, Humana Press), siRNA, or RNAi (e.g. see *Gene Silencing by RNA Interference, Technology and Application*, M. Sohail ed, 2005, CRC Press), or otherwise reducing the half-life of RNA, using antisense (e.g. see *Antisense Technology, A Practical Approach*, C. Lichtenstien and W. Nellen eds., 1997, Oxford University Press), ribozyme, siRNA, or RNAi techniques, or other related methods known in the art.

Antisense nucleic acid molecules interact with complementary strands of nucleotide sequences and when present, may modifying the expression of a target nucleic acid. An antisense nucleic acid may be DNA or RNA and may be delivered as a composition, or transcribed in vivo or in situ from a template nucleic acid, a vector or other construct such as an artificial chromosome, or a transgenic sequence introduced into the genome of the host cell or organism. Antisense nucleic acids may be of varying length from a few tens of nucleotides, to several hundred nucleotides and may comprise antisense sequences that may interact with one, or more than one mRNA.

An antisense nucleic acid may be transcribed from a template nucleic acid, a plasmid or other genetic construct as a single RNA strand that self-anneals to form a hairpin-loop structure. The transcribed RNA strand may comprise two palindromic sequences that are capable of annealing to form a double-strand, separated by a loop, or unpaired section of RNA. The double stranded region may be from about 15 base pairs to several hundred base pairs in length, or any length therebetween, and, for example, may result in the formation of short double-stranded fragments (siRNA) when processed by DICER or RISC-like enzymes or enzyme complexes present in the plant. The short double stranded fragments may include, for example, but not limited to, 21-mers, with a 19 base pair double stranded portion and a two base overhang at the 3' end, as is generally known in the art.

Examples of an antisense sequence of SEQ ID NO: 1 include SEQ ID NO: 23, or a fragment thereof, nucleotides 2078-2518 of SEQ ID NO: 5 or a fragment thereof, or the reverse complement of nucleotides 223-663 of SEQ ID NO: 2, or a fragment thereof, the reverse complement of SEQ ID NO: 1, or a fragment thereof.

By "operatively linked" it is meant that the particular sequences interact either directly or indirectly to carry out an intended function, such as mediation or modulation of gene expression. The interaction of operatively linked sequences may, for example, be mediated by proteins that interact with the operatively linked sequences. A coding region of interest may also be introduced within a vector along with other sequences, typically heterologous, to produce a chimeric construct. A transcriptional regulatory region and a sequence of interest are "operably linked" when the sequences are functionally connected so as to permit transcription of the sequence of interest to be mediated or modulated by the transcriptional regulatory region.

As described below, variegated plants were produced using the methods as described herein with *Nicotiana tabacum* L. cv. SR1, *Arabidopsis thaliana* cv Landsberg, *Brassica napus* cv. DH12075 *Oryza sativa* and *Brachypodium distachyon* cv. Doublon Blue Sky plants as model systems. However, other plants may also be modified using the methods described herein, including a crop plant, an ornamental plant, a forage plant, and the like, for example but not limited to *Nicotiana, Arabidopsis, Canola, Flax, Hemp, Brachypodium, Oryza, Brassica napus, Petunia* spp., *Cyclamen spp, Begonia* spp., *Azalea* spp, *Spatifilium* spp. alfalfa, corn, barley, rice, tobacco, *Arabidopsis*, canola, flax, hemp, for example but not limited to *Cannabis sativa*, potato. Other examples of plants include species from the genera *Anacardium, Arachis, Asparagus, Atropa, Avena, Brassica, Brachypodium, Citrus. Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna*, and *Zea*.

Constructs used for plant transformation include are set out in Table 4 and include:

Cpn21 AS (a nucleic acid sequence encoding Cpn21 in antisense orientation under transcriptional control of a constitutive, CaMV 35S promoter), Cpn21 RNAi-35S (Cpn21 RNAi hairpin-loop under transcriptional control of the 35S promoter), Cpn21 RNAi RBC (Cpn21 RNAi hairpin-loop under transcriptional control of a tissue specific, RuBisCO (RBC) promoter), Cpn21AS RBC a nucleic acid sequence encoding Cpn21 in antisense orientation under transcriptional control of the RBC promoter)

AlcRCpn21RNAi (Cpn21 RNAi hairpin-loop under transcriptional control of an alcohol inducible promoter).

Tobacco plants with varying levels of leaf variegation were produced using antisense expression of Cpn21 under the control of 35S promoter. Variegated tobacco plants were generated using on kanamycin selection medium or hygromycin selection medium, as well as to on selection-free medium. Variegated *Arabidopsis*, canola (*B. napus*), *O. sativa* and *B. distachyon* plants were identified on kanamycin—free selection medium following transformation with Cpn21 gene in antisense orientation or RNAi.

The present invention also provides a method of selecting a plant comprising a nucleic acid of interest comprising, i) providing the plant comprising a first nucleic acid operatively linked to a first regulatory region, the first nucleic acid disrupts the expression of Cpn21, or functional homologue of Cpn21, and a second nucleic acid encoding a protein of interest and operatively linked to a second regulatory region, ii) growing the plant under conditions that result in the expression of the first and second nucleic acids, and iii) selecting plants that display a variegated phenotype.

The first nucleic acid (in the step of providing) may be an antisense Cpn21 or an antisense functional homologue of Cpn21, a nucleic acid that hybridizes under stringent conditions with the complement of an antisense Cpn21, or the complement of an antisense functional homologue of Cpn21 in vitro, or an RNAi that disrupts the expression of Cpn21, or functional homologue of Cpn21. Furthermore, the regulatory region may be an inducible regulatory region, a tissue specific regulatory region, a developmental regulatory region, or a constitutive regulatory region.

The second nucleic acid sequence encoding a protein of interest, may include any nucleic acid, for example, but not limited to, a nucleic acid sequence that encodes a pharmaceutically active protein, for example growth factors, growth regulators, antibodies, antigens, their derivatives useful for immunization or vaccination and the like, interleukins, insulin, G-CSF, GM-CSF, hPG-CSF, M-CSF or combinations thereof, interferons, for example, interferon-alpha, interferon-beta, interferon-gamma, blood clotting factors, for example, Factor VIII, Factor IX, or tPA or combinations thereof. The second nucleic acid sequence may also encode an industrial enzyme, a protein supplement, a nutraceutical, or a value-added product for feed, food, or both feed and food use. Examples of such proteins include, but are not limited to proteases, oxidases, phytases, chitinases, invertases, lipases, cellulases, xylanases, enzymes involved in oil biosynthesis etc.

The present invention is also directed to a chimeric construct containing a first and second nucleic acid operatively linked to a first and second regulatory region as describe above.

The present invention includes nucleotide sequences having antisense cpn21 activity and that hybridize to SEQ ID NO: 1, or that hybridized to the complement of antisense Cpn21 under stringent hybridization conditions (see Maniatis et al., in Molecular Cloning (A Laboratory Manual), Cold Spring Harbor Laboratory (1982) p. 387 to 389; Ausubel, et al. (eds), 1989, *Current Protocols in Molecular Biology*, Vol. 1, Green Publishing Associates, Inc., and John Wiley & Sons, Inc., New York, at p. 2.10.3; both of which are herein incorporated herein by reference). Non-limiting examples of stringent hybridization conditions include hybridization in 4XSSC at 65° C. for 8-16 hours, followed by washing in 0.1XSSC at 65° C. for an hour or hybridization in 5XSSC and 50% formamide at 42° C. for 8 to 16 hours, followed by washing in about 0.5XSSC to about 0.2XSSC at 65° C. for one hour. However, hybridization conditions may be modified in accordance with known methods depending on the sequence of interest (see Tijssen, 1993, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York; which is incorporated herein by reference). Generally, but not wishing to be limiting, stringent conditions are selected to be about 5° C. lower than the thermal melting point for the specific sequence at a defined ionic strength and pH.

As would be understood to one of skill in the art, nucleotide sequences of varying length that hybridize to SEQ ID NO: 1 or the complement of SEQ ID NO: 1, when transcribed in vivo, may exhibit the property of reducing cpn21 expression. Such nucleotide sequences may be from about 15 to about 900 nucleotides in length, or any length therebetween. Non-limiting examples of such sequences (including fragments of such sequences) include: GenBank Accession No. AF059037 (cpn10), GenBank Accession No. NM_180714 (cpn20), GenBank Accession No. AF510565.1 (hda2), and SEQ ID NO: 4.

The present invention also includes nucleotide sequences having RNAi activity for Cpn21. For example, SEQ ID NO: 5 comprises a 440 nucleotide sequence (nucleotides 223-663 of SEQ ID NO: 2), and a reverse, complement nucleotide sequence of nucleotides 223-663 of SEQ ID NO: 2) separated by an intron. When a nucleic acid having the sequence of SEQ ID NO: 5 is transcribed, the RNA forms a hairpin-loop structure (the intron is the loop, the nucleotides corresponding to SEQ ID NO: 2 form a paired region). As would be understood by one of skill in the art, the double-stranded region is cleaved into shorter double-stranded RNAi molecules specific for Cpn21.

Also included are sequences having from about 75 to about 100% sequence identity, or from about 80% to about 100% sequence identity, with the antisense Cpn21 sequence defined herein, provided that the sequences have antisense cpn21 activity. The identity determinations may be made using oligonucleotide alignment algorithms for example, but not limited to, BLAST (Altschul et al 1990. J. Mol. Biol 215:403-410; which is incorporated herein by reference). Software for performing BLAST analyses is available through the National Center for Biotechnology Information (GenBank URL: ncbi.nlm.nih.gov/cgi-bin/BLAST/). Default parameters include: Program: blastn; Database: nr; Expect 10; filter: default; Alignment: pairwise; Query genetic Codes: Standard (1)). Another example of an algorithm suitable for determining percent sequence identity and sequence similarity is FASTA (Pearson et al 1988. Proc Natl Acad Sci USA 85:2444-8).

A fragment or portion of a nucleic acid may comprise from about 60% to about 100%, of the length of the nucleic acid or nucleotide sequence, or any amount therebetween. For example, from about 60% to about 100%, from about 70% to about 100%, from about 80% to about 100%, from about 90% to about 100%, from about 95% to about 100%, of the length of the nucleic acid or nucleotide sequence, or any amount therebetween. Alternately, a fragment or portion may be from about 150 to about 500 nucleotides, or any amount therebetween. For example, a fragment may be from 150 to about 500 nucleotides, or any amount therebetween, from about 200 to about 500 nucleotides, or any amount therebetween, from about 250 to about 500 nucleotides, or any amount therebetween, from about 300 to about 500 or any amount therebetween, from about 350 to about 500 nucleotides, or any amount therebetween, from about 400 to about 500 or any amount therebetween, from about 450 to about 500 or any amount therebetween. For example, about 5, 10, 20, 30, 40 or 50 nucleotides, or any amount therebetween may be removed from the 5' end, the 3' end or both the 5' and 3' end of the nucleic acid or nucleotide sequence.

By "regulatory region" (or regulatory element) it is meant a nucleic acid sequence that has the property of controlling the expression of a sequence that is operatively linked with the regulatory region. Such regulatory regions may include promoter or enhancer regions, and other regulatory elements recognized by one of skill in the art. By "promoter" it is meant the nucleotide sequences at the 5' end of a coding region, or fragment thereof, that contain all the signals essential for the initiation of transcription and for the regulation of the rate of transcription.

There are several types of regulatory elements, including those that are developmentally regulated, inducible, tissue-specific, constitutive or the like. A regulatory element that is developmentally regulated, is activated within certain organs or tissues of an organ at specific times during the development of that organ or tissue, and regulates the differential expression of a gene. However, some regulatory elements that are developmentally regulated may preferentially be active within certain organs or tissues at specific developmental stages, or may also be active in a developmentally regulated manner, or at a basal level in other organs or tissues within the plant as well. Such regulatory elements may be found in any organ, for example but not limited to, leaves, root, stem, buds, fruit, seeds, flowers, tubers, ovules, embryos or the like.

A regulatory element may be derived from any suitable source provided that the regulatory element is active in the host plant. A regulatory element may be derived from the same species or type of plant or plant cell in which it is used, or it may be obtained from a different plant source. A regulatory element may also be an animal nucleic acid sequence, a bacterial nucleic acid sequence, a viral nucleic acid sequence, a protozoan nucleic acid sequence, or a cyanobacterial nucleic acid sequence, provided that the regulatory element functions within the host plant in which it is used. A regulatory element may comprise, in whole or in part, synthetic nucleic acid sequences not found in nature (a synthetic regulatory element).

A tissue-specific regulatory element is one that is capable of directly or indirectly activating transcription of one or more nucleotide sequences or genes in a tissue-specific manner. Such regulatory elements may be leaf-specific, guard cell specific, stem-specific, root specific, green tissue specific, organelle-specific or the like. Non limiting examples of guard-cell specific regulatory elements include promoter sequences of the *Arabidopsis* TGG1 gene (Husebye et al 2002. Plant Physiol 128:1180-1188; Plesch et al 2000 Gene 249:83-9; PCT Patent Application No. WO 93/018169; which are incorporated herein by reference). Non-limiting examples of organelle-specific regulatory elements include promoter sequences of the pea chlorophyll a/b binding protein gene AB80 (Zabaleta et al 1994. Plant J. 6:425-432; which is incorporated herein by reference). Non-limiting examples of leaf-specific regulatory elements are described in PCT Patent Publications WO 02/077248; WO02/036786; WO 98/00533 (which are incorporated herein by reference). Non-limiting examples of root-specific or root-active regulatory elements are described in PCT Patent Publications. WO 06/066193; WO 05/085449 (which are incorporated herein by reference).

An inducible regulatory element is one that is capable of directly or indirectly activating transcription of one or more DNA sequences or genes in response to an inducer. In the absence of an inducer the DNA sequences or genes will not be transcribed. Typically the protein factor, that binds specifically to an inducible regulatory element to activate transcription, may be present in an inactive form which is then directly or indirectly converted to the active form by the inducer. However, the protein factor may also be absent. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory element may be exposed to an inducer by externally applying the inducer to the cell or plant such as by spraying, watering, heating or similar methods. Inducible elements may be derived from either plant or non-plant genes (e.g. Gatz, C. and Lenk, I. R. P., 1998, Trends Plant Sci. 3, 352-358; which is incorporated by reference). Examples, of potential inducible promoters include, but not limited to, steroid inducible promoter, for example the estradiol promoter, tetracycline-inducible promoter (Gatz, C., 1997, Ann. Rev. Plant Physiol. Plant Mol. Biol. 48, 89-108; which is incorporated by reference), steroid inducible promoter (Aoyama, T. and Chua, N. H., 1997, Plant J. 2, 397-404; which is incorporated by reference), alcohol or ethanol-inducible promoter (Salter, M. G., et al, 1998, Plant Journal 16, 127-132; Caddick, M. X., et al, 1998, Nature Biotech. 16, 177-180, which are incorporated by reference) cytokinin inducible IB6 and UCH genes (Brandstatter, I. and Kieber, J. J., 1998, Plant Cell 10, 1009-1019; Kakimoto, T., 1996, Science 274, 982-985; which are incorporated by reference), auxin inducible element, DR5 (Ulmasov, T., et al., 1997, Plant Cell 9, 1963-1971; which is incorporated by reference), and a dexamethasone inducible promoter (Sablowski et al., 1998. Cell 92:93-103).

A constitutive regulatory element directs the expression of a gene throughout the various parts of a plant and continuously throughout plant development. Examples of known constitutive regulatory elements include promoters associated with the CaMV 35S transcript (Odell et al., 1985, *Nature*, 313: 810-812), octopine synthase promoter (Fromm et al 1989. Plant Cell 1:977-984), the nopaline synthase (NOS) promoter (Lam et al 1990. J. Biol. Chem. 265:9909-9913), the rice actin 1 (Zhang et al, 1991, *Plant Cell*, 3: 1155-1165) and triosephosphate isomerase 1 (Xu et al, 1994, *Plant Physiol.* 106: 459-467) genes, the maize ubiquitin 1 gene (Cornejo et al, 1993, *Plant Mol. Biol.* 29: 637-646), the *Arabidopsis* ubiquitin 1 and 6 genes (Holtorf et al, 1995, *Plant Mol. Biol.* 29: 637-646), tobacco t-CUP promoter (WO/99/67389; U.S. Pat. No. 5,824,872), the HPL promoter (WO 02/50291), and the tobacco translational initiation factor 4A gene (Mandel et al, 1995 *Plant Mol. Biol.* 29: 995-1004), all of which are herein incorporated by reference. The term "constitutive" as used herein does not necessarily indicate that a gene under control of the constitutive regulatory element is expressed at the same level in all cell types, but that the gene is expressed in a wide range of cell types even though variation in abundance is often observed.

Other non-limiting examples of developmentally regulated, inducible, tissue-specific, or constitutive regulatory elements are found in Table 1, and references therein, all of which are herein incorporated by reference.

TABLE 1

Regulatory elements

| Regulatory Element | Associated gene or marker | Reference |
|---|---|---|
| Green tissue specific promoter | RbsS3A | Panguluri et al 2005. Indian J. Exp Biol 43(4): 369-372 |
| Green leaf specific promoter | AtSTP3 | Buttner et al 2000. Plant Cell Env 23(2): 175-184 |
| Leaf primordial promoter | CAB | U.S. Pat. No. 5,639,952 |
| Light repressible promoter | Pra2 (pea) | AU 765413, CA2328139 |
|  | Pra2 (maize) | U.S. Pat. No. 5,639,952, U.S. Pat. No. 5,656,496 |
| Vein promoter | AtSUC2 | Imlau et al 1999. The Plant Cell 11: 309-322 |
| Heat shock promoter | sigma32 heat shock regulator | GenPept gi91070642 Chen et al 2005. PNAS 103(15): 5977-5982 |
| Alcohol-inducible promoter (Alc sequence) | alcR | Caddick et al., 1998 |
| Stem-specific promoter | Stem-specific protein | WO 01/18211 |
| Estradiol-inducible promoter | Per-8 | U.S. Pat. No. 6,784,340 |
| Heatshock promoter | Gmshp17.3 | Holtorf et al 1995. Plant Mol Biol 29(4): 637-646 |
| Pathogen-related promoter | PR1 | Beilmann et al 1992. Plant Mol Biol 18(1): 65-78 |
| Cotyledon-specific promoter | At2S1/ast2S2 | Guerche et al 1990. Plant Cell 2(5): 469-478 |
| Vascular tissue-specific promoter | RolC | Matsuki et al 1989. Molecular Genetics and Genomics 220: 12-16 |
| Flower-specific promoter | ChsA | Koch et al 2001. Mol Biol and Evol. 18: 1882-1891 |
| Light-inducible promoter | ST-LS1 (L700) | Stockhaus et al 1987. PNAS 84(22): 7943-7947 |
| RuBisCO | CbbL, cbbM | Giri et al 2004. Appl Environ Microbiol 70(6): 3443-3448 |
| Cold-inducible promoter | cspA | U.S. Pat. No. 6,479,260 |
| Light-specific promoter | ssu | U.S. Pat. No. 5,750,385 |
| Estrogen-inducible promoter | xve | Zua et al 2000. Plant J. 24(2): 265-273 |
| ABA-responsive promoter | CdeT27-45 | Michel et al., 1993 Plant J. 4: 29-40 |
| Epidermis-specific | NtItp1 | Canevascini et al., 1996. Plant Physiol 112: 513-24 |

Other non-limiting examples of regulatory elements may comprise particular sequences or response elements. For example, a regulatory element may comprise one or more cis-acting motifs, such as an abscisic acid response element, an Sph/RY element, a Myb recognition element or an Myc recognition element. These and/or other regulatory elements may be combined to provide a non-naturally occurring promoter, and inserted in -cis, 5' to the desired nucleic acid that is to be expressed (for example, the antisense cpn21, or the RNAi cpn21 as described herein).

The nucleic acid constructs of the present invention may be introduced into any desired plant, including forage plants, food crops, ornamental plants, or other plants depending upon the need. Thus, embodiments of the invention have use over a broad range of plants. Examples of such plants include, but not limited to, alfalfa, corn, barley, rice, tobacco, *Arabidopsis*, canola, wheat, oat, *Brassica, Oryza,* hemp, soybean, pea, ginseng, flax, hemp, maize, for example but not limited to *Cannabis sativa*, potato and ornamental plants, for example, but not limited to, *Petunia* spp., *Cyclamen* ssp, *Begonia* ssp, *Azalea* spp., *Spatifilium* spp. Other examples include species from the genera *Anacardium, Arachis, Artemesia, Asparagus, Atropa, Avena, Brassica, Brachypodium, Citrus. Citrullus, Capsicum, Carthamus, Cocos, Coffea* (e.g. *C. arabica, C. robusta*), *Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Musa* (e.g. Banana), *Nicotiana, Olea, Oryza, Panieum, Pannesetum, Persea, Phaseolus, Pistachia, Pisum, Pyrus, Prunus, Raphanus, Ricinus, Rosa, Secale, Senecio, Sinapis, Solanum, Sorghum, Theobromus, Trigonella, Triticum, Vicia, Vitis, Vigna, Zea* and the like.

In the experiments outlined below, tobacco, *Arabidopsis*, Canola, rice or *Brachypodium* were used as the test organism for the expression of the constructs as defined herein, however it is to be understood that the constructs of the present invention may be introduced and expressed in any plant.

Also considered part of this invention are transgenic plants comprising a construct, vector or nucleic acid as described herein.

Methods of regenerating whole plants from plant cells are known in the art. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques.

To aid in identification of transformed plant cells, the constructs of this invention may be further manipulated to include plant selectable markers. Selectable markers may include but are not limited to enzymes which provide for resistance to an antibiotic such as gentamycin, hygromycin, kanamycin, and the like. Similarly, enzymes providing for production of a compound identifiable by colour change such as GUS (beta-glucuronidase), luminescence, such as luciferase, metabolism of a particular carbon source (preventing growth of nontransformants) such as phosphomannose isomerase, are useful.

Nucleic acids, antisense molecules, silencing nucleotide sequences, vectors or other genetic constructs (collectively referred to as "constructs" or "nucleic acid constructs") may be introduced into plant cells using Ti plasmids, Ri plasmids, plant virus vectors, direct DNA transformation, micro-injection, electroporation, floral dip, biolistic particle gun, or the like. For reviews of such techniques see, for example, Weissbach and Weissbach, *Methods for Plant Molecular Biology*, Academy Press, New York VIII, pp. 421-463 (1988); Geierson and Corey, *Plant Molecular Biology*, 2d Ed. (1988); and Miki and Iyer, *Fundamentals of Gene Transfer in Plants*. In *Plant Metabolism*, $2^{nd}$ edition DT. Dennis, et al., (editors), Addison Wesley, Langmans Ltd. London, pp. 561-579 (1997); Clough and Bent, 1998 (Plant J. 16, 735-743). Hemp, for example but not limited to *Cannabis sativa* L. may be transformed using *Agrobacterium tumifasciens*, as described by Feeny and Punja, 2006. (Methods Mol Biol 344: 373-382; which is incorporated herein by reference)

The present invention further includes a suitable vector comprising the nucleic acid construct.

Also considered part of this invention are transgenic plants and their progeny that contain a nucleic acid construct of the present invention. Methods of regenerating whole plants from plant cells are known in the art, and the method of obtaining transformed and regenerated plants is not critical to this invention. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques. Plant regeneration from cultured protoplasts is described in Evans et al. (Protoplasts Isolation and Culture, Handbook of Plant Cell Culture, pp. 124-176, MacMillian Publishing Company, New York, 1983; and Binding, Regeneration of Plants, Plant Protoplasts, pp. 21-73, CRC Press, Boca Raton, 1985; which are incorporated herein by reference). Regeneration can also be obtained from plant callus, explants, organs, or parts thereof. Such regeneration techniques are described generally in Klee et al. 1987 (Ann. Rev. Plant Phys. 38:467-486; which is incorporated herein by reference).

The silencing nucleic acid sequence or construct as described herein may also be introduced into a plant by crossing a first plant with a second plant that comprises the silencing nucleic acid sequence or construct, and selecting for expression of the nucleic acid.

TABLE 2

List of Sequences and primers according to some embodiments of the invention.

| SEQ ID NO: | Description | Table/Figure/Sequence |
|---|---|---|
| 1 | Arabidopsis Cpn21 | FIG. 8A |
| 2 | Cpn21 fragment | FIG. 8L |
| 4 | Cpn21 antisense 35S | FIG. 8B |
| 5 | Cpn21 RNAi fragment with intron | FIG. 8C |
| 6 | Cpn21 RNAi 35S | FIG. 8D |
| 7 | Cpn21 RNAi RBC | FIG. 8E |
| 8 | AlcR Cpn21 RNAi | FIG. 8F |
| 9 | 35S Promoter | FIG. 8G |
| 10 | AlcA promoter | FIG. 8H |
| 11 | RBC Promoter | FIG. 8I |
| 12 | AlcR fragment with required 35S Promoter | FIG. 8J |
| 13 | 35SSF | AAAGGAAGGTGGCTCCTAC |
| 14 | 35SSSR | CCATCTTTGCCCTTGAAGTC |
| 15 | CpnR2 | GGAGTTCCTCCACTTCAGCAACGGC |
| 16 | 35SF3 | CTACGAGGAGCACCCACCCCC |
| 17 | 35S-ASF | AAGGAAAGGCCATCGTTG |

TABLE 2-continued

List of Sequences and primers according to some embodiments of the invention.

| SEQ ID NO: | Description | Table/Figure/Sequence |
|---|---|---|
| 18 | 35S-ASR | CAAATACGCAGGAACTGAGG |
| 19 | RBCRnaiR | GAGCAGTGGATGGAAGTAAG |
| 20 | RBCRnaiF | ACTTTAGGGCACGATGTC |
| 21 | 35S RNAIF | CTATCACCGTGCCAATAG |
| 22 | AlcR | GAGCCGTATAGAGCAGAGAC |
| 23 | Cpn 21 Antisense | FIG. 8K |
| 24 | ACpn 21 RNAiF* | <u>GGGGACCACTTTGTACAAGAAAGCTGGG</u>TGGGAGGCAGAGGAGAAGACTTTAG |
| 25 | ACpn 21 RNAi R* | <u>GGGGACAAGTTTGTACAAAAAAGCAGGCT</u>GGCTTCCGGTTGATACTGGTAGAGG |
| 26 | ACpn 21 Antisense F | GGCACGTGAAATGGCGGCGACTCAACTTAC |
| 27 | ACpn 21 Antisense R | GGACTAGTCCAGATTATGCTCAGGCCGTTTAC |
| 28 | pGreen0029-RBC | FIG. 8M |
| 29 | pUC57-RBC | FIG. 8N |

*Underlined sequences correspond to Gateway ™ (Invitrogen) extensions

The present invention will be further illustrated in the following examples. However it is to be understood that these examples are for illustrative purposes only, and should not be used to limit the scope of the present invention in any manner.

EXAMPLES

Methods
Vector Construction

Arabidopsis Chaperonin 21 sequence (GenBank Accession No. AF428366.1 gi:16226910 Arabidopsis thaliana AT5g20720/T1M15__120 mRNA; SEQ ID NO: 1) was used to design PCR primers incorporating Pm1I and Spe1 sites for cloning purposes.

Cpn21 Antisense under 35S promoter (cpn21AS) (SEQ ID NO: 4) A sequence encoding cpn21 was amplified from A. thaliana cDNA using primers ACpn 21 Antisense F and ACpn 21 Antisense R (SEQ ID NO: 26 and 27), incorporating Spe1 (at the 5' end) and Pm1I (at the 3' end) restriction enzyme recognition sequences for cloning purposes. The resulting PCR product was ligated into pGEM-T and verified by sequencing (resulting construct Acpn21 antisense pGEM-T). ACpn21 antisense pGEM-T was digested with Pm1I/Spe1 and the resulting 800 bp fragment containing Cpn21 was ligated into a pCambia 1302 vector cut with Pm1I/Spe1, and verified by sequencing.

The pCambia vector (available from CAMBIA) was derived from a pPZP backbone (Hajdukiewicz et al 1994. Plant Mol Biol 25:989-994; GenBank Accession No: AF234301).

The "Cpn21 RNAi-35S" (SEQ ID NO: 6) construct places expression of the RNAi sequence of Cpn21 under control of the 35S promoter (SEQ ID NO: 9). To make the Cpn21 RNAi constructs a 500 bp fragment from the middle of the Cpn21 gene was amplified by PCR using primers containing the Gateway® (Invitrogen) attB1 (forward) and attB2 (reverse) 5' extensions (ACpn 21 RNAi F and ACpn 21 RNAi R, SEQ ID NO: 24 and 25), following manufacturers' instructions. The Gateway® BP recombination reaction was used to insert the Cpn21 PCR product into a pDONR™ 221 vector, and the resulting Cpn21 pDONR construct verified by sequencing. The Gateway® LR recombination reaction was again used to insert the Cpn21 sequence from Cpn21 pDONR into pKGW1WG2II (Karimi et al., 2002 Trends Plant Sci 7(5): 193-195) in an RNAi format (sense and antisense sequences flanking an intron; when transcribed, the nucleic acid forms a hairpin-loop structure) (SEQ ID NO: 5) and verified by sequencing.

The "cpn21 RNAi-RBC" construct places expression of the RNAi sequence of Cpn21 under control of the RuBisCO (RBC) promoter (SEQ ID NO: 11). To make cpn21 RNAi-RBC (SEQ ID NO: 7), the cpn21 insert in RNAi orientation from pKGW1WG21I was excised with XmnI, and ligated into pGreen0029-RBC (SEQ ID NO: 28), linearized with XmnI/SmaI. pGreen0029-RBC comprises an N. tabacum RBC promoter (nucleotides 699-1744 of SEQ ID NO: 28) a multiple cloning site (nucleotides 1745-1841 of SEQ ID NO: 28), a sequence encoding a NOS terminator (nucleotides 1842-2122 of SEQ ID NO: 28), and was made by excising a KpnI/ApaI fragment of pUC57-RBC (SEQ ID NO: 29) comprising an RBC promoter, and ligating this fragment into a pGreen0029 vector that had been linearized with KpnI/ApaI. pGreen plasmids are known in the art and are described in, for example, references by Hellens et al., 2000 Plant Mol Biol 42:819-832; Hellens et al., 2000 Trends in Plant Sci 5:10:446-451; GenBank Accession No; Y09374).

The pUC57 vector is known and available from Genscript (GenScript USA Inc. 120 Centennial Ave Piscataway, N.J. Catalog #SD1176-50 ug). pUC57-RBC comprises a N. tabacum RBC promoter (nucleotides 21-1066 of SEQ ID NO: 29), a multiple cloning site (nucleotides 1067-1163 of SEQ ID NO: 29) and a sequence encoding a NOS terminator (nucleotides 1164-1444 of SEQ ID NO: 29).

The resulting cpn21 RNAi-RBC construct was digested with BamHI/XmnI to check for the presence of the insert.

The "Cpn21 AS-RBC" construct places expression of the sense orientation of Cpn21 under control of the RBC promoter. To make Cpn21 AS-RBC, the RBC promoter (SEQ ID NO: 11) was removed from pUC57 RBC (SEQ ID NO: 29) by digestion with HindIII and SpeI and inserted into pCambia 1302 AAS6 (from CAMBIA; cut with HindIII/SpeI) comprising a Cpn21 sequence in an antisense orientation. The resulting construct was digested with HindIII/SpeI to check for correct insert size.

Inducible constructs comprising the Alc were also made. The Alc regulon is describe in Caddick 1998 et al. Briefly, the minimal regulon includes an alcR sequence and an AlcA promoter. The AlcR polypeptide (transcription factor) responds to the inducer molecule (ethanol) when the plant is exposed to ethanol; the AlcR polypeptide binds the AlcA promoter, stimulating expression of the open reading frame operably linked to the AlcA promoter sequence.

Transformation of tobacco plants (*Nicotiana tabacum* L. cv. SR1)

Tobacco plants grown in vitro were utilised for *Agrobacterium* transformation with the above constructs (Cpn21AS, Cpn21 RNAi-RBC, Cpn21AS-RBC, AlcR Cpn21 RNAi). *A. tumifasciens* carrying the construct of interest were grown in suspension culture (400 ml) overnight in LB medium with antibiotics and agitation (28° C., 200 rpm). The bacterial suspension was centrifuged and resuspended in 5% sucrose ($OD_{600}$~1.0), supplemented with Silwet L-77 to a concentration of 0.02% (200 microliter (μL)/L). Leaf discs from in vitro growing plants were immersed for 30 minutes in the resuspended *A. tumifasciens*, followed by two days co-cultivation on solidified CT medium (Sigma-Aldrich). Co-cultivation was carried out in the dark 22° C. and 70% humidity. Transformants were selected using selection medium (Murashige & Skoog—"MS") in the presence or absence of selection agents (kanamycin or hygromycin) or induction agents (alcohol), according to the construct used in transformation (see Tables 3, 4 for media, selection agents, inducing agents). Plants demonstrating variegation were rooted and transferred to soil.

TABLE 3

Composition of tissue culture media utilised for plant variegation in vitro

| Media composition | CT plant co-cultivation medium | ½ strain MS seeds germination medium | MS tobacco shoots medium | MMO shoot initiation medium | N6 callus Induction medium | N6 Rice Re-generation medium | LS-*Brachypodium* Embryo Induction medium | LSR-*Brachypodium* Regeneration medium | MS basal medium |
|---|---|---|---|---|---|---|---|---|---|
| MS salts with vitamins | — | 2.2 g/l | 4.4 g/l | — | — | — | — | — | 4.4 g/l |
| MS minimal organics | — | — | — | 4.4 g/l | — | — | — | — | — |
| N6 salts | — | — | — | — | 3.98 g/l | 3.98 g/l | 3.98 g/l | 3.98 g/l | — |
| N6 Vitamins | — | — | — | — | 1 ml/l | 1 ml/l | 1 ml/l | 1 ml/l | — |
| Sucrose | — | 10 g/l | 30 g/l | 30 g/l | 30 g/l | 30 g/l | 30 g/l | — | 30 g/l |
| Glucose | 30 g/l | — | — | — | — | — | — | — | — |
| Maltose | — | — | — | — | — | — | — | 30 g/l | — |
| $KH_2PO_4$ | 0.2 g/l | — | — | — | — | — | — | — | — |
| 2.4 D | 1 mg/l* | — | — | — | 2 mg/l | — | 5 mg/l | — | — |
| NAA | — | — | — | — | — | 1 mg/l | — | — | — |
| IAA | 0.8 mg/l** | — | 0.8 mg/l | — | — | — | — | — | — |
| BA | — | — | — | 4.5 mg/l**** | — | 1 mg/l | — | — | — |
| kinetin | 2.0 mg/l** | — | 2.0 mg/l | — | — | — | — | 0.2 mg/l | — |
| DTT | 75 mg/l | — | 75 mg/l | 75 mg/l | 75 mg/l | 75 mg/l | 75 mg/l | 75 mg/l | — |
| Vitamin C | 150 mg/l | — | — | — | — | — | — | — | — |
| acetosyringone | 150 um | — | — | — | — | — | — | — | — |
| agar | 6.5 g/l*** | 6.5 g/l | 6.5 g/l | 6.5 g/l | 6.5 g/l | 6.5 g/l | 6.5 g/l | 6.5 g/l | 6.5 g/l |
| pH | 5.5 | 5.7 | 5.7 | 5.7 | 5.7 | 5.7 | 5.7 | 5.7 | 5.7 |

*Only for canola transformation
**Only for tobacco transformation
***The same media without agar (liquid one) was used to dissolve *Agrobacterium* after overnight grow and cocultivation with explants prior CT agar.

The "AlcR Cpn21 RNAi" construct (SEQ ID NO: 8) places expression of the RNA format of Cpn21 under control of an alcohol-inducible promoter (AlcA—SEQ ID NO: 10). To make AlcR Cpn21 RNAi, a nucleic acid sequence comprising Cpn21 in RNAi configuration (sense and antisense sequences flanking an intron; when transcribed, the nucleic acid forms a hairpin-loop structure) from pKGW1WG2II Cpn21 RNAi digested with PspOMI/XmnI, was ligated into a backbone containing an AlcA promoter from AIR-AIA pGreen 0029 cut with SwaI/NotI. The construct was digested with BglII to check for correct banding pattern. The A1R-A1A pGreen0029 construct was obtained from GenScript. A1R sequence (GenBank Accession No. XM_677155) and A1A promoter sequences (GenBank Accession No. M16196) are known in the art.

TABLE 4

Constructs, inducing and selection agents, promoters and plants tested.

| Construct | Inducing Agent | Selection Agent | Promoter | plants tested |
|---|---|---|---|---|
| Acpn21 antisense pGEMT | | | | |
| Cpn21 AS | none | hyg | 35S | T, C, A |
| AlcR Cpn21RNAi pDONR221 | ethanol | kan | AlcA | T |
| Cpn21 RNAi 35S | none | kan | 35S | T, C, R, B, A |
| Cpn21 RNAi RBC | none | kan | RBC | T |
| Cpn21 AS-RBC | none | kan | RBC | T |
| pKGW1WG211 | — | — | | |
| pGreen0029 RBC NARNRT | — | — | | — |

TABLE 4-continued

Constructs, inducing and selection agents, promoters and plants tested.

| Construct | Inducing Agent | Selection Agent | Promoter | plants tested |
|---|---|---|---|---|
| pUC57 RBC | — | — | | — |
| pCambia 1302 AS6 | — | — | | — |
| pCambia 1302 AAS6 | — | — | | — |
| AIR-AIA pGreen 0029 | — | — | | — |

T = *Nicotiana tabacum*
C = *Brassica napus* (Canola)
A = *Arabidopsis thaliana*
R = *Oryza sativa*
B = *Brachypodium distachyion*

Hygromycin B (Invitrogen) and kanamycin (Sigma/Aldrich) were used as selection agents. Selection media was also supplemented with Timentin (GlaxoSmithKline). 2-4-D (Sigma), BA (Sigma), indole-e-acetic acid (IAA) (Invitrogen) and kinetin (Sigma) were used for induction of callus and/or shoot regeneration.

Transformation of *Arabidopsis*

Transformation of *Arabidopsis* was according to the method of Clough and Bent, 1998. Briefly, *Arabidopsis* plants were grown until the flowering stage under long days light condition (16/8 hours photoperiod, 70% humidity, and 22° C.), in potsoil. *A. tumifasciens* carrying the construct of interest (Cpn21AS or Cpn21 RNAi RBC) was grown in suspension culture (400 ml) overnight in LB medium with antibiotics, with agitation. The bacterial suspension was centrifuged and resuspended in 5% sucrose ($OD_{600}$~0.8), supplemented with Silwet L-77 to a concentration of 0.02% (200 μL/L). Flowering plants were immersed for 2-3 sec in the *A. tumifasciens* suspension and placed under plastic wrap for 24 hours. Dry matured seeds were collected, sterilized and germinated in vitro on selection medium (50 mg/l hygromycin) or selection-free medium (lacking hygromycin).

Transformation of Canola (*Brassica napus*)

*B. napus* cultivar DH 12075 characterised by high regeneration efficiency was used for chaperonin-transformation experiments. Seeds were germinated on ½ MS media for 6 days under long day light conditions (22° C., 16/8 hours photoperiod, 70% humidity). Cotyledons along with petioles from six day old explants were used for transformation experiments.

*A. tumifasciens* carrying the construct of interest (cpn21AS or Cpn21RNAi-35S) was grown in suspension culture (400 ml) overnight in LB medium with antibiotics, with agitation (22° C., 200 rpm). Bacteria were collected by centrifugation and resuspended in CT medium at an $OD_{600}$=0.4. Cotyledons along with a portion of petioles were detached from the plantlets and the cut side of the tissue dipped in the *Agrobacterium* suspension.

Explants were co-cultivated for 48 hours on CT agar medium supplemented with 100 um acetosyringone, 1 mg/l 2.4-D and 75 mg/l DTT. Explants were then transferred to MMO selection media enriched with either with 4.5 mg/l BA, 200 mg/l timentin and with or without 5 mg/l hygromycin and with or without 50 mg/l kanamycin.

Well developed shoots were detached from the explants and transferred to fresh medium. Rooting was carried out on MS medium lacking growth regulators, supplemented with 200 mg/l timentin, with or without hygromycin. Well rooted plants were hardened in soil. Plants were grown to flowering stage in an isolator at 23° C. with 16/8 hour photoperiod. Mature seeds were harvested, sterilized, and germinated in vitro on selection media supplemented with 10 mg/l hygromycin or 100 mg/ml kanamycin. Young leaves were harvested for PCR analysis.

Example 1

Transformation of *N. tabacum* with Cpn21AS

*Nicotiana tabacum* L. cv. SR1 plants were transformed with cpn21 AS as described. The Cpn21 antisense sequence was expressed constitutively under control of the 35S promoter, as described.

Over 200 plants demonstrating various variegation patterns were selected following transformation in antisense orientation or RNAi. TO plants at flowering stage were grown under isolators in growth cabinet (23° C. day/19° C. night; 16/8 hour photoperiod). Seeds from 15 randomly chosen variegated plants were harvested and sterilised and germinated in vitro on ½ MS media with hygromycin (50 mg/l) or hygromycin free MS media (Tables 3 & 4). Three weeks after germination the number of $Hyg^R$ and $Hyg^S$ seedlings was determined. T0 and T1 plants were tested using PCR with primers 35S-ASR and 35S-ASF, to confirm the presence of the Cpn21 antisense sequence.

Shoots grown on hygromycin selection media were subcultured for further shoot elongation onto MS medium supplemented with hygromycin. At the shoot elongation stage, some leaves were lighter green, with small portions of dark green tissue at the edges while others exhibited variegation over the entire leaf. Variegated plants demonstrated rooting in hygromycin selection media, while those with bleached leaves demonstrated less viability, and reduced growth. Seeds from bleached plants either were not produced, or if they were, did not germinate upon cultivation in vitro. Partially variegated plants were grown under reduced light intensity (800 Lux) and produced viable seeds. 67.4% of regenerated shoots were rooted on hygromycin media. 12.2% of all hygromycin-resistant rooted plants were visibly variegated.

Variegated *N. tabacum* plants were also identified on hygromycin-free medium (MS-hyg). A plant was considered variegated if one or more regions of one or more leaves displayed differential coloration. The efficiency of transformation was slightly decreased when plants were regenerated without selection pressure—11.3% of regenerated plants were variegated and 4.4% were rooted after 3 weeks. These results demonstrate the variegation effect may be used as a marker of a transformed plant in the absence of artificial selection pressure.

T1 plants (produced by self fertilization of T0 plants) demonstrated variegation in ~25% of plants that germinated on hygromycin medium.

Nontransformed plants do not degrade hygromycin, and the surviving shoots on the selection medium (hygromycin-containing) were albino. Transformed plants grown on selection medium were green, or had some green tissue.

Example 2

Transformation of Tobacco with cpnRNAi-35S

Three weeks following transformation of leaf tissue with cpnRNAi-35S as described, shoots were assessed for variegation, coloration and rooting.

During the stage of shoot regeneration (initiation and elongation) bleaching was observed in some shoots under both selection and non-selection conditions (+/− kanamycin regeneration media). Well-growing shoots were subcultured for further elongation and rooting to MS selection medium. At this stage of shoot elongation, leaf coloration patterns included light green colouration over the entire leaf, variegated patterns, or yellow edges (FIG. 1). 67.4% of regenerated shoots were rooted on kanamycin media, including variegated plants. Plants with bleached leaves were less robust, and demonstrated reduced growth. Overall, 43.7% of kanamycin rooted plants demonstrated variegation.

Variegated plants were also grown on media lacking kanamycin selection. Transformation efficiency was decreased when plants were regenerated without selection pressure, with 23.3% of the explants having regenerated at least one variegated plant.

T0 plants at flowering stage were grown and the seeds harvested. Bleached plants either failed to produce seed, or produced seed that did not germinate. Partially variegated plants were grown under reduced light intensity (800 Lux) and produced viable seeds.

Seeds harvested from variegated plants were sterilised and germinated in vitro on ½ MS media with appropriate antibiotics (e.g. kanamycin at 500 mg/l) or antibiotic free MS media to produce T1 progeny, and the number of kanamycin resistant ($Kan^R$) and kanamycin sensitive ($Kan^S$) seedlings were tallied at 3 weeks' growth. Self-fertilisation of T0 regenerants yielded either near to 3:1 or 2:1 segregation ratio of kanamycin positive/negative plants, and a 3:1 ratio of variegation positive/variegation negative plants. Variegated T1 plants were easily identified on kanamycin negative media, and a variety of variegation patterns were observed, including bleached or light green leaf edges, with darker leaf tissue, light veination with darker leaf tissue, or speckled/spotted variegation over the entire leaf (FIG. 2A-E).

PCR was used on tissues from visibly variegated T1 progeny to confirm the transgenic status of the regenerants transformed with cpnRNAi-35S, however a significant rate of sterility in T1 seeds was observed. Seeds were germinated on MS basal cultivation media without selection, with 42% of the seeds were germinated and produced viable plants.

Example 3

Transformation of tobacco with Cpn21RNAi-RBC

Transformation efficiency of tobacco plants transformed with Cpn21RNAi-RBC under tissue specific promoter was similar to those transformed with Cpn21RNAi -35S. Leaves were generally brighter comparing to the control (wild type), with variegation in transformed plants observed at later growth stages. Stem colour, viability and morphology during vegetative development and flowering stage of the transformed plants was similar to untransformed plants, and seeds were produced. PCR was used on tissues from visibly variegated T1 progeny plants to confirm the transgenic status of the regenerants.

Example 4

Transformation of Tobacco with Cpn21RNAi-AlcR

Transformation efficiency of tobacco plants transformed with Cpn21RNAi-AlcR was similar to those transformed with Cpn21RNAi-35S or Cpn21RNAi-RBC. Regenerated plants demonstrated normal morphology and seed viability. (78% germination for T0 generation; 81% for wild type control).

Figure 3:
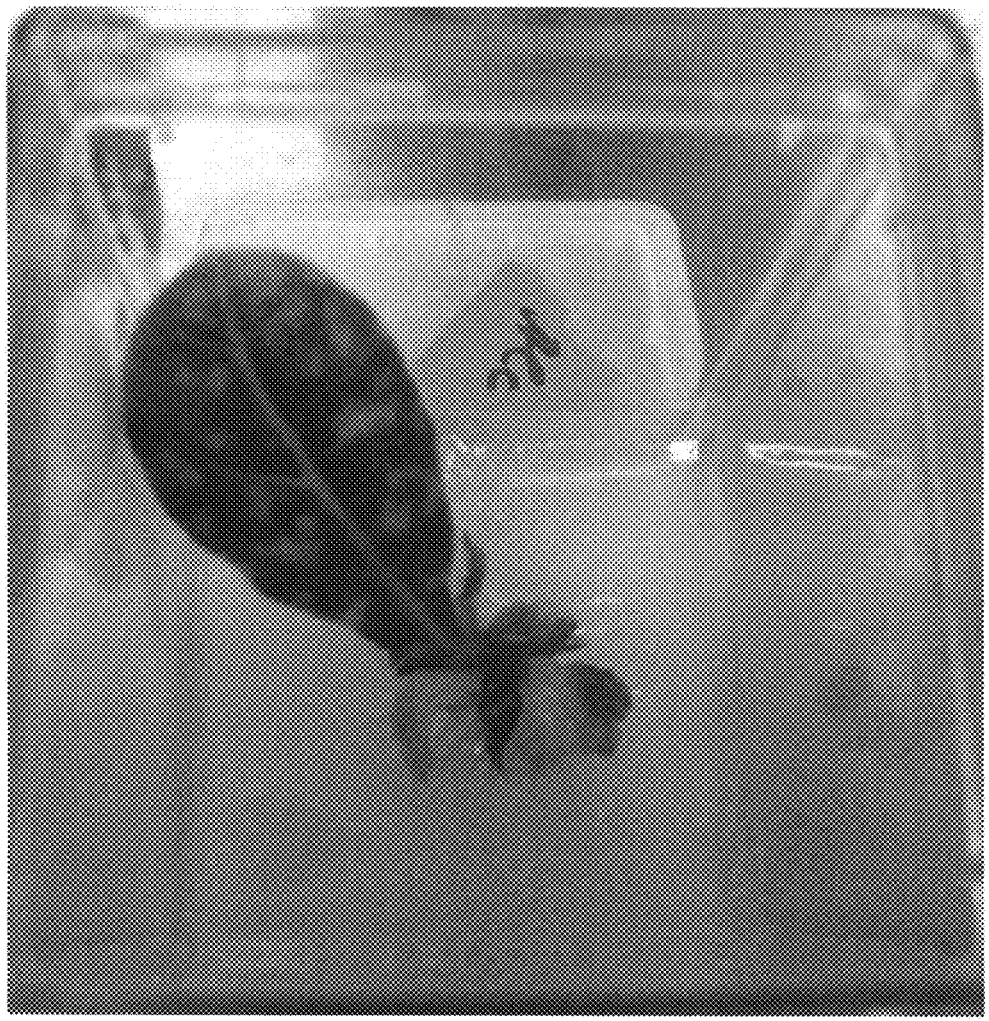
FIG. 3 shows variegation in the leaves of AlcR Cpn21RNAi transformed tobacco. The AlcA promoter was induced by spraying with a 2% ethanol solution.

During the stage of shoot elongation ethanol in concentration of 2% was added to the selection media if the plants were transformed with Cpn21 under ethanol inducible promoter. The new developed leaves demonstrated variegated morphology (FIG. 3). Some older leaves demonstrated variegation in the new growth meristematic areas.

Expression from the AlcR promoter may be induced by any of several methods: supplement of the cultivation media with 2% ethanol; exposure of regenerants to ethanol vapour (placement of a small test tube containing 99% ethanol inside the magenta jar with growing shoots); spraying leaves (in vitro or in vivo) with 2% ethanol. All three methods induced variegation in developing tissues, including leaves and stems. About 2% of the plants growing in ethanol free media also developed variegated pattern.

34.2% of rooted plants regenerated on antibiotic free media (supplemented with ethanol during shoot elongation) were visibly variegated. Regenerated plants were transferred to the soil and seeds were produced, harvested, sterilised and germinated in vitro. A germination ratio of about 3:1 (germinated:non-germinated) was observed on antibiotic selection (kanamycin) media. When ethanol was added to the regeneration media, 12.8% of the plants demonstrated variegation.

Example 5

Transformation of *Arabidopsis* with Cpn21S, Cpn21AS, Cpn21RNAi-35S

*Arabidopsis* was transformed with Cpn21AS and transgenic progeny grown as described.

Less than 1% (0.4%) efficiency was observed in *Arabidopsis* transformed with cpn21AS or Cpn21RNAi-35S constructs, and only 0.2% demonstrated variegation. The seedling transformants demonstrated bleaching, and lacked any significant amount of green colouration.

Transformants comprising Cpn21RNAi-35S were rooted on kanamycin selection media and viable seeds were produced by some variegated plants. T1 segregation of kanamycin resistant:sensitive was about 1:1; about 63.2% of regenerants were variegated. PCR was used on tissues from visibly variegated T1 progeny to confirm the transgenic status of the regenerants transformed with Cpn21RNAi-35S.

Example 6

Transformation of Canola (*Brassica napus*) with Cpn21RNAi-35S, cpn21AS

Figure 4:
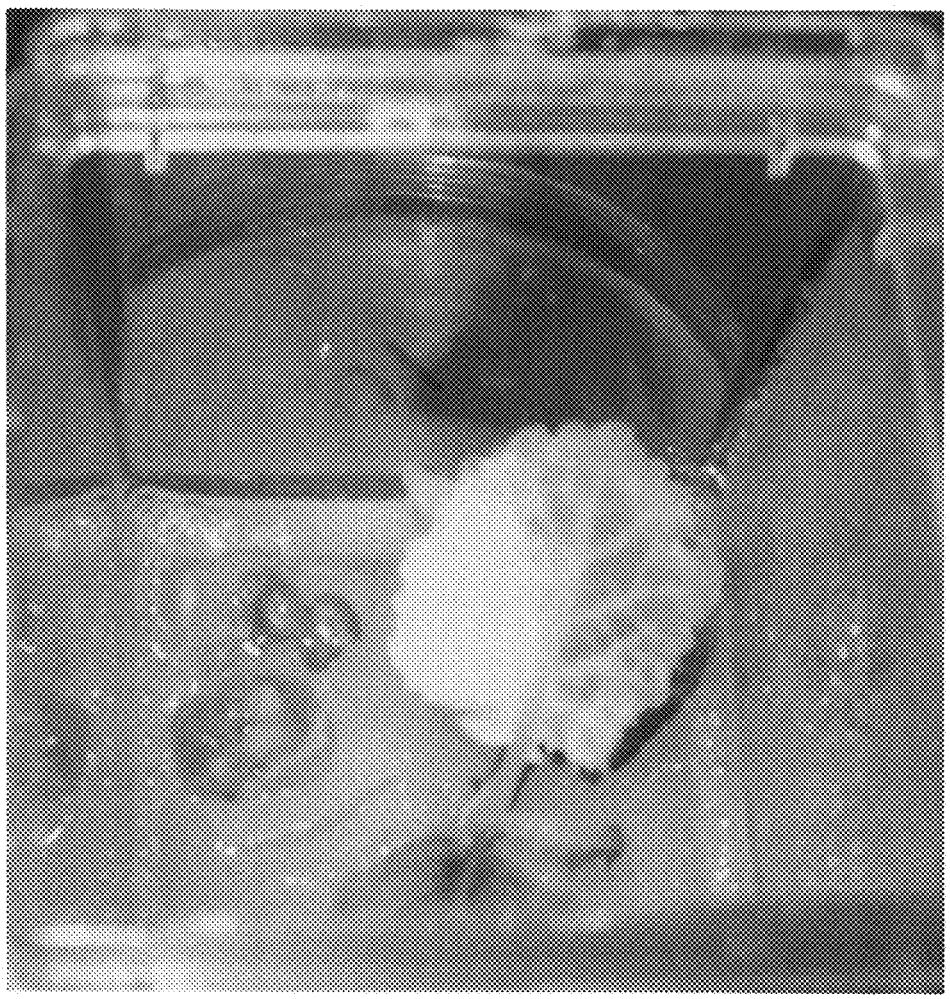
FIG. 4 shows a Canola (*Brassica napus*) regenerant on selection media after transformation with Cpn21RNAi-35S.
Figure 5:
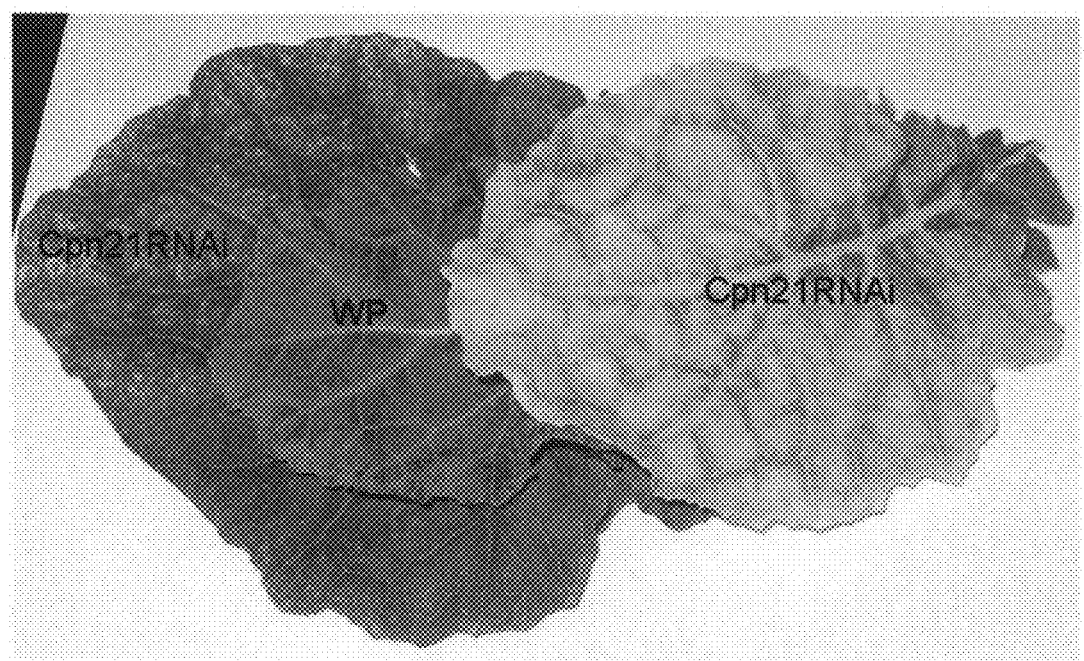
FIG. 5 shows patterns of variegation in canola transformed with Cpn21RNAi 35S (WP—untransformed control bottom left leaf).

The transformation efficiency with Cpn21RNAi-35S was low and few variegated plants were identified in the media without kanamycin selection. Approximately 32 variegated shoots (1.2% of total amount of the regenerants) were regenerated on kanamycin free media. T0 Plants developed roots but the growth was inhibited. Seed development was delayed relative to untransformed plants however viable seed was produced, and germinated seeds demonstrated variegation in early leaves and were distinguishable from untransformed plants (FIGS. 4 and 5).

PCR was used on tissues from visibly variegated T1 progeny plants to confirm the transgenic status of the regenerants.

Example 7

Constructs and Transgenic Plants Comprising Vein-Specific Promoter

A promoter for vein-specific expression of a chaperonin construct may be used to transform plants. The Cpn21AS construct may be digested with restriction enzymes to remove the 35S promoter, according to standard methods. An AtSUC2 promoter, amplified as described in Imlau et al 1999 (Cell 11:309-322) may be ligated into the cut vector, and the construct verified by sequencing. Briefly, PCR amplification may be performed using the primers HP-SUC2P, comprising HindIII and Pm1I sites (SEQ ID NO: 19) and SNN-SUC2P SacI, NotI, and NcoI sites (SEQ ID NO: 20). The resulting plasmid comprising the vein-specific promoter may be transformed into plant tissue of interest using known methods, such as those exemplified herein.

Example 8

Transformation of Oryza sativa (indica) with Cpn21RNAi-35S

Figure 6:
FIG. 6 shows transgenic rice, transformed with Cpn21RNAi-35S (right-side pot); left pot is control (untransformed plant).

An embryogenic culture was initiated from mature indica rice seeds (cv. Nipponbare) on 2xN6 medium supplemented with 2 mg/l 2-4D. The embryogenic culture was maintained by subculturing on the fresh medium every 3 weeks. For Agrobacterium mediated transformation, the protocol of Kumar et al., 2005 (Plant. Mol. Biol. Rep. 232: 67-73) was used. Regenerated shoots were obtained four to six weeks after the transfer of embryonic callus to regeneration media (supplemented with kanamycin 100 mg/l and 200 mg/l timentin). Elongated shoots were rooted on selection media. Well rooted plants were subsequently transferred to pots (FIG. 6) for growth, maturation and production of seed. Self-pollinated and T1 seeds were germinated in kanamycin (500 mg/l) selection medium. PCR was used on tissues from visibly variegated T1 progeny plants to confirm the transgenic status of the regenerants.

Example 9

Transformation of Brachypodium distachyon with Cpn21RNAi-35S

Figure 7:
FIG. 7 shows transgenic Brachypodium, transformed with Cpn21RNAi 35S (left-side pot); right pot is control (untransformed plant).

Immature embryos were utilized as a source of primary explants for embryogenic culture, using the protocol of Draper et al., (2001). (Plant Physiol. 127: 1539-1555). Embryo initiation was on media (LS) supplemented with 5 mg/l2-4D (callus-inducing medium, CIM). The embryogenic culture was maintained by subculturing on CIM fresh medium every 3 weeks. For Agrobacterium mediated transformation, the protocol of Vogel et al., 2006 (Cell, Tissue and Organ Culture 84: 199-211) was used. Regenerated shoots were obtained four to six weeks after the transfer of embryonic callus to regeneration media, supplemented with 0.2 mg/l kinetin, 50 mg/l kanamycin and 150 mg/l timentin. Elongated shoots were rooted on selection media. Well rooted plants were transferred to pots (FIG. 7) for growth, maturation and production of seed. Self-pollinated and T1 seeds germinated in kanamycin (500 mg/l) selection medium. PCR was used on tissues from visibly variegated T1 progeny plants to confirm the transgenic status of the regenerants.

All citations are herein incorporated by reference, as if each individual publication was specifically and individually indicated to be incorporated by reference herein and as though it were fully set forth herein. Citation of references herein is not to be construed nor considered as an admission that such references are prior art to the present invention.

One or more currently preferred embodiments of the invention have been described by way of example. The invention includes all embodiments, modifications and variations substantially as hereinbefore described and with reference to the examples and figures. It will be apparent to persons skilled in the art that a number of variations and modifications can be made without departing from the scope of the invention as defined in the claims. Examples of such modifications include the substitution of known equivalents for any aspect of the invention in order to achieve the same result in substantially the same way.

What is claimed is:

1. A plant comprising a heterologous nucleic acid operatively linked to a regulatory region, wherein the nucleic acid comprises the reverse complement of the sequence as set forth in SEQ ID NO: 1, and disrupts the expression of Cpn21 having the nucleotide sequence set forth in SEQ ID NO: 1 or an amino acid sequence comprising at least 61% identity to the amino acid sequence encoded by SEQ ID NO:1; and
wherein the plant exhibits a variegated phenotype and produces viable seed.

2. The plant of claim 1, wherein the regulatory region is an inducible regulatory region, a tissue specific regulatory region, a developmental regulatory region or a constitutive regulatory region.

3. The plant of claim 2, wherein the inducible regulatory region is an alcohol-inducible promoter.

4. The plant of claim 2, wherein the tissue specific regulatory region is a RuBisCO promoter.

5. The plant of claim 1, wherein RNA transcribed from the nucleic acid produces a double-stranded RNA (dsRNA).

6. A method of producing a plant exhibiting a variegated phenotype, the method comprising,
   i) providing the plant comprising a heterologous nucleic acid operatively linked to a regulatory region, the nucleic acid comprising the reverse complement of the sequence as set forth in SEQ ID NO: 1, and disrupting the expression of Cpn21 having the nucleotide sequence set forth in SEQ ID NO: 1 or an amino acid sequence comprising at least 61% identity to the amino acid sequence encoded by SEQ ID NO:1, and
   ii) growing the plant under conditions that results in the expression of the nucleic acid, thereby producing the plant having the variegated phenotype, wherein the plant produces viable seed.

7. The method of claim 6, wherein the regulatory region is an inducible regulatory region, a tissue specific regulatory region, a developmental regulatory region or a constitutive regulatory region.

8. A method of selecting a plant comprising a gene of interest comprising,
   i) providing the plant comprising a first heterologous nucleic acid operatively linked to a first regulatory region, wherein the first heterologous nucleic acid comprises the reverse complement of the sequence as set forth in SEQ ID NO: 1, and disrupts the expression of Cpn21 having the nucleotide sequence set forth in SEQ ID NO: 1 or an amino acid sequence comprising at least 61% identity to the amino acid sequence encoded by SEQ ID NO:1, and a second nucleic acid comprising the gene of interest and operatively linked to a second regulatory region,
   ii) growing the plant under conditions that result in the expression of the first and second nucleic acids, and
   iii) selecting plants that display a variegated phenotype and produce viable seed.

9. The method of claim 8, wherein the first regulatory region is an inducible regulatory region, a tissue specific regulatory region, a developmental regulatory region or a constitutive regulatory region.

10. The method of claim 9 wherein the inducible regulatory region is alcohol-inducible.

11. The method of claim 8, wherein the first regulatory region comprises an AlcA promoter and the gene of interest is AlcR.

12. The method of claim 6 wherein the regulatory region comprises a RuBisCO promoter.

13. The method of claim 6 wherein the regulatory region comprises an AlcA promoter.

14. The method of claim 6 wherein the regulatory region comprises a vein-specific promoter.

15. A seed that produces the plant of claim 1.

* * * * *

SEQUENCE LISTING

```
<160> NUMBER OF SEQ ID NOS: 29

<210> SEQ ID NO 1
<211> LENGTH: 955
<212> TYPE: DNA
<213> ORGANISM: Artificial Sequence
<220> FEATURE:
<223> OTHER INFORMATION: Arabidopsis thaliana Cpn21 coding sequence

<400> SEQUENCE: 1
aactctctct ctactgcaat ttttagggtt ttatcctccg aaagtctcaa cctttttctt      60
atcctcaaca aggagaaatg gcggcgactc aacttacagc gtcaccagtg actatgtcag     120
caaggagctt agcctcgctg gatggtctca gagcttcgag tgtcaagttt tcatctttga     180
aaccagggac ccttagacag agccagttcc gtcgtttggt tgtcaaagct gcttctgttg     240
ttgcccctaa gtatacttca attaagccat tgggagatcg agttttggtg aagatcaagg     300
aggcagagga gaagacttta ggtggtatct tacttccatc cactgctcaa tcaaaacctc     360
aaggaggtga agtcgttgcc gtgggtgaag gaagaactat tgggaagaac aaaattgata     420
tcactgtccc tactggagca caaattatct actccaaata cgcaggaact gaggtggagt     480
tcaatgatgt gaagcatctt atcctcaagg aagatgatat tgttggcatt cttgagacag     540
```

```
aggacatcaa agatctcaaa cctttgaatg accgagtctt tattaaggtt gctgaggcgg    600
aggagaaaac agctggaggg ttgttgttaa ccgagactac caaagagaag ccttctattg    660
gcacggtgat agcagttgga ccgggttccc tagacgagga aggtaaaatt acgcctctac    720
cagtatcaac cggaagcaca gtacttact ccaagtatgc tggtaacgac ttcaagggca     780
aagatggttc caactacatt gccctcagag cttcagatgt gatggctata ctttcttagt    840
tatgttatat ctttgtaatc tgcaacttgt atcccaattg tggaaatttt ttccgtaaac    900
ggcctgagca taatctggaa taaagacttg agtttgaaaa tgtgattttta ttgcc         955

<210> SEQ ID NO 2
<211> LENGTH: 850
<212> TYPE: DNA
<213> ORGANISM: Artificial Sequence
<220> FEATURE:
<223> OTHER INFORMATION: Cpn21 fragment

<400> SEQUENCE: 2
aatggcggcg actcaactta cagcgtcacc agtgactatg tcagcaagga gcttagcctc     60
gctggatggt ctcagagctt cgagtgtcaa gttttcatct ttgaaaccag ggacccttag    120
acagagccag ttccgtcgtt tggttgtcaa agctgcttct gttgttgccc ctaagtatac    180
ttcaattaag ccattgggag atcgagtttt ggtgaagatc aaggaggcag aggagaagac    240
tttaggtggt atcttacttc catccactgc tcaatcaaaa cctcaaggag gtgaagtcgt    300
tgccgtgggt gaaggaagaa ctattgggaa gaacaaaatt gatatcactg tccctactgg    360
agcacaaatt atctactcca aatacgcagg aactgaggtg gagttcaatg atgtgaagca    420
tcttatcctc aaggaagatg atattgttgg cattcttgag acagaggaca tcaaagatct    480
caaacctttg aatgaccgag tctttattaa ggttgctgag gcggaggaga aaacagctgg    540
agggttgttg ttaaccgaga ctaccaaaga gaagccttct attggcacgg tgatagcagt    600
tggaccgggt tccctagacg aggaaggtaa aattacgcct ctaccagtat caaccggaag    660
cacagtactt tactccaagt atgctggtaa cgacttcaag ggcaaagatg gttccaacta    720
cattgccctc agagcttcag atgtgatggc tatactttct tagttatgtt atatctttgt    780
aatctgcaac ttgtatccca attgtggaaa ttttttccgt aaacggcctg agcataatct    840
ggcacgtgtg                                                           850

<210> SEQ ID NO 3

<400> SEQUENCE: 3

000

<210> SEQ ID NO 4
<211> LENGTH: 10663
<212> TYPE: DNA
<213> ORGANISM: Artificial Sequence
<220> FEATURE:
<223> OTHER INFORMATION: Cpn21 antisense 35S

<400> SEQUENCE: 4
tgaccatggt agatctgact agtccagatt atgctcaggc cgtttacgga aaaaatttcc     60
acaattggga tacaagttgc agattacaaa gatataacat aactaagaaa gtatagccat    120
cacatctgaa gctctgaggg caatgtagtt ggaaccatct ttgcccttga agtcgttacc    180
agcatacttg gagtaaagta ctgtgcttcc ggttgatact ggtagaggcg taattttacc    240
```

```
ttcctcgtct agggaacccg gtccaactgc tatcaccgtg ccaatagaag gcttctcttt       300
ggtagtctcg gttaacaaca accctccagc tgttttctcc tccgcctcag caaccttaat       360
aaagactcgg tcattcaaag gtttgagatc tttgatgtcc tctgtctcaa gaatgccaac       420
aatatcatct tccttgagga taagatgctt cacatcattg aactccacct cagttcctgc       480
gtatttggag tagataattt gtgctccagt agggacagtg atatcaattt tgttcttccc       540
aatagttctt ccttcaccca cggcaacgac ttcacctcct tgaggttttg attgagcagt       600
ggatggaagt aagataccac ctaaagtctt ctcctctgcc tccttgatct tcaccaaaac       660
tcgatctccc aatggcttaa ttgaagtata cttaggggca acaacagaag cagctttgac       720
aaccaaacga cggaactggc tctgtctaag ggtccctggt ttcaaagatg aaaacttgac       780
actcgaagct ctgagaccat ccagcgaggc taagctcctt gctgacatag tcactggtga       840
cgctgtaagt tgagtcgccg ccatttcacg tgtgaattgg tgaccagctc gaatttcccc       900
gatcgttcaa acatttggca ataaagtttc ttaagattga atcctgttgc cggtcttgcg       960
atgattatca tataatttct gttgaattac gttaagcatg taataattaa catgtaatgc      1020
atgacgttat ttatgagatg ggttttttatg attagagtcc cgcaattata catttaatac      1080
gcgatagaaa acaaaatata gcgcgcaaac taggataaat tatcgcgcgc ggtgtcatct      1140
atgttactag atcgggaatt aaactatcag tgtttgacag gatatattgg cgggtaaacc      1200
taagagaaaa gagcgtttat tagaataacg gatatttaaa agggcgtgaa aaggtttatc      1260
cgttcgtcca tttgtatgtg catgccaacc acagggttcc cctcgggatc aaagtacttt      1320
gatccaaccc ctccgctgct atagtgcagt cggcttctga cgttcagtgc agccgtcttc      1380
tgaaaacgac atgtcgcaca agtcctaagt tacgcgacag gctgccgccc tgcccttttc      1440
ctggcgtttt cttgtcgcgt gttttagtcg cataaagtag aatacttgcg actagaaccg      1500
gagacattac gccatgaaca agagcgccgc cgctggcctg ctgggctatg cccgcgtcag      1560
caccgacgac caggacttga ccaaccaacg ggccgaactg cacgcggccg gctgcaccaa      1620 gctgtttttcc gagaagatca ccggcaccag gcgcgaccgc ccggagctgg ccaggatgct      1680
tgaccaccta cgccctggcg acgttgtgac agtgaccagg ctagaccgcc tggcccgcag      1740
cacccgcgac ctactggaca ttgccgagcg catccaggag gccggcgcgg gcctgcgtag      1800
cctggcagag ccgtgggccg acaccaccac gccggccggc cgcatggtgt tgaccgtgtt      1860
cgccggcatt gccgagttcg agcgttccct aatcatcgac cgcacccgga gcgggcgcga      1920
ggccgccaag gcccgaggcg tgaagtttgg ccccgccct accctcaccc cggcacagat      1980
cgcgcacgcc cgcgagctga tcgaccagga aggccgcacc gtgaaagagg cggctgcact      2040
gcttggcgtg catcgctcga ccctgtaccg cgcacttgag cgcagcgagg aagtgacgcc      2100
caccgaggcc aggcggcgcg gtgccttccg tgaggacgca ttgaccgagg ccgacgccct      2160
ggcggccgcc gagaatgaac gccaagagga caagcatga accgcacca ggacggccag      2220 gacgaaccgt ttttcattac cgaagagatc gaggcggaga tgatcgcggc cgggtacgtg      2280
ttcgagccgc ccgcgcacgt ctcaaccgtg cggctgcatg aaatcctggc cggtttgtct      2340
gatgccaagc tggcggcctg gccggccagc ttggccgctg aagaaaccga gcgccgccgt      2400
ctaaaaaggt gatgtgtatt tgagtaaaac agcttgcgtc atgcggtcgc tgcgtatatg      2460
atgcgatgag taaataaaca aatacgcaag gggaacgcat gaaggttatc gctgtactta      2520
accagaaagg cgggtcaggc aagacgacca tcgcaaccca tctagcccgc gccctgcaac      2580
tcgccggggc cgatgttctg ttagtcgatt ccgatcccca gggcagtgcc cgcgattggg      2640
```

```
cggccgtgcg ggaagatcaa ccgctaaccg ttgtcggcat cgaccgcccg acgattgacc    2700
gcgacgtgaa ggccatcggc cggcgcgact tcgtagtgat cgacggagcg ccccaggcgg    2760
cggacttggc tgtgtccgcg atcaaggcag ccgacttcgt gctgattccg gtgcagccaa    2820
gcccttacga catatgggcc accgccgacc tggtggagct ggttaagcag cgcattgagg    2880
tcacggatgg aaggctacaa gcggcctttg tcgtgtcgcg ggcgatcaaa ggcacgcgca    2940
tcggcggtga ggttgccgag gcgctggccg ggtacgagct gcccattctt gagtcccgta    3000
tcacgcagcg cgtgagctac ccaggcactg ccgccgccgg cacaaccgtt cttgaatcag    3060
aacccgaggg cgacgctgcc cgcgaggtcc aggcgctggc cgctgaaatt aaatcaaaac    3120
tcatttgagt taatgaggta aagagaaaat gagcaaaagc acaaacacgc taagtgccgg    3180
ccgtccgagc gcacgcagca gcaaggctgc aacgttggcc agcctggcag acacgccagc    3240
catgaagcgg gtcaactttc agttgccggc ggaggatcac accaagctga agatgtacgc    3300
ggtacgccaa ggcaagacca ttaccgagct gctatctgaa tacatcgcgc agctaccaga    3360
gtaaatgagc aaatgaataa atgagtagat gaattttagc ggctaaagga ggcggcatgg    3420
aaaatcaaga acaaccaggc accgacgccg tggaatgccc catgtgtgga ggaacgggcg    3480
gttggccagg cgtaagcggc tgggttgtct gccggccctg caatggcact ggaaccccca    3540
agcccgagga atcggcgtga cggtcgcaaa ccatccggcc cggtacaaat cggcgcggcg    3600
ctgggtgatg acctggtgga gaagttgaag gccgcgcagg ccgcccagcg caacgcatc     3660 gaggcagaag cacgccccgg tgaatcgtgg caagcggccg ctgatcgaat ccgcaaagaa    3720
tcccggcaac cgccggcagc cggtgcgccg tcgattagga agccgcccaa gggcgacgag    3780
caaccagatt ttttcgttcc gatgctctat gacgtgggca cccgcgatag tcgcagcatc    3840
atggacgtgg ccgttttccg tctgtcgaag cgtgaccgac gagctggcga ggtgatccgc    3900
tacgagcttc cagacgggca cgtagaggtt ccgcagggc cggccggcat ggccagtgtg    3960
tgggattacg acctggtact gatggcggtt tcccatctaa ccgaatccat gaaccgatac    4020
cgggaaggga agggagacaa gcccggccgc gtgttccgtc cacacgttgc ggacgtactc    4080
aagttctgcc ggcgagccga tggcggaaag cagaaagacg acctggtaga aacctgcatt    4140
cggttaaaca ccacgcacgt tgccatgcag cgtacgaaga aggccaagaa cggccgcctg    4200
gtgacggtat ccgagggtga agccttgatt agccgctaca agatcgtaaa gagcgaaacc    4260
gggcggccgg agtacatcga gatcgagcta gctgattgga tgtaccgcga gatcacagaa    4320
ggcaagaacc cggacgtgct gacggttcac cccgattact ttttgatcga tcccggcatc    4380
ggccgttttc tctaccgcct ggcacgccgc gccgcaggca aggcagaagc cagatggttg    4440
ttcaagacga tctacgaacg cagtggcagc gccggagagt tcaagaagtt ctgtttcacc    4500
gtgcgcaagc tgatcgggtc aaatgacctg ccggagtacg atttgaagga ggaggcgggg    4560
caggctggcc cgatcctagt catgcgctac cgcaacctga tcgagggcga agcatccgcc    4620
ggttcctaat gtacggagca gatgctaggg caaattgccc tagcagggga aaaggtcga    4680 aaaggtctct ttcctgtgga tagcacgtac attgggaacc caaagccgta cattgggaac    4740
cggaacccgt acattgggaa cccaaagccg tacattggga accggtcaca catgtaagtg    4800
actgatataa aagagaaaaa aggcgatttt tccgcctaaa actctttaaa acttattaaa    4860
actcttaaaa cccgcctggc ctgtgcataa ctgtctggcc agcgcacagc cgaagagctg    4920
caaaaagcgc ctaccctttcg gtcgctgcgc tccctacgcc ccgccgcttc gcgtcggcct    4980
```

```
atcgcggccg ctggccgctc aaaaatggct ggcctacggc caggcaatct accagggcgc    5040
ggacaagccg cgccgtcgcc actcgaccgc cggcgcccac atcaaggcac cctgcctcgc    5100
gcgtttcggt gatgacggtg aaaacctctg acacatgcag ctcccggaga cggtcacagc    5160
ttgtctgtaa gcggatgccg ggagcagaca agcccgtcag ggcgcgtcag cgggtgttgg    5220
cgggtgtcgg ggcgcagcca tgacccagtc acgtagcgat agcggagtgt atactggctt    5280
aactatgcgg catcagagca gattgtactg agagtgcacc atatgcggtg tgaaataccg    5340
cacagatgcg taaggagaaa ataccgcatc aggcgctctt ccgcttcctc gctcactgac    5400
tcgctgcgct cggtcgttcg gctgcggcga gcggtatcag ctcactcaaa ggcggtaata    5460
cggttatcca cagaatcagg ggataacgca ggaaagaaca tgtgagcaaa aggccagcaa    5520
aaggccagga accgtaaaaa ggccgcgttg ctggcgtttt tccataggct ccgcccccct    5580
gacgagcatc acaaaaatcg acgctcaagt cagaggtggc gaaacccgac aggactataa    5640
agataccagg cgtttccccc tggaagctcc ctcgtgcgct ctcctgttcc gaccctgccg    5700
cttaccggat acctgtccgc ctttctccct tcgggaagcg tggcgctttc tcatagctca    5760
cgctgtaggt atctcagttc ggtgtaggtc gttcgctcca agctgggctg tgtgcacgaa    5820
ccccccgttc agcccgaccg ctgcgcctta tccggtaact atcgtcttga gtccaacccg    5880
gtaagacacg acttatcgcc actggcagca gccactggta acaggattag cagagcgagg    5940
tatgtaggcg gtgctacaga gttcttgaag tggtggccta actacggcta cactagaagg    6000
acagtatttg gtatctgcgc tctgctgaag ccagttacct tcggaaaaag agttggtagc    6060
tcttgatccg gcaaacaaac caccgctggt agcggtggtt ttttttgtttg caagcagcag    6120 attacgcgca gaaaaaaagg atctcaagaa gatcctttga tcttttctac ggggtctgac    6180
gctcagtgga acgaaaactc acgttaaggg attttggtca tgcattctag gtactaaaac    6240
aattcatcca gtaaaatata atatttattt ttctcccaat caggcttgat ccccagtaag    6300
tcaaaaaata gctcgacata ctgttcttcc ccgatatcct ccctgatcga ccggacgcag    6360
aaggcaatgt cataccactt gtccgccctg ccgcttctcc caagatcaat aaagccactt    6420
actttgccat ctttcacaaa gatgttgctg tctcccaggt cgccgtggga aaagacaagt    6480
tcctcttcgg gcttttccgt ctttaaaaaa tcatacagct cgcgcggatc tttaaatgga    6540
gtgtcttctt cccagttttc gcaatccaca tcggccagat cgttattcag taagtaatcc    6600
aattcggcta agcggctgtc taagctattc gtatagggac aatccgatat gtcgatggag    6660
tgaaagagcc tgatgcactc cgcatacagc tcgataatct tttcagggct tgttcatct    6720 tcatactctt ccgagcaaag gacgccatcg gcctcactca tgagcagatt gctccagcca    6780
tcatgccgtt caaagtgcag gacctttgga acaggcagct ttccttccag ccatagcatc    6840
atgtcctttt cccgttccac atcataggtg gtcccttat accggctgtc cgtcattttt    6900
aaatataggt tttcattttc tcccaccagc ttatatacct tagcaggaga cattccttcc    6960
gtatctttta cgcagcggta ttttcgatc agttttttca attccggtga tattctcatt    7020
ttagccattt attatttcct tcctcttttc tacagtattt aaagataccc caagaagcta    7080
attataacaa gacgaactcc aattcactgt tccttgcatt ctaaaacctt aaataccaga    7140
aaacagcttt ttcaaagttg ttttcaaagt tggcgtataa catagtatcg acggagccga    7200
ttttgaaacc gcggtgatca caggcagcaa cgctctgtca tcgttacaat caacatgcta    7260
ccctccgcga gatcatccgt gtttcaaacc cggcagctta gttgccgttc ttccgaatag    7320
catcggtaac atgagcaaag tctgccgcct tacaacggct ctcccgctga cgccgtcccg    7380
```

```
gactgatggg ctgcctgtat cgagtggtga ttttgtgccg agctgccggt cggggagctg   7440
ttggctggct ggtggcagga tatattgtgg tgtaaacaaa ttgacgctta gacaacttaa   7500
taacacattg cggacgtttt taatgtactg aattaacgcc gaattaattc gggggatctg   7560
gattttagta ctggattttg gttttaggaa ttagaaattt tattgataga agtattttac   7620
aaatacaaat acatactaag ggtttcttat atgctcaaca catgagcgaa accctatagg   7680
aaccctaatt cccttatctg ggaactactc acacattatt atggagaaac tcgagcttgt   7740
cgatcgacag atccggtcgg catctactct atttctttgc cctcggacga gtgctggggc   7800
gtcggtttcc actatcggcg agtacttcta cacagccatc ggtccagacg ccgcgcttc   7860 tgcgggcgat ttgtgtacgc ccgacagtcc cggctccgga tcggacgatt gcgtcgcatc   7920
gaccctgcgc ccaagctgca tcatcgaaat tgccgtcaac caagctctga tagagttggt   7980
caagaccaat gcggagcata tacgcccgga gtcgtggcga tcctgcaagc tccggatgcc   8040
tccgctcgaa gtagcgcgtc tgctgctcca tacaagccaa ccacggcctc cagaagaaga   8100
tgttggcgac ctcgtattgg gaatccccga acatcgcctc gctccagtca atgaccgctg   8160
ttatgcggcc attgtccgtc aggacattgt tggagccgaa atccgcgtgc acgaggtgcc   8220
ggacttcggg gcagtcctcg gcccaaagca tcagctcatc gagagcctgc gcgacggacg   8280
cactgacggt gtcgtccatc acagtttgcc agtgatacac atggggatca gcaatcgcgc   8340
atatgaaatc acgccatgta gtgtattgac cgattccttg cggtccgaat gggccgaacc   8400
cgctcgtctg gctaagatcg gccgcagcga tcgcatccat agcctccgcg accggttgta   8460
gaacagcggg cagttcggtt tcaggcaggt cttgcaacgt gacaccctgt gcacggcggg   8520
agatgcaata ggtcaggctc tcgctaaact ccccaatgtc aagcacttcc ggaatcggga   8580
gcgcggccga tgcaaagtgc cgataaacat aacgatcttt gtagaaacca tcggcgcagc   8640
tatttacccg caggacatat ccacgccctc ctacatcgaa gctgaaagca cgagattctt   8700
cgccctccga gagctgcatc aggtcggaga cgctgtcgaa cttttcgatc agaaacttct   8760
cgacagacgt cgcggtgagt tcaggctttt tcatatctca ttgcccccg ggatctgcga   8820 aagctcgaga gagatagatt tgtagagaga gactggtgat tcagcgtgt cctctccaaa   8880 tgaaatgaac ttccttatat agaggaaggt cttgcgaagg atagtgggat tgtgcgtcat   8940
cccttacgtc agtggagata tcacatcaat ccacttgctt tgaagacgtg gttgaacgt   9000 cttctttttc cacgatgctc ctcgtgggtg ggggtccatc tttgggacca ctgtcggcag   9060
aggcatcttg aacgatagcc tttccttta cgcaatgatg gcatttgtag gtgccacctt   9120 cctttttctac tgtccttttg atgaagtgac agatagctgg gcaatggaat ccgaggaggt   9180
ttcccgatat tacccttgt tgaaaagtct caatagccct ttggtcttct gagactgtat   9240
ctttgatatt cttggagtag acgagagtgt cgtgctccac catgttatca catcaatcca   9300
cttgctttga agacgtggtt ggaacgtctt cttttccac gatgctcctc gtgggtgggg   9360
gtccatcttt gggaccactg tcggcagagg catcttgaac gatagccttt cctttatcgc   9420
aatgatggca tttgtaggtg ccaccttcct tttctactgt cctttgatg aagtgacaga   9480 tagctgggca atggaatccg aggaggtttc ccgatattac cctttgttga aaagtctcaa   9540
tagccctttg gtcttctgag actgtatctt tgatattctt ggagtagacg agagtgtcgt   9600
gctccaccat gttggcaagc tgctctagcc aatacgcaaa ccgcctctcc ccgcgcgttg   9660
gccgattcat taatgcagct ggcacgacag gtttcccgac tggaaagcgg gcagtgagcg   9720
```

| | |
|---|---|
| caacgcaatt aatgtgagtt agctcactca ttaggcaccc caggctttac actttatgct | 9780 |
| tccggctcgt atgttgtgtg gaattgtgag cggataacaa tttcacacag gaaacagcta | 9840 |
| tgaccatgat tacgaattcg agctcggtac ccggggatcc tctagagtcg acctgcaggc | 9900 |
| atgcaagctt ggcactggcc gtcgttttac aacgtcgtga ctgggaaaac cctggcgtta | 9960 |
| cccaacttaa tcgccttgca gcacatcccc ctttcgccag ctggcgtaat agcgaagagg | 10020 |
| cccgcaccga tcgcccttcc caacagttgc gcagcctgaa tggcgaatgc tagagcagct | 10080 |
| tgagcttgga tcagattgtc gtttcccgcc ttcagtttag cttcatggag tcaaagattc | 10140 |
| aaatagagga cctaacagaa ctcgccgtaa agactggcga acagttcata cagagtctct | 10200 |
| tacgactcaa tgacaagaag aaaatcttcg tcaacatggt ggagcacgac acacttgtct | 10260 |
| actccaaaaa tatcaaagat acagtctcag aagaccaaag ggcaattgag acttttcaac | 10320 |
| aaagggtaat atccggaaac ctcctcggat tccattgccc agctatctgt cactttattg | 10380 |
| tgaagatagt ggaaaaggaa ggtggctcct acaaatgcca tcattgcgat aaaggaaagg | 10440 |
| ccatcgttga agatgcctct gccgacagtg gtcccaaaga tggacccca cccacgagga | 10500 |
| gcatcgtgga aaaagaagac gttccaacca cgtcttcaaa gcaagtggat tgatgtgata | 10560 |
| tctccactga cgtaagggat gacgcacaat cccactatcc ttcgcaagac ccttcctcta | 10620 |
| tataaggaag ttcatttcat ttggagagaa cacggggggac tct | 10663 |

```
<210> SEQ ID NO 5
<211> LENGTH: 2630
<212> TYPE: DNA
<213> ORGANISM: Artificial sequence
<220> FEATURE:
<223> OTHER INFORMATION: Cpn21 RNAi fragment

<400> SEQUENCE: 5
```

| | |
|---|---|
| ctagtacaaa aaagcaggct ggggaggcag aggagaagac tttaggtggt atcttacttc | 60 |
| catccactgc tcaatcaaaa cctcaaggag gtgaagtcgt tgccgtgggt gaaggaagaa | 120 |
| ctattgggaa gaacaaaatt gatatcactg tccctactgg agcacaaatt atctactcca | 180 |
| aatacgcagg aactgaggtg gagttcaatg atgtgaagca tcttatcctc aaggaagatg | 240 |
| atattgttgg cattcttgag acagaggaca tcaaagatct caaacctttg aatgaccgag | 300 |
| tcttttattaa ggttgctgag gcggaggaga aacagctggg agggttgttg ttaaccgaga | 360 |
| ctaccaaaga gaagccttct attggcacgg tgatagcagt tggaccgggt tccctagacg | 420 |
| aggaaggtaa aattacgcct ctaccagtat caaccggaag cacccagctt tcatagtgac | 480 |
| tggatatgtt gtgttttaca gtattatgta gtctgttttt tatgcaaaat ctaatttaat | 540 |
| atattgatat ttatatcatt ttacgttct cgttcagctt tcttgtacaa agtggtgata | 600 |
| tcactagtgc ggccgcctgc aggtcgacca tatggtcgac ctgcaggcgg ccgcactagt | 660 |
| gatgctgtta tgttcagtgt caagctgacc tgcaaacacg ttaaatgcta agaagttaga | 720 |
| atatatgaga cacgttaact ggtatatgaa taagctgtaa ataaccgagt ataaactcat | 780 |
| taactaatat caacctctaga gtataatata atcaaattcg acaatttgac tttcaagagt | 840 |
| aggctaatgt aaaatctttta tatttctca caatgttcaa agaaacagtt gcatctaaac | 900 |
| ccctatggcc atcaaattca atgaacgcta agctgatccg gcgagatttt caggagctaa | 960 |
| ggaagctaaa atggagaaaa aaatcactgg atataccacc gttgatatat cccaatggca | 1020 |
| tcgtaaagaa cattttgagg catttcagtc agttgctcaa tgtacctata accagaccgt | 1080 |
| tcagctggat attacggcct tttaaagac cgtaaagaaa aataagcaca agttttatcc | 1140 |

```
ggcctttatt cacattcttg cccgcctgat gaatgctcat ccggaattcc gtatggcaat    1200
gaaagacggt gagctggtga tatgggatag tgttcaccct tgttacaccg ttttccatga    1260
gcaaactgaa acgttttcat cgctctggag tgaataccac gacgatttcc ggcagtttct    1320
acacatatat tcgcaagatg tggcgtgtta cggtgaaaac ctggcctatt tccctaaagg    1380
gtttattgag aatatgtttt tcgtctcagc caatccctgg gtgagtttca ccagttttga    1440
tttaaacgtg gccaatatgg acaacttctt cgcccccgtt ttcaccatgg gcaaatatta    1500
tacgcaaggc gacaaggtgc tgatgccgct ggcgattcag gttcatcatg ccgtctgtga    1560
tggcttccat gtcggcagaa tgcttaatga attacaacag tactgcgatg agtggcaggg    1620
cggggcgtaa acgcgtggat cagcttaata tgactctcaa taaagtctca taccaacaag    1680 tgccaccttaa tcaaccatc aagaaaaaag ccaaaattta tgctactcta aggaaaactt    1740
cactaaagaa gacgatttag agtgttttac caagaatttc tgtcatctta ctaaacaact    1800
aaagatcggt gtgatacaaa acctaatctc attaaagttt atgctaaaat aagcataatt    1860
ttacccacta agcgtgacca gataaacata actcagcaca ccagagcata tatattggtg    1920
gctcaaatca tagaaactta cagtgaagac acagaaagcc gtaagaagag gcaagagtat    1980
gaaaccttac ctcatcattt ccatgaggtt gcttctgatc ccgcgggata tcaccacttt    2040
gtacaagaaa gctgaacgag aaacgtaaaa tgatataaat atcaatatat taaattagat    2100
tttgcataaa aaacagacta cataatactg taaaacacaa catatccagt cactatgaaa    2160
gctgggtgct tccggttgat actggtgagg gcgtaatttt accttcctcg tctagggaac    2220
ccggtccaac tgctatcacc gtgccaatag aaggcttctc tttggtagtc tcggttaaca    2280
acaaccctcc agctgttttc tcctccgcct cagcaacctt aataaagact cggtcattca    2340
aaggtttgag atctttgatg tcctctgtct caagaatgcc aacaatatca tcttccttga    2400
ggataagatg cttcacatca ttgaactcca cctcagttcc tgcgtatttg gagtagataa    2460
tttgtgctcc agtagggaca gtgatatcaa ttttgttctt cccaatagtt cttccttcac    2520
ccacggcaac gacttcacct ccttgaggtt ttgattgagc agtggatgga agtaagatac    2580
cacctaaagt cttctcctct gcctccccag cctgcttttt tgtactagtg              2630
```

<210> SEQ ID NO 6
<211> LENGTH: 12333
<212> TYPE: DNA
<213> ORGANISM: Artificial sequence
<220> FEATURE:
<223> OTHER INFORMATION: Cpn21 RNAi 35S

<400> SEQUENCE: 6

```
aggatcccg ggtaccctcg aattatcata catgagaatt aagggagtca cgttatgacc      60
cccgccgatg acgcgggaca agccgtttta cgtttggaac tgacagaacc gcaacgttga    120
aggagccact cagccgcggg tttctggagt ttaatgagct aagcacatac gtcagaaacc    180
attattgcgc gttcaaaagt cgcctaaggt cactatcagc tagcaaatat tcttgtcaa    240 aaatgctcca ctgacgttcc ataaattccc ctcggtatcc aattagagtc tcatattcac    300
tctcaactcg atcgaggcat gattgaacaa gatggattgc acgcaggttc tccggccgct    360
tgggtggaga ggctattcgg ctatgactgg gcacaacaga caatcggctg ctctgatgcc    420
gccgtgttcc ggctgtcagc gcaggggcgc ccggttcttt ttgtcaagac cgacctgtcc    480
ggtgccctga atgaactcca agacgaggca gcgcggctat cgtggctggc cacgacgggc    540
```

```
gttccttgcg cagctgtgct cgacgttgtc actgaagcgg aagggactg gctgctattg   600 ggcgaagtgc cggggcagga tctcctgtca tctcaccttg ctcctgccga gaaagtatcc   660
atcatggctg atgcaatgcg gcggctgcat acgcttgatc cggctacctg cccattcgac   720
caccaagcga acatcgcat cgagcgagca cgtactcgga tggaagccgg tcttgtcgat    780
caggatgatc tggacgaaga gcatcagggg ctcgcgccag ccgaactgtt cgccaggctc   840
aaggcgcgga tgcccgacgg cgaggatctc gtcgtgaccc acggcgatgc ctgcttgccg   900
aatatcatgg tggaaaatgg ccgcttttct ggattcatcg actgtggccg gctgggtgtg   960
gcggaccgct atcaggacat agcgttggct acccgtgata ttgctgaaga gcttggcggc   1020
gaatgggctg accgcttcct cgtgctttac ggtatcgccg ctcccgattc gcagcgcatc   1080
gccttctatc gccttcttga cgagttcttc tgagcgggac tctggggttc ggactctagc   1140
tagagtcaag cagatcgttc aaacatttgg caataaagtt tcttaagatt gaatcctgtt   1200
gccggtcttg cgatgattat catataattt ctgttgaatt acgttaagca tgtaataatt   1260
aacatgtaat gcatgacgtt atttatgaga tgggttttta tgattagagt cccgcaatta   1320
tacatttaat acgcgataga aaacaaaata tagcgcgcaa actaggataa attatcgcgc   1380
gcggtgtcat ctatgttact agatcgaccg gcatgcaagc tgataattca attcggcgtt   1440
aattcagtac attaaaaacg tccgcaatgt gttattaagt tgtctaagcg tcaatttgtt   1500
tacaccacaa tatatcctgc caccagccag ccaacagctc cccgaccggc agctcggcac   1560
aaaatcacca ctcgatacag gcagcccatc agtccgggac ggcgtcagcg ggagagccgt   1620
tgtaaggcgg cagactttgc tcatgttacc gatgctattc ggaagaacgg caactaagct   1680
gccgggtttg aaacacggat gatctcgcgg agggtagcat gttgattgta acgatgacag   1740
agcgttgctg cctgtgatca attcgggcac gaacccagtg gacataagcc tcgttcggtt   1800
cgtaagctgt aatgcaagta gcgtaactgc cgtcacgcaa ctggtccaga accttgaccg   1860
aacgcagcgg tggtaacggc gcagtggcgg ttttcatggc ttcttgttat gacatgtttt   1920
tttggggtac agtctatgcc tcgggcatcc aagcagcaag cgcgttacgc cgtgggtcga   1980
tgtttgatgt tatggagcag caacgatgtt acgcagcagg cagtcgccc taaaacaaag   2040 ttaaacatca tgggggaagc ggtgatcgcc gaagtatcga ctcaactatc agaggtagtt   2100
ggcgtcatcg agcgccatct cgaaccgacg ttgctggccg tacatttgta cggctccgca   2160
gtggatggcg gcctgaagcc acacagtgat attgatttgc tggttacggt gaccgtaagg   2220
cttgatgaaa caacgcggcg agctttgatc aacgaccttt tggaaacttc ggcttcccct   2280
ggagagagcg agattctccg cgctgtagaa gtcaccattg ttgtgcacga cgacatcatt   2340
ccgtggcgtt atccagctaa gcgcgaactg caatttggag aatggcagcg caatgacatt   2400
cttgcaggta tcttcgagcc agccacgatc gacattgatc tggctatctt gctgacaaaa   2460
gcaagagaac atagcgttgc cttggtaggt ccagcggcgg aggaactctt tgatccggtt   2520
cctgaacagg atctatttga ggcgctaaat gaaaccttaa cgctatggaa ctcgccgccc   2580
gactgggctg gcgatgagcg aaatgtagtg cttacgttgt cccgcatttg gtacagcgca   2640
gtaaccggca aaatcgcgcc gaaggatgtc gctgccgact gggcaatgga gcgcctgccg   2700
gcccagtatc agcccgtcat acttgaagct agacaggctt atcttggaca agaagaagat   2760
cgcttggcct cgcgcgcaga tcagttggaa gaatttgtcc actacgtgaa aggcgagatc   2820
accaaggtag tcggcaaata atgtctagct agaaattcgt tcaagccgac gccgcttcgc   2880
cggcgttaac tcaagcgatt agatgcacta agcacataat tgctcacagc caaactatca   2940
```

```
ggtcaagtct gcttttatta tttttaagcg tgcataataa gccctacaca aattgggaga    3000
tatatcatgc atgaccaaaa tcccttaacg tgagttttcg ttccactgag cgtcagaccc    3060
cgtagaaaag atcaaaggat cttcttgaga tcctttttt ctgcgcgtaa tctgctgctt    3120
gcaaacaaaa aaaccaccgc taccagcggt ggtttgtttg ccggatcaag agctaccaac    3180 tcttttccg aaggtaactg gcttcagcag agcgcagata ccaaatactg tccttctagt    3240
gtagccgtag ttaggccacc acttcaagaa ctctgtagca ccgcctacat acctcgctct    3300
gctaatcctg ttaccagtgg ctgctgccag tggcgataag tcgtgtctta ccgggttgga    3360
ctcaagacga tagttaccgg ataaggcgca gcggtcgggc tgaacggggg gttcgtgcac    3420
acagcccagc ttggagcgaa cgacctacac cgaactgaga tacctacagc gtgagctatg    3480
agaaagcgcc acgcttcccg aagggagaaa ggcggacagg tatccggtaa gcggcagggt    3540
cggaacagga gagcgcacga gggagcttcc agggggaaac gcctggtatc tttatagtcc    3600
tgtcgggttt cgccacctct gacttgagcg tcgatttttg tgatgctcgt caggggggcg    3660
gagcctatgg aaaaacgcca gcaacgcggc ctttttacgg ttcctggcct tttgctggcc    3720
ttttgctcac atgttctttc ctgcgttatc ccctgattct gtggataacc gtattaccgc    3780
ctttgagtga gctgataccg ctcgccgcag ccgaacgacc gagcgcagcg agtcagtgag    3840
cgaggaagcg gaagagcgcc tgatgcggta ttttctcctt acgcatctgt gcggtatttc    3900
acaccgcata tggtgcactc tcagtacaat ctgctctgat gccgcatagt taagccagta    3960
tacactccgc tatcgctacg tgactgggtc atggctgcgc cccgacaccc gccaacaccc    4020
gctgacgcgc cctgacgggc ttgtctgctc ccggcatccg cttacagaca agctgtgacc    4080
gtctccggga gctgcatgtg tcagaggttt tcaccgtcat caccgaaacg cgcgaggcag    4140
ggtgccttga tgtgggcgcc ggcggtcgag tggcgacggc gcggcttgtc cgcgccctgg    4200
tagattgcct ggccgtaggc cagccatttt tgagcggcca gcggccgcga taggccgacg    4260
cgaagcggcg gggcgtaggg agcgcagcga ccgaagggta ggcgcttttt gcagctcttc    4320
ggctgtgcgc tggccagaca gttatgcaca ggccaggcgg ttttaagag ttttaataag    4380 ttttaaagag ttttaggcgg aaaaatcgcc ttttttctct tttatatcag tcacttacat    4440
gtgtgaccgg ttcccaatgt acggctttgg gttcccaatg tacgggttcc ggttcccaat    4500
gtacggcttt gggttcccaa tgtacgtgct atccacagga aagagacctt ttcgaccttt    4560
ttcccctgct agggcaattt gccctagcat ctgctccgta cattaggaac cggcggatgc    4620
ttcgccctcg atcaggttgc ggtagcgcat gactaggatc gggccagcct gccccgcctc    4680
ctccttcaaa tcgtactccg gcaggtcatt tgacccgatc agcttgcgca cggtgaaaca    4740
gaacttcttg aactctccgg cgctgccact gcgttcgtag atcgtcttga caaccatct    4800 ggcttctgcc ttgcctgcgg cgcggcgtgc caggcggtag agaaaacggc cgatgccggg    4860
atcgatcaaa aagtaatcgg ggtgaaccgt cagcacgtcc gggttcttgc cttctgtgat    4920
ctcgcggtac atccaatcag ctagctcgat ctcgatgtac tccggccgcc cggtttcgct    4980
ctttacgatc ttgtagcggc taatcaaggc ttcaccctcg gataccgtca ccaggcggcc    5040
gttcttggcc ttcttcgtac gctgcatggc aacgtgcgtg gtgtttaacc gaatgcaggt    5100
ttctaccagg tcgtctttct gctttccgcc atcggctcgc cggcagaact tgagtacgtc    5160
cgcaacgtgt ggacggaaca cgcggccggg cttgtctccc ttcccttccc ggtatcggtt    5220
catggattcg gttagatggg aaaccgccat cagtaccagg tcgtaatccc acacactggc    5280
```

```
catgccggcc ggccctgcgg aaacctctac gtgcccgtct ggaagctcgt agcggatcac    5340
ctcgccagct cgtcggtcac gcttcgacag acggaaaacg gccacgtcca tgatgctgcg    5400
actatcgcgg gtgcccacgt catagagcat cggaacgaaa aaatctggtt gctcgtcgcc    5460
cttgggcggt tcctaatcg acggcgcacc ggctgccggc ggttgccggg attctttgcg     5520
gattcgatca gcggccgctt gccacgattc accgggcgt gcttctgcct cgatgcgttg     5580
ccgctgggcg gcctgcgcgg ccttcaactt ctccaccagg tcatcaccca gcgccgcgcc    5640
gatttgtacc gggccggatg gtttgcgacc gtcacgccga ttcctcgggc ttggggttc     5700 cagtgccatt gcagggccgg cagacaaccc agccgcttac gcctggccaa ccgcccgttc    5760
ctccacacat ggggcattcc acggcgtcgg tgcctggttg ttcttgattt tccatgccgc    5820
ctcctttagc cgctaaaatt catctactca tttattcatt tgctcattta ctctggtagc    5880
tgcgcgatgt attcagatag cagctcggta atggtcttgc cttggcgtac cgcgtacatc    5940
ttcagcttgg tgtgatcctc cgccggcaac tgaaagttga cccgcttcat ggctggcgtg    6000
tctgccaggc tggccaacgt tgcagccttg ctgctgcgtg cgctcggacg gccggcactt    6060
agcgtgtttg tgcttttgct cattttctct ttacctcatt aactcaaatg agttttgatt    6120
taatttcagc ggccagcgcc tggacctcgc gggcagcgtc gccctcgggt tctgattcaa    6180
gaacggttgt gccggcggcg gcagtgcctg ggtagctcac gcgctgcgtg atacgggact    6240
caagaatggg cagctcgtac ccggccagcc cctcggcaac ctcaccgccg atgcgcgtgc    6300
ctttgatcgc ccgcgacacg acaaaggccg cttgtagcct tccatccgtg acctcaatgc    6360
gctgcttaac cagctccacc aggtcggcgg tgcccatat gtcgtaaggg cttggctgca   6420
ccggaatcag cacgaagtcg gctgccttga tcgcggacac agccaagtcc gccgcctggg    6480
gcgctccgtc gatcactacg aagtcgcgcc ggccgatggc cttcacgtcg cggtcaatcg    6540
tcgggcggtc gatgccgaca acggttagcg gttgatcttc ccgcacggcc gcccaatcgc    6600
gggcactgcc ctggggatcg gaatcgacta acagaacatc ggccccggcg agttgcaggg    6660
cgcgggctag atgggttgcg atggtcgtct tgcctgaccc gcctttctgg ttaagtacag    6720
cgataacctt catgcgttcc ccttgcgtat ttgtttattt actcatcgca tcatatacgc    6780
agcgaccgca tgacgcaagc tgtttactc aaatacacat caccttttta gacggcggcg    6840
ctcggtttct tcagcggcca agctggccgg ccaggccgcc agcttggcat cagacaaacc    6900
ggccaggatt tcatgcagcc gcacggttga gacgtgcgcg ggcggctcga acacgtaccc    6960
ggccgcgatc atctccgcct cgatctcttc ggtaatgaaa aacggttcgt cctggccgtc    7020
ctggtgcggt ttcatgcttg ttcctcttgg cgttcattct cggcggccgc cagggcgtcg    7080
gcctcggtca atgcgtcctc acggaaggca ccgcgccgcc tggcctcggt gggcgtcact    7140
tcctcgctgc gctcaagtgc gcggtacagg gtcgagcgat gcacgccaag cagtgcagcc    7200
gcctctttca cggtgcggcc ttcctggtcg atcagctcgc gggcgtgcgc gatctgtgcc    7260
ggggtgaggg tagggcgggg gccaaacttc acgcctcggg ccttggcggc ctcgcgcccg    7320
ctccgggtgc ggtcgatgat tagggaacgc tcgaactcgg caatgccggc gaacacggtc    7380
aacaccatgc ggccggccgg cgtggtggtg tcggcccacg gctctgccag gctacgcagg    7440
cccgcgccgg cctcctggat gcgctcggca atgtccagta ggtcgcgggt gctgcgggcc    7500
aggcggtcta gcctggtcac tgtcacaacg tcgccagggc gtaggtggtc aagcatcctg    7560
gccagctccg ggcggtcgcg cctggtgccg gtgatcttct cggaaaacag cttggtgcag    7620
ccggccgcgt gcagttcggc ccgttggttg gtcaagtcct ggtcgtcggt gctgacgcgg    7680
```

```
gcatagccca gcaggccagc ggcggcgctc ttgttcatgg cgtaatgtct ccggttctag    7740
tcgcaagtat tctactttat gcgactaaaa cacgcgacaa gaaaacgcca ggaaaagggc    7800
agggcggcag cctgtcgcgt aacttaggac ttgtgcgaca tgtcgttttc agaagacggc    7860
tgcactgaac gtcagaagcc gactgcacta tagcagcgga ggggttggat caaagtactt    7920
tgatcccgag gggaaccctg tggttggcat gcacatacaa atggacgaac ggataaacct    7980
tttcacgccc ttttaaatat ccgttattct aataaacgct cttttctctt aggtttaccc    8040
gccaatatat cctgtcaaac actgatagtt taaactgaag gcgggaaacg acaatctgat    8100
ccaagctcaa gctaagcttg agctctccca tatggtcgac tagagccaag ctgatctcct    8160
ttgccccgga gatcaccatg gacgactttc tctatctcta cgatctagga agaaagttcg    8220
acggagaagg tgacgatacc atgttcacca ccgataatga aagattagc ctcttcaatt    8280 tcagaaagaa tgctgaccca cagatggtta gagaggccta cgcggcaggt ctcatcaaga    8340
cgatctaccc gagtaataat ctccaggaga tcaaatacct tcccaagaag gttaaagatg    8400
cagtcaaaag attcaggact aactgcatca agaacacaga gaaagatata tttctcaaga    8460
tcagaagtac tattccagta tggacgattc aaggcttgct tcataaacca aggcaagtaa    8520
tagagattgg agtctctaag aaagtagttc ctactgaatc aaaggccatg gagtcaaaaa    8580
ttcagatcga ggatctaaca gaactcgccg tgaagactgg cgaacagttc atacagagtc    8640
ttttacgact caatgacaag aagaaaatct tcgtcaacat ggtggagcac gacactctcg    8700
tctactccaa gaatatcaaa gatacagtct cagaagacca aagggctatt gagacttttc    8760
aacaaagggt aatatcggga aacctcctcg gattccattg cccagctatc tgtcacttca    8820
tcaaaaggac agtagaaaag gaaggtggca cctacaaatg ccatcattgc gataaaggaa    8880
aggctatcgt tcaagatgcc tctgccgaca gtggtcccaa agatggaccc ccacccacga    8940
ggagcatcgt ggaaaaagaa gacgttccaa ccacgtcttc aaagcaagtg gattgatgtg    9000
atatctccac tgacgtaagg gatgacgcac aatcccacta tccttcgcaa gacccttcct    9060
ctatataagg aagttcattt catttggaga ggactgcagg acgatccgta tttttacaac    9120
aattaccaca acaaaacaaa caacaaacaa cattacaatt tactattcta gtcgacctgc    9180
aggcggccgc actagtgata tcacaagttt gtacaaaaaa gctgaacgag aaacgtaaaa    9240
tgatataaat atcaatatat taaattagat tttgcataaa aaacagacta cataatactg    9300
taaaacacaa catatccagt cactagtaca aaaagcagg ctggggaggc agaggagaag    9360
actttaggtg gtatcttact tccatccact gctcaatcaa aacctcaagg aggtgaagtc    9420
gttgccgtgg gtgaaggaag aactattggg aagaacaaaa ttgatatcac tgtccctact    9480
ggagcacaaa ttatcactc caaatacgca ggaactgagg tggagttcaa tgatgtgaag    9540
catcttatcc tcaaggaaga tgatattgtt ggcattcttg agacagagga catcaaagat    9600
ctcaaacctt tgaatgaccg agtctttatt aaggttgctg aggcggagga gaaacagct    9660 ggagggttgt tgttaaccga gactaccaaa gagaagcctt ctattggcac ggtgatagca    9720
gttggaccgg gttccctaga cgaggaaggt aaaattacgc ctctaccagt atcaaccgga    9780
agcacccagc tttcatagtg actggatatg ttgtgtttta cagtattatg tagtctgttt    9840
tttatgcaaa atctaattta atatattgat atttatatca ttttacgttt ctcgttcagc    9900
tttcttgtac aaagtggtga tatcccgcgg atcagaagc aacctcatgg aaatgatgag    9960
gtaaggtttc atactcttgc ctcttcttac ggctttctgt gtcttcactg taagtttcta   10020
```

```
tgatttgagc caccaatata tatgctctgg tgtgctgagt tatgtttatc tggtcacgct   10080
tagtgggtaa aattatgctt attttagcat aaactttaat gagattaggt tttgtatcac   10140
accgatcttt agttgtttag taagatgaca gaaattcttg gtaaaacact ctaaatcgtc   10200
ttctttagtg aagttttcct tagagtagca taaattttgg cttttttctt gatggttgaa   10260
taaggtggca cttgttggta tgagacttta ttgagagtca tattaagctg atccacgcgt   10320
ttacgccccg ccctgccact catcgcagta ctgttgtaat tcattaagca ttctgccgac   10380
atggaagcca tcacagacgg catgatgaac ctgaatcgcc agcggcatca gcaccttgtc   10440
gccttgcgta taatatttgc ccatggtgaa aacgggggcg aagaagttgt ccatattggc   10500 cacgttttaaa tcaaaactgg tgaaactcac ccagggattg gctgagacga aaacatatt   10560 ctcaataaac cctttaggga aataggccag gttttcaccg taacacgcca catcttgcga   10620
atatatgtgt agaaactgcc ggaaatcgtc gtggtattca ctccagagcg atgaaaacgt   10680
ttcagtttgc tcatggaaaa cggtgtaaca agggtgaaca ctatcccata tcaccagctc   10740
accgtctttc attgccatac ggaattccgg atgagcattc atcaggcggg caagaatgtg   10800
aataaaggcc ggataaaaact tgtgcttatt tttctttacg gtctttaaaa aggccgtaat   10860
atccagctga acggtctggt tataggtaca ttgagcaact gactgaaatg cctcaaaatg   10920
ttctttacga tgccattggg atatatcaac ggtggtatat ccagtgattt ttttctccat   10980
tttagcttcc ttagctcctg aaaatctcgc cggatcagct tagcgttcat tgaatttgat   11040
ggccataggg gtttagatgc aactgtttct ttgaacattg tagaaatata taagatttt   11100 acattagcct actcttgaaa gtcaaattgt cgaatttgat tatattatac tctagaggtg   11160
atattagtta atgagtttat actcggttat ttacagctta ttcatatacc agttaacgtg   11220
tctcatatat tctaacttct tagcatttaa cgtgtttgca ggtcagcttg acactgaaca   11280
taacagcatc actagtgcgg ccgcctgcag gtcgaccata tggtcgacct gcaggcggcc   11340
gcactagtga tatcaccact ttgtacaaga aagctgaacg agaaacgtaa aatgatataa   11400
atatcaatat attaaattag attttgcata aaaaacagac tacataatac tgtaaaacac   11460
aacatatcca gtcactatga aagctgggtg cttccggttg atactggtag aggcgtaatt   11520
ttaccttcct cgtctaggga acccggtcca actgctatca ccgtgccaat agaaggcttc   11580
tctttggtag tctcggttaa caacaaccct ccagctgttt tctcctccgc ctcagcaacc   11640
ttaataaaga ctcggtcatt caaaggtttg agatctttga tgtcctctgt ctcaagaatg   11700
ccaacaatat catcttcctt gaggataaga tgcttcacat cattgaactc cacctcagtt   11760
cctgcgtatt tggagtagat aatttgtgct ccagtaggga cagtgatatc aattttgttc   11820
ttcccaatag ttcttccttc acccacggca acgacttcac ctccttgagg ttttgattga   11880
gcagtggatg gaagtaagat accacctaaa gtcttctcct ctgcctcccc agcctgcttt   11940
tttgtacata gtgactggat atgttgtgtt ttacagtatt atgtagtctg tttttatgc    12000 aaaatctaat ttaatatatt gatatttata tcattttacg tttctcgttc agcttttttg   12060
tacaaacttg tgatatcccg cggccatgct agagtccgca aaaatcacca gtctctctct   12120
acaaatctat ctctctctat ttttctccag aataatgtgt gagtagttcc cagataaggg   12180
aattagggtt cttataggt ttcgctcatg tgttgagcat ataagaaacc cttagtatgt   12240 atttgtatttt gtaaaatact tctatcaata aaatttctaa ttcctaaaac caaaatccag   12300
tgacctgcag gcatgcgacg tcgggccctc tag                                12333
```

<210> SEQ ID NO 7
<211> LENGTH: 8868
<212> TYPE: DNA
<213> ORGANISM: Artificial sequence
<220> FEATURE:
<223> OTHER INFORMATION: Cpn21 RNAi RBC

<400> SEQUENCE: 7

```
gataagcttg tgggaacgag ataagggcga agtgcgctag tagcctgcta tttaaaatat      60
atccacaatt tataatgtat ttgaagatta gtcaattcgt ccaaaattca ggactaagta     120
tcttgaattt ttgtatcctg aattttggg  ctactaattt ggaactcagg acttaatgtc     180
ctaaattttt gagccgctaa tttgaaattc aggactaagt gttttgaatt tttgaactgc     240
ttattcgaaa tgcaagacta agtgacatga attttttgaac tgctaattta aaattcagga     300
cataagattt gaattttcaa acataatttt ttaactttag gcacgatgt  cctgaagttt     360
gaatcttgag atctaaactt caagatgcag cgtcttgaag tttgagtgaa ctggctaatc     420
tttaaatact tgtaaactgt ggatacattt ttaaataata tatttaaaag cggctacctg     480
gtatcatctt cacgagaatt ttccaagtta attgtaaagg aatagtggt  gttgcatcaa     540
gttatggaca atataaggaa gcaaacagta ctctagctat caaattagtt tccacttcta     600
aaccatgaat attaggaaaa acaagaaaca aaacaaatat acataaacaa tacggctaaa     660
gccaaggaaa agggactcta aaaaaattaa ccaacctcaa tcacacattc atatcctctt     720
cctaccccat ctaggatgag ataagattac taggtcttac acgtggcacc tccattgtgg     780
tgactaaatg aagagtggct tagctcaaaa tataattttc caacctttca tgtgtggata     840
ttaagttttg tgtagtgaat caagaaccac ataatccaat ggttagcttt attccaagat     900
gagggggttg ttgattttg  tccgtcagat ataggaaata tgtaaaacct tatcattata     960
tatagggtgg tgggcaacta tgcaatgacc atattggaag ttaaaggaaa agagagaaag    1020
agaaattctt cgtcaacatg gtggagcacg cactctcgt  ctactccaag aatatcaaag    1080
atacagtctc agaagaccaa agggctattg agacttttca acaaagggta atatcgggaa    1140
acctcctcgg attccattgc ccagctatct gtcacttcat caaaaggaca gtagaaaaaa    1200
taatgatttt attttgactg atagtgacct gttcgttgca acacattgat gagcaatgct    1260
ttttttataat gccaactttg tacaaaaaag caggctgggg aggcagagga gaagacttta    1320
ggtggtatct tacttccatc cactgctcaa tcaaaacctc aaggaggtga agtcgttgcc    1380
gtgggtgaag gaagaactat tgggaagaac aaaattgata tcactgtccc tactggagca    1440
caaattatct actccaaata cgcaggaact gaggtggagt tcaatgatgt gaagcatctc    1500
atcctcaagg aagatgatat tgttggcatt cttgagacag aggacatcaa agatctcaaa    1560
cctttgaatg accgagtctt tattaaggtt gctgaggcgg aggagaaaac agctggaggg    1620
ttgttgttaa ccgagactac caaagagaag ccttctattg gcacggtgat agcagttgga    1680
ccgggttccc tagacgagga aggtaaaatt acgcctctac cagtatcaac cggaagcacc    1740
cagctttctt gtacaaagtt ggcattataa gaaagcattg cttatcaatt tgttgcaacg    1800
aacaggtcac tatcagtcaa aataaaatca ttatttatca gaagcaacct catggaaatg    1860
atgaggtaag gtttcatact cttgcctctt cttacggctt tctgtgtctt cactgtaagt    1920
ttctatgatt tgagccacca atatatatgc tctggtgtgc tgagttatgt ttatctggtc    1980
acgcttagtg ggtaaaatta tgcttatttt agcataaact ttaatgagat taggttttgt    2040
atcacaccga tctttagttg tttagtaaga tgacagaaat tcttggtaaa acactctaaa    2100
```

```
tcgtcttctt tagtgaagtt ttccttagag tagcataaat tttggctttt ttcttgatgg    2160
ttgaataagg tggcacttgt tggtatgaga ctttattgag agtcatatta agctgatcca    2220
cgcgtttacg ccccgccctg ccactcatcg cagtactgtt gtaattcatt aagcattctg    2280
ccgacatgga agccatcaca gacggcatga tgaacctgaa tcgccagcgg catcagcacc    2340
ttgtcgcctt gcgtataata tttgcccatg gtgaaaacgg gggcgaagaa gttgtccata    2400
ttggccacgt ttaaatcaaa actggtgaaa ctcacccagg gattggctga gacgaaaaac    2460
atattctcaa taaacccttt agggaaatag gccaggtttt caccgtaaca cgccacatct    2520
tgcgaatata tgtgtagaaa ctgccggaaa tcgtcgtggt attcactcca gagcgatgaa    2580
aacgtttcag tttgctcatg gaaaacggtg taacaagggg gaacactatc ccatatcacc    2640
agctcaccgt ctttcattgc catacggaat tccggatgag cattcatcag gcggcaaga    2700 atgtgaataa aggccggata aaacttgtgc ttattttcet ttacggtctt taaaaaggcc    2760
gtaatatcca gctgaacggt ctggttatag gtacattgag caactgactg aaatgcctca    2820
aaatgttctt tacgatgcca ttgggatata tcaacggtgg tatatccagt gattttttc    2880 tccatttag cttccttagc tcctgaaaat ctcgccggat cagcttagcg ttcattgaat    2940
ttgatggcca taggggttta gatgcaactg tttctttgaa cattgtagaa atatataaag    3000
attttacatt agcctactct tgaaagtcaa attgtcgaat ttgattatat tatactctag    3060
aggtgatatt agttaatgag tttatactcg gttatttaca gcttattcat ataccagtta    3120
acgtgtctca tatattctaa cttcttagca tttaacgtgt ttgcaggtca gcttgacact    3180
gaacataaca gcatcactag tgcggccgcc tgcaggtcga ccatatggtc gacctgcagg    3240
cggccgcact agtgatatca aataatgatt ttattttgac tgatagtgac ctgttcgttg    3300
caacaaattg ataagcaatg ctttcttata atgccaactt tgtacaagaa agctgggtgc    3360
ttccggttga tactggtaga ggcgtaattt taccttcctc gtctagggaa cccggtccaa    3420
ctgctatcac cgtgccaata gaaggcttct cttggtagt ctcggttaac aacaaccctc    3480
cagctgtttt ctcctccgcc tcagcaacct taataaagac tcggtcattc aaaggtttga    3540
gatctttgat gtcctctgtc tcaagaatgc caacaatatc atcttccttg aggataagat    3600
gcttcacatc attgaactcc acctcagttc ctgcgtattt ggagtagata atttgtgctc    3660
cagtagggac agtgatatca attttgttct tcccaatagt tcttccttca cccacgcaa    3720 cgacttcacc tccttgaggt tttgattgag cagtggatgg aagtaagata ccacctaaag    3780
tcttctcctc tgcctcccca gcctgctttt ttgtacaaag ttggcattat aaaaaagcat    3840
tgctcatcaa tgtgttgcaa cgaacaggtc actatcagtc aaaataaaat cattatttga    3900
tatcccgcgg ccatgctaga gtccgcaaaa atcaccagtc tctctctaca aatctatctc    3960
tctctatttt tctccagaat aatgtgtgag tagttcccag ataagggaat tagggttctt    4020
ataggggttc gctcatgtgt tgagcatata agaaaccctt agtatgtatt tgtatttgta    4080
aaatacttct atcaataaaa tttctaattc ctaaaaccaa aatccagtga cctgcaggca    4140
tgcgacgtcg ggccctctag aggatccccg ggggatccac tagttctaga gcggccgcca    4200
ccgcggtgga gctccagctt ttgttccctt tagtgagggt taattccgag cttggcgtaa    4260
tcatggtcat agctgtttcc tgtgtgaaat tgttatccgc tcacaattcc acacaacata    4320
cgagccggaa ghcataaagt gtaaagcctg ggtgcctaa tgagtgagct aactcacatt    4380
aattgcgttg cgctcactgc ccgctttcca gtcgggaaac ctgtcgtgcc agctgcatta    4440
atgaatcggc caacgcgcgg ggagaggcgg tttgcgtatt gggcgctctt ccgcttcctc    4500
```

```
gctcactgac tcgctgcgct cggtcgttcg gctgcggcga gcggtatcag ctcactcaaa   4560
ggcggtaata cggttatcca cagaatcagg ggataacgca ggaaagaaca tgaaggcctt   4620
gacaggatat attggcgggt aaactaagtc gctgtatgtg tttgtttgag atctcatgtg   4680
agcaaaaggc cagcaaaagg ccaggaaccg aaaaaggccg cgttgctggc gttttttccat  4740 aggctccgcc cccctgacga gcatcacaaa aatcgacgct caagtcagag gtggcgaaac   4800
ccgacaggac tataaagata ccaggcgttt ccccctggaa gctccctcgt gcgctctcct   4860
gttccgaccc tgccgcttac cggatacctg tccgcctttc tcccttcggg aagcgtggcg   4920
ctttctcata gctcacgctg taggtatctc agttcggtgt aggtcgttcg ctccaagctg   4980
ggctgtgtgc acgaaccccc cgttcagccc gaccgctgcg ccttatccgg taactatcgt   5040
cttgagtcca acccggtaag acacgactta tcgccactgg cagcagccac tggtaacagg   5100
attagcagag cgaggtatgt aggcggtgct acagagttct tgaagtggtg cctaactac    5160 ggctacacta agaagaacagt atttggtatc tgcgctctgc tgaagccagt taccttcgga   5220
agaagagttg gtagctcttg atccggcaaa caaaccaccg ctggtagcgg tggttttttt   5280
gtttgcaagc agcagattac gcgcagaaaa aaaggatctc aagaagatcc tttgatcttt   5340
tctacggggt ctgacgctca gtggaacgaa aactcacgtt aagggatttt ggtcatgaga   5400
ttatcaaaaa ggatcttcac ctagatcctt taaattaaa aatgaagttt taaatcaatc    5460
taaagtatat atgtgtaaca ttggtctagt gattagaaaa actcatcgag catcaaatga   5520
aactgcaatt tattcatatc aggattatca ataccatatt tttgaaaaag ccgtttctgt   5580
aatgaaggag aaaactcacc gaggcagttc cataggatgg caagatcctg gtatcggtct   5640
gcgattccga ctcgtccaac atcaatacaa cctattaatt tcccctcgtc aaaaataagg   5700
ttatcaagtg agaaatcacc atgagtgacg actgaatccg gtgagaatgg caaaagttta   5760
tgcatttctt tccagacttg ttcaacaggc cagccattac gctcgtcatc aaaatcactc   5820
gcatcaacca aaccgttatt cattcgtgat tgcgcctgag cgagacgaaa tacgcgatcg   5880
ctgttaaaag gacaattaca aacaggaatc gaatgcaacc ggcgcaggaa cactgccagc   5940
gcatcaacaa tattttcacc tgaatcagga tattcttcta atacctggaa tgctgttttc   6000
cctgggatcg cagtggtgag taaccatgca tcatcaggag tacggataaa atgcttgatg   6060
gtcggaagag gcataaattc cgtcagccag tttagtctga ccatctcatc tgtaacaaca   6120
ttggcaacgc tacctttgcc atgtttcaga aacaactctg gcgcatcggg cttcccatac   6180
aatcggtaga ttgtcgcacc tgattgcccg acattatcgc gagcccattt atacccatat   6240
aaatcagcat ccatgttgga atttaatcgc ggccttgagc aagacgtttc ccgttgaata   6300
tggctcataa cacccccttgt attactgttt atgtaagcag acagttttat tgttcatgat   6360
gatatatttt tatcttgtgc aatgtaacat cagagatttt gagacacaac gtggctttgt   6420
tgaataaatc gaacttttgc tgagttgaag gatcagatca cgcatcttcc cgacaacgca   6480
gaccgttccg tggcaaagca aaagttcaaa atcaccaact ggtccaccta acaaaagct    6540 ctcatcaacc gtggctccct cactttctgg ctggatgatg gggcgattca ggcgatcccc   6600
atccaacagc ccgccgtcga gcgggctttt ttatccccgg aagcctgtgg atagagggta   6660
gttatccacg tgaaaccgct aatgccccgc aaagccttga ttcacggggc tttccggccc   6720
gctccaaaaa ctatccacgt gaaatcgcta atcagggtac gtgaaatcgc taatcggagt   6780
acgtgaaatc gctaataagg tcacgtgaaa tcgctaatca aaaaggcacg tgagaacgct   6840
```

```
aatagccctt tcagatcaac agcttgcaaa caccoctcgc tccggcaagt agttacagca    6900
agtagtatgt tcaattagct tttcaattat gaatatatat atcaattatt ggtcgccctt    6960
ggcttgtgga caatgcgcta cgcgcaccgg ctccgcccgt ggacaaccgc aagcggttgc    7020
ccaccgtcga cgccagcgc cttcgccac aacccggcgg ccggccgcaa cagatcgttt    7080
tataaatttt tttttttgaa aaagaaaaag cccgaaaggc ggcaacctct cgggcttctg    7140
gatttccgat ccccggaatt agagatcttg gcaggatata ttgtggtgta acgttatcag    7200
cttgcatgcc ggtcgatcta gtaacataga tgacaccgcg cgcgataatt tatcctagtt    7260
tgcgcgctat attttgtttt ctatcgcgta ttaaatgtat aattgcggga ctctaatcaa    7320
aaaacccatc tcataaataa cgtcatgcat tacatgttaa ttattacatg cttaacgtaa    7380
ttcaacagaa attatatgat aatcatcgca agaccggcaa caggattcaa tcttaagaaa    7440
ctttattgcc aaatgtttga acgatctgct tgactctagc tagagtccga accccagagt    7500
cccgctcaga agaactcgtc aagaaggcga tagaaggcga tgcgctgcga atcgggagcg    7560
gcgataccgt aaagcacgag gaagcggtca gcccattcgc cgccaagctc ttcagcaata    7620
tcacgggtag ccaacgctat gtcctgatag cggtccgcca cacccagccg ccacagtcg    7680
atgaatccga aaaagcggcc attttccacc atgatattcg gcaagcaggc atcgccctgg    7740
gtcacgacga gatcctcgcc gtcgggcatc cgcgccttga gcctggcgaa cagttcggct    7800
ggcgcgagcc cctgatgctc ttcgtccaga tcatcctgat cgacaagacc ggcttccatc    7860
cgagtacgtc ctcgctcgat gcgatgtttc gcttggtggt cgaatgggca ggtagccgga    7920
tcaagcgtat gcagccgccg cattgcatca gccatgatgg atactttctc ggcaggagca    7980
aggtgagatg acaggagatc ctgccccggc acttcgccca atagcagcca gtccctttcc    8040
gcttcagtga caacgtcgag cacagctgcg caaggaacgc ccgtcgtggc cagccacgat    8100
agccgcgctg cctcgtcttg gagttcattc agggcaccgg acaggtcggt cttgacaaaa    8160
agaaccgggc gcccctgcgc tgacagccgg aacacggcgg catcagagca gccgattgtc    8220
tgttgtgccc agtcatagcc gaatagcctc tccacccaag cggccggaga acctgcgtgc    8280
aatccatctt gttcaatcat gcctcgatcg agttgagagt gaatatgaga ctctaattgg    8340
ataccgaggg gaatttatgg aacgtcagtg gagcatttt gacaagaaat atttgctagc    8400
tgatagtgac cttaggcgac ttttgaacgc gcaataatgg tttctgacgt atgtgcttag    8460
ctcattaaac tccagaaacc gcggctgag tggctccttc aacgttgcgg ttctgtcagt    8520
tccaaacgta aaacggcttg tcccgcgtca tcggcggggg tcataacgtg actcccttaa    8580
ttctcatgta tcgataacat taacgtttac aatttcgcgc cattcgccat tcaggctgcg    8640
caactgttgg gaagggcgat cggtgcgggc ctcttcgcta ttacgccagc tggcgaaagg    8700
gggatgtgct gcaaggcgat taagttgggt aacgccaggg ttttcccagt cacgacgttg    8760
taaaacgacg gccagtgaat tgtaatacga ctcactatag gcgaattgg gtaccgggcc    8820
cccctcgag gtcgacggta tcgataagct tgatatcgaa ttcctgca                  8868
```

<210> SEQ ID NO 8
<211> LENGTH: 12159
<212> TYPE: DNA
<213> ORGANISM: Artificial sequence
<220> FEATURE:
<223> OTHER INFORMATION: AlcR Cpn21 RNAi Sequence

<400> SEQUENCE: 8

```
attcagggca ccggacaggt cggtcttgac aaaaagaacc gggcgcccct gcgctgacag    60
```

```
ccggaacacg gcggcatcag agcagccgat tgtctgttgt gcccagtcat agccgaatag    120
cctctccacc caagcggccg agaacctgc gtgcaatcca tcttgttcaa tcatgcctcg    180
atcgagttga gagtgaatat gagactctaa ttggataccg aggggaattt atggaacgtc    240
agtggagcat ttttgacaag aaatatttgc tagctgatag tgaccttagg cgacttttga    300
acgcgcaata atggtttctg acgtatgtgc ttagctcatt aaactccaga aacccgcggc    360
tgagtggctc cttcaacgtt gcggttctgt cagttccaaa cgtaaaacgg cttgtcccgc    420
gtcatcggcg ggggtcataa cgtgactccc ttaattctca tgtatcgata acattaacgt    480
ttacaatttc gcgccattcg ccattcaggc tgcgcaactg ttgggaaggg cgatcggtgc    540
gggcctcttc gctattacgc cagctggcga aggggatg tgctgcaagg cgattaagtt     600
gggtaacgcc agggttttcc cagtcacgac gttgtaaaac gacggccagt gaattgtaat    660
acgactcact ataggcgaa ttgggtaccg gccccccct cgaggtcgac tgccaacatg     720
gtggagcacg acactctcgt ctactccaag aatatcaaag atacagtctc agaagaccaa    780
agggctattg agacttttca acaaagggta atatcgggaa acctcctcgg attccattgc    840
ccagctatct gtcacttcat caaaaggaca gtagaaaagg aaggtggcac ctacaaatgc    900
catcattgcg ataaggaaa ggctatcgtt caagatgcct ctgccgacag tggtcccaaa     960
gatgaccccc cacccacgag gagcatcgtg aaaaagaag acgttccaac cacgtcttca    1020
aagcaagtgg attgatgtga acatggtg gagcacgaca ctctcgtcta ctccaagaat     1080
atcaaagata cagtctcaga agaccaaagg gctattgaga cttttcaaca agggtaata    1140 tcgggaaacc tcctcggatt ccattgccca gctatctgtc acttcatcaa aaggacagta    1200
gaaaaggaag gtggcaccta caaatgccat cattgcgata aggaaaggc tatcgttcaa    1260 gatgcctctg ccgacagtgg tcccaaagat ggaccccac ccacgaggag catcgtggaa    1320
aaagaagacg ttccaaccac gtcttcaaag caagtggatt gatgtgatat ctccactgac    1380
gtaagggatg acgcacaatc ccactatcct tcgcaagacc ttcctctata taggaagtt    1440 catttcattt ggagaggaca cgctgaaatc accagtctct ctctacaaat ctatctctct    1500
cgagctttcg cagatcccgg ggagtactat gtgctggaac cccgcatgct ccaggcctca    1560
ttccccagat ttcgactcca tggctgacag catccagacc gcacgttttt ggacttctga    1620
taccatctat acagatatca ctgtcgatat tctcctgcac acagcatggc agatacgcgc    1680
cgacgccaga atcatagctg cgatccctgt cgcaagggca agcgacgctg tgatgccccg    1740
aaacgaggcc aatgaaaacg gctgggtttc gtgttcaaat tgcaagcgtt ggaacaagga    1800
ttgtaccttc aattggctct catcccaacg ctccaaggca aaggggctg cacctagagc     1860 gagaacaaag aaagccagga ccgcaacaac caccagtgaa ccatcaactt cagctgcaac    1920
aatccctaca ccggaaagtg acaatcacga tgcgcctcca gtcataaact ctcacgacgc    1980
gctcccgagc tggactcagg gctactctc caccccgc gaccttttcg atttcagcca       2040
ctctgctatt cccgcaaatg cagaagatgc ggccaacgtg cagtcagacg caccttttcc    2100
gtgggatcta gccatcccg tgatttcag catgggccaa cagctcgaga aacctctcag      2160
tccgctcagt tttcaagcag tccttcttcc gccccatagc ccgaacacgg atgacctcat    2220
tcgcgagctg gaagagcaga ctacggatcc ggactcggtt accgatacta atagtgtaca    2280
acaggtcgct caagatggat cgctatggtc tgatcggcag tcgccgctac tgcctgagaa    2340
cagtctgtgc atggcctcag acagcacagc acggcgatat gcccgttcca caatgacgaa    2400
```

```
gaatctgatg cgaatctacc acgatagtat ggagaatgca ctgtcctgct ggctgacaga    2460
gcacaattgt ccatactccg accagatcag ctacctgccg cccaagcagc gggcggaatg    2520
gggcccgaac tggtcaaaca ggatgtgcat ccgggtgtgc cggctagatc gcgtatctac    2580
ctcattacgc gggcgcgccc tgagtgcgga agaggacaaa gccgcagccc gagccctgca    2640
tctggcgatc gtagcttttg cgtcgcaatg gacgcagcat gcgcagaggg gggctgggct    2700
aaatgttcct gcagacatag ccgccgatga gaggtccatc cggaggaacg cctggaatga    2760
agcacgccat gccttgcagc acacgacagg gattccatca ttccgggtta tatttgcgaa    2820
tatcatcttt tctctcacgc agagtgtgct ggatgatgat gagcagcacg gtatgggtgc    2880
acgtctagac aagctactcg aaaatgacgg tgcgcccgtg ttcctggaaa ccgcgaaccg    2940
tcagctttat acattccgac ataagtttgc acgaatgcaa cgccgcggta aggctttcaa    3000
caggctcccg ggaggatctg tcgcatcgac attcgccggt attttcgaga caccgacgcc    3060
gtcgtctgaa agcccacagc ttgacccggt tgtggccagt gaggagcatc gcagtacatt    3120
aagccttatg ttctggctag ggatcatgtt cgatacacta agcgctgcaa tgtaccagcg    3180
accactcgtg gtgtcagatg aggatagcca gatatcatcg gcatctccac caaggcgcgg    3240
cgctgaaacg ccgatcaacc tagactgctg ggagcccccg agacaggtcc cgagcaatca    3300
agaaaagagc gacgtatggg gcgacctctt cctccgcacc tcggactctc tcccagatca    3360
cgaatcccac acacaaatct ctcagccagc ggctcgatgg ccctgcacct acgaacaggc    3420
cgccgccgct ctctcctctg caacgcccgt caaagtcctc ctctaccgcc gcgtcacgca    3480
gctccaaacc ctcctctatc gcggcgcag ccctgcccgc cttgaagcgg ccatccagag    3540
aacgctctac gtttataatc actggacagc gaagtaccaa ccatttatgc aggactgcgt    3600
tgctaaccac gagctcctcc cttcgcgcat ccagtcttgg tacgtcattc tagacggtca    3660
ctggcatcta gccgcgatgt tgctagcgga cgttttggag agcatcgacc gcgattcgta    3720
ctctgatatc aaccacatcg accttgtaac aaagctaagg ctcgataatg cactagcagt    3780 tagtgcccett gcgcgctctt cactccgagg ccaggagctg gacccgggca aagcatctcc    3840
gatgtatcgc catttccatg attctctgac cgaggtggca ttcctggtag aaccgtggac    3900
cgtcgttctt attcactcgt ttgccaaagc tgcgtatatc ttgctggact gtttagatct    3960
ggacggccaa ggaaatgcac tagcggggta cctgcagctg cggcaaaatt gcaactactg    4020
cattcgggcg ctgcaatttc tgggcaggaa gtcggatatg gcggcgctgg ttgcgaagga    4080
tttagagaga ggttttgaatg ggaaagttga cagcttttg tagggagcgg gactctgggg    4140
ttcggactct agctagagtc aagcagatcg ttcaaacatt tggcaataaa gtttcttaag    4200
attgaatcct gttgccggtc ttgcgatgat tatcatataa tttctgttga attacgttaa    4260
gcatgtaata attaacatgt aatgcatgac gttatttatg agatgggttt tttgattaga    4320
gtcccgcaat tatacattta atacgcgata gaaaacaaaa tatagcgcgc aaactaggat    4380
aaaaagcttc cggatagtt ccgacctagg attggatgca tgcggaaccg cacgagggcg    4440
gggcggaaat tgacacacca ctcctctcca cgcagccgtt caagaggtac gcgtatagag    4500
ccgtatagag cagagacgga gcactttctg gtactgtccg cacgggatgt ccgcacggag    4560
agccacaaac gagcggggcc ccgtacgtgc tctcctaccc caggatcgca tcctcgcata    4620
gctgaacatc tatataagga agttcatttc atttggagag gacacgctga atcaccagt    4680 ctctctctac aaatctatct ctctcgagct ttcgcagatc ccggggagta ctcgaagtac    4740
ttcagatatc gaattcctgc agcggatcca ctagttctag acacgtgatt taaatggttt    4800
```

```
cttcgtcaac atggtggagc acgacactct cgtctactcc aagaatatca aagatacagt   4860
ctcagaagac caaagggcta ttgagacttt tcaacaaagg gtaatatcgg gaaacctcct   4920
cggattccat tgcccagcta tctgtcactt catcaaaagg acagtagaaa aaataatgat   4980
tttattttga ctgatagtga cctgttcgtt gcaacacatt gatgagcaat gcttttttat   5040
aatgccaact ttgtacaaaa aagcaggctg gggaggcaga ggagaagact ttaggtggta   5100
tcttacttcc atccactgct caatcaaaac ctcaaggagg tgaagtcgtt gccgtgggtg   5160
aaggaagaac tattgggaag aacaaaattg atatcactgt ccctactgga gcacaaatta   5220
tctactccaa atacgcagga actgaggtgg agttcaatga tgtgaagcat cttatcctca   5280
aggaagatga tattgttggc attcttgaga cagaggacat caaagatctc aaacctttga   5340
atgaccgagt ctttattaag gttgctgagg cggaggagaa aacagctgga gggttgttgt   5400
taaccgagac taccaaagag aagccttcta ttggcacggt gatagcagtt ggaccgggtt   5460
ccctagacga ggaaggtaaa attacgcctc taccagtatc aaccggaagc acccagcttt   5520
cttgtacaaa gttggcatta taagaaagca ttgcttatca atttgttgca acgaacaggt   5580
cactatcagt caaaataaaa tcattattta tcagaagcaa cctcatggaa atgatgaggt   5640
aaggtttcat actcttgcct cttcttacgg ctttctgtgt cttcactgta agtttctatg   5700
atttgagcca ccaatatata tgctctggtg tgctgagtta tgtttatctg gtcacgctta   5760
gtgggtaaaa ttatgcttat tttagcataa actttaatga gattaggttt tgtatcacac   5820
cgatctttag ttgtttagta agatgacaga aattcttggt aaaacactct aaatcgtctt   5880
ctttagtgaa gttttcctta gagtagcata aattttggct ttttttcttga tggttgaata   5940 aggtggcact tgttggtatg agactttatt gagagtcata ttaagctgat ccacgcgttt   6000
acgccccgcc ctgccactca tcgcagtact gttgtaattc attaagcatt ctgccgacat   6060
ggaagccatc acagacggca tgatgaacct gaatcgccag cggcatcagc accttgtcgc   6120
cttgcgtata atatttgccc atggtgaaaa cgggggcgaa gaagttgtcc atattggcca   6180
cgtttaaatc aaaactggtg aaactcaccc agggattggc tgagacgaaa aacatattct   6240
caataaaccc tttagggaaa taggccaggt tttcaccgta acacgccaca tcttgcgaat   6300
atatgtgtag aaactgccgg aaatcgtcgt ggtattcact ccagagcgat gaaaacgttt   6360
cagtttgctc atggaaaacg gtgtaacaag ggtgaacact atcccatatc accagctcac   6420
cgtctttcat tgccatacgg aattccggat gagcattcat caggcgggca agaatgtgaa   6480
taaaggccgg ataaaacttg tgcttatttt tctttacggt ctttaaaaag gccgtaatat   6540
ccagctgaac ggtctggtta taggtacatt gagcaactga ctgaaatgcc tcaaaatgtt   6600
ctttacgatg ccattgggat atatcaacgg tggtatatcc agtgatttt ttctccattt   6660 tagcttcctt agctcctgaa aatctcgccg gatcagctta gcgttcattg aatttgatgg   6720
ccataggggt ttagatgcaa ctgtttcttt gaacattgta gaaatatata aagattttac   6780
attagcctac tcttgaaagt caaattgtcg aatttgatta tattatactc tagaggtgat   6840
attagttaat gagtttatac tcggttattt acagcttatt catataccag ttaacgtgtc   6900
tcatatattc taacttctta gcatttaacg tgtttgcagg tcagcttgac actgaacata   6960
acagcatcac tagtgcggcc gcctgcaggt cgaccatatg gtcgacctgc aggcggccgc   7020
actagtgata tcaataatg attttatttt gactgatagt gacctgttcg ttgcaacaaa   7080
ttgataagca atgctttctt ataatgccaa ctttgtacaa gaaagctggg tgcttccggt   7140
```

```
tgatactggt agaggcgtaa ttttaccttc ctcgtctagg gaacccggtc caactgctat    7200
caccgtgcca atagaaggct tctctttggt agtctcggtt aacaacaacc ctccagctgt    7260
tttctcctcc gcctcagcaa ccttaataaa gactcggtca ttcaaaggtt tgagatcttt    7320
gatgtcctct gtctcaagaa tgccaacaat atcatcttcc ttgaggataa gatgcttcac    7380
atcattgaac tccacctcag ttcctgcgta tttggagtag ataatttgtg ctccagtagg    7440
gacagtgata tcaattttgt tcttcccaat agttcttcct tcacccacgg caacgacttc    7500
acctccttga ggttttgatt gagcagtgga tggaagtaag ataccaccta aagtcttctc    7560
ctctgcctcc ccagcctgct tttttgtaca agttggcat  tataaaaaag cattgctcat    7620
caatgtgttg caacgaacag gtcactatca gtcaaaataa aatcattatt tgatatcccg    7680
cggccatgct agagtccgca aaaatcacca gtctctctct acaaatctat ctctctctat    7740
ttttctccag aataatgtgt gagtagttcc cagataaggg aattagggtt cttataggqt    7800 ttcgctcatg tgttgagcat ataagaaacc cttagtatgt atttgtattt gtaaaatact    7860
tctatcaata aaatttctaa ttcctaaaac caaaatccag tgacctgcag gcatgcgacg    7920
tcgggccctc tagaggatcc ccaacgacgc gtagtttaaa catttatcct agtttgcgcg    7980
ctatattttg ttttctatcg cgtattaaat gtataattgc gggactctaa tcaaaaaacc    8040
catctcataa ataacgtcat gcattacatg ttaattatta catgcttaac gtaattcaac    8100
agaaattata tgataatcat cgcaagaccg gcaacaggat tcaatcttaa gaaactttat    8160
tgccaaatgt ttgaacgatc tgcttgactc tagctagagt ccgaacccca gagtcccgct    8220
caggcggccg ccaccgcggt ggagctccag cttttgttcc ctttagtgag ggttaattcc    8280
gagcttggcg taatcatggt catagctgtt tcctgtgtga aattgttatc cgctcacaat    8340
tccacacaac atacgagccg gaagcataaa gtgtaaagcc tggggtgcct aatgagtgag    8400
ctaactcaca ttaattgcgt tgcgctcact gcccgctttc cagtcgggaa acctgtcgtg    8460
ccagctgcat taatgaatcg gccaacgcgc ggggagaggc ggtttgcgta ttgggcgctc    8520
ttccgcttcc tcgctcactg actcgctgcg ctcggtcgtt cggctgcggc gagcggtatc    8580
agctcactca aaggcggtaa tacggttatc cacagaatca ggggataacg caggaaagaa    8640
catgaaggcc ttgacaggat atattggcgg gtaaactaag tcgctgtatg tgtttgtttg    8700
agatctcatg tgagcaaaag gccagcaaaa ggccaggaac cgtaaaaagg ccgcgttgct    8760
ggcgtttttc cataggctcc gcccccctga cgagcatcac aaaaatcgac gctcaagtca    8820
gaggtggcga aacccgacag gactataaag ataccaggcg tttccccctg gaagctccct    8880
cgtgcgctct cctgttccga ccctgccgct taccggatac ctgtccgcct ttctcccttc    8940
gggaagcgtg cgctttctc  atagctcacg ctgtaggtat ctcagttcgg tgtaggtcgt    9000
tcgctccaag ctgggctgtg tgcacgaacc ccccgttcag cccgaccgct gcgccttatc    9060
cggtaactat cgtcttgagt ccaacccggt aagacacgac ttatcgccac tggcagcagc    9120
cactggtaac aggattagca gagcgaggta tgtaggcggt gctacagagt tcttgaagtg    9180
gtggcctaac tacggctaca ctagaagaac agtatttggt atctgcgctc tgctgaagcc    9240
agttaccttc ggaagaagag ttggtagctc ttgatccggc aaacaaacca ccgctggtag    9300
cggtggtttt tttgtttgca agcagcagat tacgcgcaga aaaaaggat  ctcaagaaga    9360 tcctttgatc ttttctacgg ggtctgacgc tcagtggaac gaaaactcac gttaagggat    9420
tttggtcatg agattatcaa aaaggatctt cacctagatc cttttaaatt aaaaatgaag    9480
ttttaaatca atctaaagta tatatgtgta acattggtct agtgattaga aaaactcatc    9540
```

```
gagcatcaaa tgaaactgca atttattcat atcaggatta tcaataccat attttttgaaa    9600 aagccgtttc tgtaatgaag gagaaaactc accgaggcag ttccatagga tggcaagatc    9660
ctggtatcgg tctgcgattc cgactcgtcc aacatcaata caacctatta atttcccctc    9720
gtcaaaaata aggttatcaa gtgagaaatc accatgagtg acgactgaat ccggtgagaa    9780
tggcaaaagt ttatgcattt ctttccagac ttgttcaaca ggccagccat tacgctcgtc    9840
atcaaaatca ctcgcatcaa ccaaaccgtt attcattcgt gattgcgcct gagcgagacg    9900
aaatacgcga tcgctgttaa aaggacaatt acaaacagga atcgaatgca accggcgcag    9960
gaacactgcc agcgcatcaa caatattttc acctgaatca ggatattctt ctaatacctg   10020
gaatgctgtt ttccctggga tcgcagtggt gagtaaccat gcatcatcag gagtacggat   10080
aaaatgcttg atggtcggaa gaggcataaa ttccgtcagc cagtttagtc tgaccatctc   10140
atctgtaaca acattggcaa cgctaccttt gccatgtttc agaaacaact ctggcgcatc   10200
gggcttccca tacaatcggt agattgtcgc acctgattgc ccgacattat cgcgagccca   10260
tttataccca tataaatcag catccatgtt ggaatttaat cgcggccttg agcaagacgt   10320
ttcccgttga atatggctca taacacccct tgtattactg tttatgtaag cagacagttt   10380
tattgttcat gatgatatat ttttatcttg tgcaatgtaa catcagagat tttgagacac   10440
aacgtggctt tgttgaataa atcgaacttt tgctgagttg aaggatcaga tcacgcatct   10500
tcccgacaac gcagaccgtt ccgtggcaaa gcaaaagttc aaaatcacca actggtccac   10560
ctacaacaaa gctctcatca accgtggctc cctcactttc tggctggatg atggggcgat   10620
tcaggcgatc cccatccaac agcccgccgt cgagcgggct tttttatccc cggaagcctg   10680
tggatagagg gtagttatcc acgtgaaacc gctaatgccc cgcaaagcct tgattcacgg   10740
ggctttccgg cccgctccaa aaactatcca cgtgaaatcg ctaatcaggg tacgtgaaat   10800
cgctaatcgg agtacgtgaa atcgctaata aggtcacgtg aaatcgctaa tcaaaaaggc   10860
acgtgagaac gctaatagcc ctttcagatc aacagcttgc aaacacccct cgctccggca   10920
agtagttaca gcaagtagta tgttcaatta gcttttcaat tatgaatata tatatcaatt   10980
attggtcgcc cttggcttgt ggacaatgcg ctacgcgcac cggctccgcc cgtggacaac   11040
cgcaagcggt tgcccaccgt cgagcgccag cgccttttgcc cacaacccgg cggccggccg   11100
caacagatcg ttttataaat ttttttttt gaaaagaaa aagcccgaaa ggcggcaacc   11160
tctcgggctt ctggatttcc gatccccgga attagagatc ttggcaggat atattgtggt   11220
gtaacgttat cagcttgcat gccggtcgat ctagtaacat agatgacacc gcgcgcgata   11280
atttatccta gtttgcgcgc tatattttgt tttctatcgc gtattaaatg tataattgcg   11340
ggactctaat caaaaaaccc atctcataaa taacgtcatg cattacatgt taattattac   11400
atgcttaacg taattcaaca gaaattatat gataatcatc gcaagaccgg caacaggatt   11460
caatcttaag aaactttatt gccaaatgtt tgaacgatct gcttgactct agctagagtc   11520 cgaacccag agtcccgctc agaagaactc gtcaagaagg cgatagaagg cgatgcgctg   11580
cgaatcggga gcggcgatac cgtaaagcac gaggaagcgg tcagcccatt cgccgccaag   11640
ctcttcagca atatcacggg tagccaacgc tatgtcctga tagcggtccg ccacacccag   11700
ccggccacag tcgatgaatc cagaaaagcg gccattttcc accatgatat tcggcaagca   11760
ggcatcgccc tgggtcacga cgagatcctc gccgtcgggc atccgcgcct tgagcctggc   11820
gaacagttcg gctggcgcga gccccctgatg ctcttcgtcc agatcatcct gatcgacaag   11880
```

```
accggcttcc atccgagtac gtcctcgctc gatgcgatgt ttcgcttggt ggtcgaatgg   11940
gcaggtagcc ggatcaagcg tatgcagccg ccgcattgca tcagccatga tggatacttt   12000
ctcggcagga gcaaggtgag atgacaggag atcctgcccc ggcacttcgc ccaatagcag   12060 ccagtcccctt cccgcttcag tgacaacgtc gagcacagct gcgcaaggaa cgcccgtcgt   12120
ggccagccac gatagccgcg ctgcctcgtc ttggagttc                          12159
```

<210> SEQ ID NO 9
<211> LENGTH: 1036
<212> TYPE: DNA
<213> ORGANISM: Artificial sequence
<220> FEATURE:
<223> OTHER INFORMATION: 35S Promoter

<400> SEQUENCE: 9

```
tcgactagaa tagtaaattg taatgttgtt tgttgtttgt tttgttgtgg taattgttgt    60
aaaaatacgg atcgtcctgc agtcctctcc aaatgaaatg aacttcctta tatagaggaa   120
gggtcttgcg aaggatagtg ggattgtgcg tcatccctta cgtcagtgga gatatcacat   180
caatccactt gctttgaaga cgtggttgga acgtcttctt tttccacgat gctcctcgtg   240 ggtggggggtc catctttggg accactgtcg gcagaggcat cttgaacgat agcctttcct   300
ttatcgcaat gatggcattt gtaggtgcca ccttcctttt ctactgtcct tttgatgaag   360
tgacagatag ctgggcaatg gaatccgagg aggtttcccg atattaccct ttgttgaaaa   420
gtctcaatag cccttttggtc ttctgagact gtatctttga tattcttgga gtagacgaga   480
gtgtcgtgct ccaccatgtt gacgaagatt ttcttcttgt cattgagtcg taaaagactc   540
tgtatgaact gttcgccagt cttcacggcg agttctgtta atcctcgat ctgaattttt   600 gactccatgg cctttgattc agtaggaact actttcttag agactccaat ctctattact   660
tgccttggtt tatgaagcaa gccttgaatc gtccatactg gaatagtact tctgatcttg   720
agaaatatat ctttctctgt gttcttgatg cagttagtcc tgaatctttt gactgcatct   780
ttaaccttct tgggaaggta tttgatctcc tggagattat tactcgggta gatcgtcttg   840
atgagacctg ccgcgtaggc ctctctaacc atctgtgggt cagcattctt tctgaaattg   900
aagaggctaa tcttctcatt atcggtggtg aacatggtat cgtcaccttc tccgtcgaac   960
tttcttccta gatcgtagag atagagaaag tcgtccatgg tgatctccgg ggcaaggag  1020 atcagcttgg ctctag                                                 1036
```

<210> SEQ ID NO 10
<211> LENGTH: 333
<212> TYPE: DNA
<213> ORGANISM: Artificial sequence
<220> FEATURE:
<223> OTHER INFORMATION: AlcA promoter

<400> SEQUENCE: 10

```
ccgacctagg attggatgca tgcggaaccg cacgagggcg gggcggaaat tgacacacca    60
ctcctctcca cgcagccgtt caagaggtac gcgtatagag ccgtatagag cagagacgga   120
gcactttctg gtactgtccg cacggatgt ccgcacggag agccacaaac gagcggggcc    180
ccgtacgtgc tctcctaccc caggatcgca tcctcgcata gctgaacatc tatataagga   240
agttcatttc atttggagag gacacgctga aatcaccagt ctctctctac aaatctatct   300
ctctcgagct ttcgcagatc ccggggagta ctc                               333
```

<210> SEQ ID NO 11
<211> LENGTH: 1023
<212> TYPE: DNA
<213> ORGANISM: Artificial sequence
<220> FEATURE:
<223> OTHER INFORMATION: RBC Promoter

<400> SEQUENCE: 11

| | |
|---|---|
| aagcttgtgg gaacgagata agggcgaagt gcgctagtag cctgctattt aaaatatatc | 60 |
| cacaatttat aatgtatttg aagattagtc aattcgtcca aaattcagga ctaagtatct | 120 |
| tgaattttg tatcctgaat ttttgggcta ctaatttgga actcaggact taatgtccta | 180 |
| aattttgag ccgctaattt gaaattcagg actaagtgtt ttgaattttt gaactgctta | 240 |
| ttcgaaatgc aagactaagt gacatgaatt tttgaactgc taatttaaaa ttcaggacat | 300 |
| aagatttgaa ttttcaaaca taattttttta actttagggc acgatgtcct gaagtttgaa | 360 |
| tcttgagatc taaacttcaa gatgcagcgt cttgaagttt gagtgaactg ctaatctttt | 420 |
| aaatacttgt aaactgtgga tacatttta aataatatat ttaaaagcgg ctacctggta | 480 |
| tcatcttcac gagaattttc caagttaatt gtaaaggaaa tagtggtgtt gcatcaagtt | 540 |
| atggacaata taaggaagca aacagtactc tagctatcaa attagtttcc acttctaaac | 600 |
| catgaatatt aggaaaaaca agaaacaaaa caaatataca taaacaatac ggctaaagcc | 660 |
| aaggaaaagg gactctaaaa aaattaacca acctcaatca cacattcata tcctcttcct | 720 |
| accccatcta ggatgagata agattactag gtcttacacg tggcacctcc attgtggtga | 780 |
| ctaaatgaag agtggcttag ctcaaaatat aattttccaa cctttcatgt gtggatatta | 840 |
| agttttgtgt agtgaatcaa gaaccacata atccaatggt tagctttatt ccaagatgag | 900 |
| ggggttgttg attttttgtcc gtcagatata ggaaatatgt aaaaccttat cattatatat | 960 |
| agggtggtgg gcaactatgc aatgaccata ttggaagtta aggaaaaga gagaaagaga | 1020 |
| aat | 1023 |

<210> SEQ ID NO 12
<211> LENGTH: 5057
<212> TYPE: DNA
<213> ORGANISM: Artificial sequence
<220> FEATURE:
<223> OTHER INFORMATION: AlcR fragment with required 35S Promoter

<400> SEQUENCE: 12

| | |
|---|---|
| catggtggag cacgacactc tcgtctactc caagaatatc aaagatacag tctcagaaga | 60 |
| ccaaagggct attgagactt ttcaacaaag ggtaatatcg ggaaacctcc tcggattcca | 120 |
| ttgcccagct atctgtcact tcatcaaaag gacagtagaa aaggaaggtg cacctacaa | 180 |
| atgccatcat tgcgataaag gaaaggctat cgttcaagat gcctctgccg acagtggtcc | 240 |
| caaagatgga cccccaccca cgaggagcat cgtggaaaaa gaagacgttc caaccacgtc | 300 |
| ttcaaagcaa gtggattgat gtgataacat ggtggagcac gacactctcg tctactccaa | 360 |
| gaatatcaaa gatacagtct cagaagacca aagggctatt gagacttttc aacaaagggt | 420 |
| aatatcggga aacctcctcg gattccattg cccagctatc tgtcacttca tcaaaaggac | 480 |
| agtagaaaag gaaggtggca cctacaaatg ccatcattgc gataaaggaa aggctatcgt | 540 |
| tcaagatgcc tctgccgaca gtggtcccaa agatggaccc ccacccacga ggagcatcgt | 600 |
| ggaaaaagaa gacgttccaa ccacgtcttc aaagcaagtg gattgatgtg atatctccac | 660 |
| tgacgtaagg gatgacgcac aatcccacta tccttcgcaa gaccttcctc tatataagga | 720 |

-continued

```
agttcatttc atttggagag dacacgctga aatcaccagt ctctctctac aaatctatct    780
ctctcgagct ttcgcagatc ccggggagta ctatgtgctg aaccccgca tgctccaggc     840
ctcattcccc agatttcgac tccatggctg acagcatcca gaccgcacgt ttttggactt    900
ctgataccat ctatacagat atcactgtcg atattctcct gcacacagca tggcagatac    960
gcgccgacgc cagaatcata gctgcgatcc ctgtcgcaag ggcaagcgac gctgtgatgc   1020
cccgaaacga ggccaatgaa aacggctggg tttcgtgttc aaattgcaag cgttggaaca   1080
aggattgtac cttcaattgg ctctcatccc aacgctccaa ggcaaaaggg gctgcaccta   1140
gagcgagaac aaagaaagcc aggaccgcaa caaccaccag tgaaccatca acttcagctg   1200
caacaatccc tacaccggaa agtgacaatc acgatgcgcc tccagtcata aactctcacg   1260
acgcgctccc gagctggact cagggctac tctcccaccc cggcgacctt ttcgatttca    1320
gccactctgc tattcccgca aatgcagaag atgcggccaa cgtgcagtca gacgcacctt   1380
ttccgtggga tctagccatc cccggtgatt tcagcatggg ccaacagctc gagaaacctc   1440
tcagtccgct cagttttcaa gcagtccttc ttccgcccca tagcccgaac acggatgacc   1500
tcattcgcga gctggaagag cagactacgg atccggactc ggttaccgat actaatagtg   1560
tacaacaggt cgctcaagat ggatcgctat ggtctgatcg gcagtcgccg ctactgcctg   1620
agaacagtct gtgcatggcc tcagacagca cagcacggcg atatgcccgt tccacaatga   1680
cgaagaatct gatgcgaatc taccacgata gtatggagaa tgcactgtcc tgctggctga   1740
cagagcacaa ttgtccatac tccgaccaga tcagctacct gccgcccaag cagcgggcgg   1800
aatgggcccc gaactggtca aacaggatgt gcatccgggt gtgccggcta gatcgcgtat   1860
ctacctcatt acgcgggcgc gccctgagtg cggaagagga caaagccgca gcccgagccc   1920
tgcatctggc gatcgtagct tttgcgtcgc aatggacgca gcatgcgcag agggggggctg   1980
ggctaaatgt tcctgcagac atagccgccg atgagaggtc catccggagg aacgcctgga   2040
atgaagcacg ccatgccttg cagcacacga cagggattcc atcattccgg gttatatttg   2100
cgaatatcat cttttctctc acgcagagtg tgctggatga tgatgagcag cacggtatgg   2160
gtgcacgtct agacaagcta ctcgaaaatg acggtgcgcc cgtgttcctg gaaaccgcga   2220
accgtcagct ttatacattc cgacataagt ttgcacgaat gcaacgccgc ggtaaggctt   2280
tcaacaggct cccggagga tctgtcgcat cgacattcgc cggtattttc gagacaccga    2340
cgccgtcgtc tgaaagccca cagcttgacc cggttgtggc cagtgaggag catcgcagta   2400
cattaagcct tatgttctgg ctagggatca tgttcgatac actaagcgct gcaatgtacc   2460
agcgaccact cgtggtgtca gatgaggata gccagatatc atcggcatct ccaccaaggc   2520
gcggcgctga aacgccgatc aacctagact gctgggagcc cccagacag gtcccgagca    2580
atcaagaaaa gagcgacgta tggggcgacc tcttcctccg cacctcggac tctctcccag   2640
atcacgaatc ccacacacaa atctctcagc cagcggctcg atggccctgc acctacgaac   2700
aggccgccgc cgctctctcc tctgcaacgc ccgtcaaagt cctcctctac cgccgcgtca   2760
cgcagctcca aaccctcctc tatcgcggcg ccagccctgc ccgccttgaa gcggccatcc   2820
agagaacgct ctacgtttat aatcactgga cagcgaagta ccaaccattt atgcaggact   2880
gcgttgctaa ccacgagctc ctcccttcgc gcatccagtc ttggtacgtc attctagacg   2940
gtcactggca tctagccgcg atgttgctag cggacgtttt ggagagcatc gaccgcgatt   3000
cgtactctga tatcaaccac atcgaccttg taacaaagct aaggctcgat aatgcactag   3060
cagttagtgc ccttgcgcgc tcttcactcc gaggccagga gctggacccg ggcaaagcat   3120
```

```
ctccgatgta tcgccatttc catgattctc tgaccgaggt ggcattcctg gtagaaccgt    3180
ggaccgtcgt tcttattcac tcgtttgcca aagctgcgta tatcttgctg gactgtttag    3240
atctggacgg ccaaggaaat gcactagcgg ggtacctgca gctgcggcaa aattgcaact    3300
actgcattcg ggcgctgcaa tttctgggca ggaagtcgga tatggcggcg ctggttgcga    3360
aggatttaga gagaggtttg aatgggaaag ttgacagctt tttgtacata ctccgaccag    3420
atcagctacc tgccgcccaa gcagcgggcg gaatggggcc cgaactggtc aaacaggatg    3480
tgcatccggg tgtgccggct agatcgcgta tctacctcat tacgcgggcg cgccctgagt    3540
gcggaagagg acaaagccgc agcccgagcc ctgcatctgg cgatcgtagc ttttgcgtcg    3600
caatggacgc agcatgcgca gagggggct gggctaaatg ttcctgcaga catagccgcc     3660
gatgagaggt ccatccggag gaacgcctgg aatgaagcac gccatgcctt gcagcacacg    3720
acagggattc catcattccg ggttatattt gcgaatatca tcttttctct cacgcagagt    3780
gtgctggatg atgatgagca gcacggtatg ggtgcacgtc tagacaagct actcgaaaat    3840
gacggtgcgc ccgtgttcct ggaaaccgcg aaccgtcagc tttatacatt ccgacataag    3900
tttgcacgaa tgcaacgccg cggtaaggct ttcaacaggc tcccgggagg atctgtcgca    3960
tcgacattcg ccggtatttt cgagacaccg acgccgtcgt ctgaaagccc acagcttgac    4020
ccggttgtgg ccagtgagga gcatcgcagt acattaagcc ttatgttctg gctagggatc    4080
atgttcgata cactaagcgc tgcaatgtac cagcgaccac tcgtggtgtc agatgaggat    4140
agccagatat catcggcatc tccaccaagg cgcggcgctg aaacgccgat caacctagac    4200
tgctgggagc ccccgagaca ggtcccgagc aatcaagaaa agagcgacgt atgggcgac     4260
ctcttcctcc gcacctcgga ctctctccca gatcacgaat cccacacaca aatctctcag    4320
ccagcggctc gatggccctg cacctacgaa caggccgccg ccgctctctc ctctgcaacg    4380
cccgtcaaag tcctcctcta ccgccgcgtc acgcagctcc aaaccctcct ctatcgcggc    4440
gccagccctg cccgccttga agcggccatc cagagaacgc tctacgttta taatcactgg    4500
acagcgaagt accaaccatt tatgcaggac tgcgttgcta ccacgagct cctcccttcg     4560
cgcatccagt cttggtacgt cattctagac ggtcactggc atctagccgc gatgttgcta    4620
gcggacgttt tggagagcat cgaccgcgat tcgtactctg atatcaacca catcgaccit    4680
gtaacaaagc taaggctcga taatgcacta gcagttagtg cccttgcgcg ctcttcactc    4740
cgaggccagg agctggaccc gggcaaagca tctccgatgt atcgccattt ccatgattct    4800
ctgaccgagg tggcattcct ggtagaaccg tggaccgtcg ttcttattca ctcgtttgcc    4860
aaagctgcgt atatcttgct ggactgttta gatctggacg gccaaggaaa tgcactagcg    4920
gggtacctgc agctgcggca aaattgcaac tactgcattc gggcgctgca atttctgggc    4980
aggaagtcgg atatggcggc gctggttgcg aaggatttag agagaggttt gaatgggaaa    5040
gttgacagct ttttgta                                                   5057
```

<210> SEQ ID NO 13
<211> LENGTH: 19
<212> TYPE: DNA
<213> ORGANISM: Artificial sequence
<220> FEATURE:
<223> OTHER INFORMATION: Promoter

<400> SEQUENCE: 13

```
aaaggaaggt ggctcctac                                                    19
```

```
<210> SEQ ID NO 14
<211> LENGTH: 20
<212> TYPE: DNA
<213> ORGANISM: Artificial Sequence
<220> FEATURE:
<223> OTHER INFORMATION: Promoter

<400> SEQUENCE: 14
ccatctttgc ccttgaagtc                                              20

<210> SEQ ID NO 15
<211> LENGTH: 25
<212> TYPE: DNA
<213> ORGANISM: Artificial Sequence
<220> FEATURE:
<223> OTHER INFORMATION: Promoter

<400> SEQUENCE: 15
ggagttcctc cacttcagca acggc                                        25

<210> SEQ ID NO 16
<211> LENGTH: 21
<212> TYPE: DNA
<213> ORGANISM: Artificial Sequence
<220> FEATURE:
<223> OTHER INFORMATION: Promoter

<400> SEQUENCE: 16
ctacgaggag cacccacccc c                                            21

<210> SEQ ID NO 17
<211> LENGTH: 18
<212> TYPE: DNA
<213> ORGANISM: Artificial Sequence
<220> FEATURE:
<223> OTHER INFORMATION: Promoter

<400> SEQUENCE: 17
aaggaaaggc catcgttg                                                18

<210> SEQ ID NO 18
<211> LENGTH: 20
<212> TYPE: DNA
<213> ORGANISM: Artificial Sequence
<220> FEATURE:
<223> OTHER INFORMATION: Promoter

<400> SEQUENCE: 18
caaatacgca ggaactgagg                                              20

<210> SEQ ID NO 19
<211> LENGTH: 20
<212> TYPE: DNA
<213> ORGANISM: Artificial Sequence
<220> FEATURE:
<223> OTHER INFORMATION: Promoter

<400> SEQUENCE: 19
gagcagtgga tggaagtaag                                              20

<210> SEQ ID NO 20
<211> LENGTH: 18
<212> TYPE: DNA
<213> ORGANISM: Artificial Sequence
<220> FEATURE:
<223> OTHER INFORMATION: Promoter
```

<400> SEQUENCE: 20
actttagggc acgatgtc                                                    18

<210> SEQ ID NO 21
<211> LENGTH: 18
<212> TYPE: DNA
<213> ORGANISM: Artificial Sequence
<220> FEATURE:
<223> OTHER INFORMATION: Promoter

<400> SEQUENCE: 21
ctatcaccgt gccaatag                                                    18

<210> SEQ ID NO 22
<211> LENGTH: 20
<212> TYPE: DNA
<213> ORGANISM: Artificial Sequence
<220> FEATURE:
<223> OTHER INFORMATION: Promoter

<400> SEQUENCE: 22
gagccgtata gagcagagac                                                  20

<210> SEQ ID NO 23
<211> LENGTH: 850
<212> TYPE: DNA
<213> ORGANISM: Artificial Sequence
<220> FEATURE:
<223> OTHER INFORMATION: Cpn 21 Antisense

<400> SEQUENCE: 23
cacacgtgcc agattatgct caggccgttt acggaaaaaa tttccacaat tgggatacaa      60
gttgcagatt acaaagatat aacataacta agaaagtata gccatcacat ctgaagctct     120
gagggcaatg tagttggaac catctttgcc cttgaagtcg ttaccagcat acttggagta     180
aagtactgtg cttccggttg atactggtag aggcgtaatt ttaccttcct cgtctaggga     240
acccggtcca actgctatca ccgtgccaat agaaggcttc tctttggtag tctcggttaa     300
caacaaccct ccagctgttt tctcctccgc ctcagcaacc ttaataaaga ctcggtcatt     360
caaaggtttg agatctttga tgtcctctgt ctcaagaatg ccaacaatat catcttcctt     420
gaggataaga tgcttcacat cattgaactc cacctcagtt cctgcgtatt tggagtagat     480
aatttgtgct ccagtaggga cagtgatatc aattttgttc ttcccaatag ttcttccttc     540
acccacggca acgacttcac ctccttgagg ttttgattga gcagtggatg gaagtaagat     600
accacctaaa gtcttctcct ctgcctcctt gatcttcacc aaaactcgat ctcccaatgg     660
cttaattgaa gtatacttag gggcaacaac agaagcagct tgacaaccaa acgacggaa     720 ctggctctgt ctaagggtcc ctggtttcaa agatgaaaac ttgacactcg aagctctgag     780
accatccagc gaggctaagc tccttgctga catagtcact ggtgacgctg taagttgagt     840
cgccgccatt                                                            850

<210> SEQ ID NO 24
<211> LENGTH: 53
<212> TYPE: DNA
<213> ORGANISM: Artificial Sequence
<220> FEATURE:
<223> OTHER INFORMATION: Promoter

<400> SEQUENCE: 24

```
ggggaccact tgtacaaga aagctgggtg ggaggcagag gagaagactt tag          53
```

<210> SEQ ID NO 25
<211> LENGTH: 54
<212> TYPE: DNA
<213> ORGANISM: Artificial Sequence
<220> FEATURE:
<223> OTHER INFORMATION: Promoter

<400> SEQUENCE: 25

```
ggggacaagt ttgtacaaaa aagcaggctg gcttccggtt gatactggta gagg        54
```

<210> SEQ ID NO 26
<211> LENGTH: 30
<212> TYPE: DNA
<213> ORGANISM: Artificial Sequence
<220> FEATURE:
<223> OTHER INFORMATION: Promoter

<400> SEQUENCE: 26

```
ggcacgtgaa atggcggcga ctcaacttac                                   30
```

<210> SEQ ID NO 27
<211> LENGTH: 32
<212> TYPE: DNA
<213> ORGANISM: Artificial Sequence
<220> FEATURE:
<223> OTHER INFORMATION: Promoter

<400> SEQUENCE: 27

```
ggactagtcc agattatgct caggccgttt ac                                32
```

<210> SEQ ID NO 28
<211> LENGTH: 6155
<212> TYPE: DNA
<213> ORGANISM: Artificial Sequence
<220> FEATURE:
<223> OTHER INFORMATION: pGreen0029-RBC

<400> SEQUENCE: 28

```
attcagggca ccggacaggt cggtcttgac aaaaagaacc gggcgcccct gcgctgacag    60
ccggaacacg gcggcatcag agcagccgat tgtctgttgt gcccagtcat agccgaatag   120
cctctccacc caagcggccg gagaacctgc gtgcaatcca tcttgttcaa tcatgcctcg   180
atcgagttga gagtgaatat gagactctaa ttggataccg agggaattt atggaacgtc    240
agtggagcat ttttgacaag aaatatttgc tagctgatag tgaccttagg cgacttttga   300
acgcgcaata atggtttctg acgtatgtgc ttagctcatt aaactccaga aacccgcggc   360
tgagtggctc cttcaacgtt gcggttctgt cagttccaaa cgtaaaacgg cttgtcccgc   420
gtcatcggcg ggggtcataa cgtgactccc ttaattctca tgtatcgata acattaacgt   480
ttacaatttc gcgccattcg ccattcaggc tgcgcaactg ttgggaaggg cgatcggtgc   540
gggcctcttc gctattacgc cagctggcga aggggggatg tgctgcaagg cgattaagtt   600
gggtaacgcc agggttttcc cagtcacgac gttgtaaaac gacggccagt gaattgtaat   660
acgactcact atagggcgaa ttgggtacct ctgcagataa gcttgtggga acgagataag   720
ggcgaagtgc gctagtagcc tgctatttaa aatatatcca caatttataa tgtatttgaa   780
gattagtcaa ttcgtccaaa attcaggact aagtatcttg aattttgta tcctgaattt    840
ttgggctact aatttggaac tcaggactta atgtcctaaa ttttgagcc gctaatttga   900
aattcaggac taagtgtttt gaattttga actgcttatt cgaaatgcaa gactaagtga   960
```

```
catgaatttt tgaactgcta atttaaaatt caggacataa gatttgaatt ttcaaacata   1020 atttttaac tttagggcac gatgtcctga agtttgaatc ttgagatcta aacttcaaga   1080
tgcagcgtct tgaagtttga gtgaactggc taatctttaa atacttgtaa actgtggata   1140 cattttaaa taatatattt aaaagcggct acctggtatc atcttcacga aattttcca    1200 agttaattgt aaaggaaata gtggtgttgc atcaagttat ggacaatata aggaagcaaa   1260
cagtactcta gctatcaaat tagtttccac ttctaaacca tgaatattag gaaaacaag   1320 aaacaaaaca aatatacata aacaatacgg ctaaagccaa ggaaaaggga ctctaaaaaa   1380
attaaccaac ctcaatcaca cattcatatc ctcttcctac cccatctagg atgagataag   1440
attactaggt cttacacgtg gcacctccat tgtggtgact aaatgaagag tggcttagct   1500
caaaatataa ttttccaacc tttcatgtgt ggatattaag ttttgtgtag tgaatcaaga   1560
accacataat ccaatggtta gctttattcc aagatgaggg ggttgttgat ttttgtccgt   1620
cagatatagg aaatatgtaa aaccttatca ttatatatag ggtggtgggc aactatgcaa   1680
tgaccatatt ggaagttaaa ggaaaagaga gaaagagaaa tctttctgtc taagtgtaat   1740
taacttctag atacatgtct cgagcggccg ccagtgtgat ggatatcgaa ttcgcccttg   1800
gatcctcact agtggatccg agctcatcga taagcttggc gtcgatcgtt caaacatttg   1860
gcaataaagt ttcttaagat tgaatcctgt tgccggtctt gcgatgatta tcatataatt   1920
tctgttgaat tacgttaagc atgtaataat taacatgtaa tgcatgacgt tatttatgag   1980 atgggtttt atgattagag tcccgcaatt atacatttaa tacgcgatag aaaacaaaat   2040
atagcgcgca aactaggata aattatcgcg cgcggtgtca tctatgttac tagatcgggg   2100
aattgatccc ccctcgacag cttcccatgg tccccgggga gggcccccc tcgaggtcga   2160 cggtatcgat aagcttgata tcgaattcct gcagcccggg ggatccacta gttctagagc   2220
ggccgccacc gcggtggagc tccagctttt gttcccttta gtgagggtta attccgagct   2280
tggcgtaatc atggtcatag ctgtttcctg tgtgaaattg ttatccgctc acaattccac   2340
acaacatacg agccggaagh cataaagtgt aaagcctggg gtgcctaatg agtgagctaa   2400
ctcacattaa ttgcgttgcg ctcactgccc gctttccagt cgggaaacct gtcgtgccag   2460
ctgcattaat gaatcggcca acgcgcgggg agaggcggtt tgcgtattgg gcgctcttcc   2520
gcttcctcgc tcactgactc gctgcgctcg gtcgttcggc tgcggcgagc ggtatcagct   2580
cactcaaagg cggtaatacg gttatccaca gaatcagggg ataacgcagg aaagaacatg   2640
aaggccttga caggatatat tggcgggtaa actaagtcgc tgtatgtgtt tgtttgagat   2700
ctcatgtgag caaaaggcca gcaaaaggcc aggaaccgta aaaaggccgc gttgctggcg   2760
tttttccata ggctccgccc ccctgacgag catcacaaaa atcgacgctc aagtcagagg   2820
tggcgaaacc cgacaggact ataaagatac caggcgtttc ccctggaag ctccctcgtg   2880 cgctctcctg ttccgaccct gccgcttacc ggatacctgt ccgcctttct cccttcggga   2940
agcgtggcgc tttctcatag ctcacgctgt aggtatctca gttcggtgta ggtcgttcgc   3000
tccaagctgg gctgtgtgca cgaaccccc gttcagcccg accgctgcgc cttatccggt   3060
aactatcgtc ttgagtccaa cccggtaaga cacgacttat cgccactggc agcagccact   3120
ggtaacagga ttagcagagc gaggtatgta ggcggtgcta cagagttctt gaagtggtgg   3180
cctaactacg gctacactag aagaacagta tttggtatct gcgctctgct gaagccagtt   3240
accttcggaa gaagagttgg tagctcttga tccggcaaac aaaccaccgc tggtagcggt   3300
```

```
ggttttttg tttgcaagca gcagattacg cgcagaaaaa aaggatctca agaagatcct    3360
ttgatcttt ctacggggtc tgacgctcag tggaacgaaa actcacgtta agggattttg    3420
gtcatgagat tatcaaaaag gatcttcacc tagatccttt taaattaaaa atgaagtttt   3480
aaatcaatct aaagtatata tgtgtaacat tggtctagtg attagaaaaa ctcatcgagc   3540
atcaaatgaa actgcaattt attcatatca ggattatcaa taccatattt ttgaaaaagc   3600
cgtttctgta atgaaggaga aaactcaccg aggcagttcc ataggatggc aagatcctgg    3660
tatcggtctg cgattccgac tcgtccaaca tcaatacaac ctattaattt ccctcgtca    3720
aaaataaggt tatcaagtga gaaatcacca tgagtgacga ctgaatccgg tgagaatggc   3780
aaaagtttat gcatttcttt ccagacttgt tcaacaggcc agccattacg ctcgtcatca    3840
aaatcactcg catcaaccaa accgttattc attcgtgatt gcgcctgagc gagacgaaat    3900
acgcgatcgc tgttaaaagg acaattacaa acaggaatcg aatgcaaccg cgcaggaac    3960
actgccagcg catcaacaat attttcacct gaatcaggat attcttctaa tacctggaat   4020
gctgttttcc ctgggatcgc agtggtgagt aaccatgcat catcaggagt acggataaaa    4080
tgcttgatgg tcggaagagg cataaattcc gtcagccagt ttagtctgac catctcatct   4140
gtaacaacat tggcaacgct acctttgcca tgtttcagaa acaactctgg cgcatcgggc   4200
ttcccataca atcggtagat tgtcgcacct gattgcccga cattatcgcg agcccattta    4260
tacccatata aatcagcatc catgttggaa tttaatcgcg gccttgagca agacgtttcc   4320
cgttgaatat ggctcataac accccttgta ttactgttta tgtaagcaga cagttttatt    4380
gttcatgatg atatattttt atcttgtgca atgtaacatc agagattttg agacacaacg    4440
tggctttgtt gaataaatcg aacttttgct gagttgaagg atcagatcac gcatcttccc   4500
gacaacgcag accgttccgt ggcaaagcaa aagttcaaaa tcaccaactg gtccacctac   4560
aacaaagctc tcatcaaccg tggctccctc actttctggc tggatgatgg ggcgattcag   4620
gcgatcccca tccaacagcc cgccgtcgag cgggcttttt tatccccgga agcctgtgga    4680
tagagggtag ttatccacgt gaaaccgcta atgccccgca aagccttgat tcacggggct   4740
ttccggcccg ctccaaaaac tatccacgtg aaatcgctaa tcagggtacg tgaaatcgct   4800
aatcggagta cgtgaaatcg ctaataaggt cacgtgaaat cgctaatcaa aaaggcacgt   4860
gagaacgcta atagcccttt cagatcaaca gcttgcaaac accctcgct ccggcaagta     4920
gttacagcaa gtagtatgtt caattagctt ttcaattatg aatatatata tcaattattg   4980
gtcgcccttg gcttgtggac aatgcgctac gcgcaccggc tccgcccgtg acaaccgca    5040
agcggttgcc caccgtcgag cgccagcgcc tttgcccaca acccggcggc cggccgcaac    5100
agatcgtttt ataattttt tttttgaaa agaaaaagc ccgaaaggcg gcaacctctc       5160
gggcttctgg atttccgatc cccggaatta gagatcttgg caggatatat tgtggtgtaa   5220
cgttatcagc ttgcatgccg gtcgatctag taacatagat gacaccgcgc gcgataattt   5280
atcctagttt gcgcgctata ttttgttttc tatcgcgtat taaatgtata attgcgggac    5340
tctaatcaaa aaacccatct cataaataac gtcatgcatt acatgttaat tattacatgc    5400
ttaacgtaat tcaacagaaa ttatatgata atcatcgcaa gaccggcaac aggattcaat    5460
cttaagaaac tttattgcca aatgtttgaa cgatctgctt gactctagct agagtccgaa    5520
ccccagagtc ccgctcagaa gaactcgtca agaaggcgat agaaggcgat gcgctgcgaa    5580
tcgggagcgg cgataccgta aagcacgagg aagcggtcag cccattcgcc gccaagctct    5640
tcagcaatat cacgggtagc caacgctatg tcctgatagc ggtccgccac acccagccgg    5700
```

```
ccacagtcga tgaatccaga aaagcggcca ttttccacca tgatattcgg caagcaggca    5760
tcgccctggg tcacgacgag atcctcgccg tcgggcatcc gcgccttgag cctggcgaac    5820
agttcggctg gcgcgagccc ctgatgctct tcgtccagat catcctgatc gacaagaccg    5880
gcttccatcc gagtacgtcc tcgctcgatg cgatgtttcg cttggtggtc gaatgggcag    5940
gtagccggat caagcgtatg cagccgccgc attgcatcag ccatgatgga tactttctcg    6000
gcaggagcaa ggtgagatga caggagatcc tgccccggca cttcgcccaa tagcagccag    6060
tcccttcccg cttcagtgac aacgtcgagc acagctgcgc aaggaacgcc cgtcgtggcc    6120
agccacgata gccgcgctgc ctcgtcttgg agttc                               6155
```

<210> SEQ ID NO 29
<211> LENGTH: 3899
<212> TYPE: DNA
<213> ORGANISM: Artificial Sequence
<220> FEATURE:
<223> OTHER INFORMATION: pUC57-RBC

<400> SEQUENCE: 29

```
tatgggtac ctctgcagat aagcttgtgg gaacgagata agggcgaagt gcgctagtag      60
cctgctattt aaaatatatc cacaatttat aatgtatttg aagattagtc aattcgtcca    120
aaattcagga ctaagtatct tgaattttttg tatcctgaat ttttgggcta ctaatttgga    180
actcaggact taatgtccta attttttgag ccgctaattt gaaattcagg actaagtgtt    240
ttgaattttt gaactgctta ttcgaaatgc aagactaagt gacatgaatt tttgaactgc    300
taatttaaaa ttcaggacat aagatttgaa ttttcaaaca taattttta actttagggc    360 acgatgtcct gaagtttgaa tcttgagatc taaacttcaa gatgcagcgt cttgaagttt    420
gagtgaactg gctaatcttt aaatacttgt aaactgtgga tacatttta aataatatat    480 ttaaaagcgg ctacctggta tcatcttcac gagaattttc caagttaatt gtaaaggaaa    540
tagtggtgtt gcatcaagtt atggacaata taaggaagca aacagtactc tagctatcaa    600
attagtttcc acttctaaac catgaatatt aggaaaaaca agaaacaaaa caatatataca    660 taaacaatac ggctaaagcc aaggaaaagg gactctaaaa aaattaacca acctcaatca    720
cacattcata tcctcttcct accccatcta ggatgagata agattactag gtcttacacg    780
tggcacctcc attgtggtga ctaaatgaag agtggcttag ctcaaaatat aattttccaa    840
cctttcatgt gtggatatta agttttgtgt agtgaatcaa gaaccacata atccaatggt    900
tagctttatt ccaagatgag gggttgttg attttttgtcc gtcagatata ggaaatatgt    960
aaaaccttat cattatatat agggtggtgg gcaactatgc aatgaccata ttggaagtta   1020
aaggaaaaga gagaaagaga aatctttctg tctaagtgta attaacttct agatacatgt   1080
ctcgagcggc cgccagtgtg atggatatcg aattcgccct tggatcctca ctagtggatc   1140
cgagctcatc gataagcttg gcgtcgatcg ttcaaacatt tggcaataaa gtttcttaag   1200
attgaatcct gttgccggtc ttgcgatgat tatcatataa tttctgttga attacgttaa   1260
gcatgtaata attaacatgt aatgcatgac gttatttatg agatgggttt ttatgattag   1320
agtcccgcaa ttatacattt aatacgcgat agaaaacaaa atatagcgcg caaactagga   1380
taaattatcg cgcgcggtgt catctatgtt actagatcgg ggaattgatc cccctcgac    1440 agcttcccat ggtccccggg gagggccggg catgcaagct tggcgtaatc atggtcatag   1500
ctgtttcctg tgtgaaattg ttatccgctc acaattccac acaacatacg agccggaagc   1560
```

```
ataaagtgta aagcctgggg tgcctaatga gtgagctaac tcacattaat tgcgttgcgc   1620
tcactgcccg ctttccagtc gggaaacctg tcgtgccagc tgcattaatg aatcggccaa   1680
cgcgcgggga gaggcggttt gcgtattggg cgctcttccg cttcctcgct cactgactcg   1740
ctgcgctcgg tcgttcggct gcggcgagcg gtatcagctc actcaaaggc ggtaatacgg   1800
ttatccacag aatcagggga taacgcagga agaacatgt gagcaaaagg ccagcaaaag   1860
gccaggaacc gtaaaaaggc cgcgttgctg gcgtttttcc ataggctccg ccccctgac    1920
gagcatcaca aaaatcgacg ctcaagtcag aggtggcgaa acccgacagg actataaaga   1980
taccaggcgt ttccccctgg aagctccctc gtgcgctctc ctgttccgac cctgccgctt   2040
accggatacc tgtccgcctt tctcccttcg ggaagcgtgg cgctttctca tagctcacgc   2100
tgtaggtatc tcagttcggt gtaggtcgtt cgctccaagc tgggctgtgt gcacgaaccc   2160
cccgttcagc ccgaccgctg cgccttatcc ggtaactatc gtcttgagtc caacccggta   2220
agacacgact tatcgccact ggcagcagcc actggtaaca ggattagcag agcgaggtat   2280
gtaggcggtg ctacagagtt cttgaagtgg tggcctaact acggctacac tagaagaaca   2340
gtatttggta tctgcgctct gctgaagcca gttaccttcg gaaaaagagt tggtagctct   2400
tgatccggca aacaaaccac cgctggtagc ggtggttttt ttgtttgcaa gcagcagatt   2460
acgcgcagaa aaaaggatc tcaagaagat cctttgatct tttctacggg gtctgacgct   2520
cagtggaacg aaaactcacg ttaagggatt ttggtcatga gattatcaaa aaggatcttc   2580
acctagatcc ttttaaatta aaaatgaagt tttaaatcaa tctaaagtat atatgagtaa   2640
acttggtctg acagttacca atgcttaatc agtgaggcac ctatctcagc gatctgtcta   2700
tttcgttcat ccatagttgc ctgactcccc gtcgtgtaga taactacgat acgggagggc   2760
ttaccatctg gccccagtgc tgcaatgata ccgcgagacc cacgctcacc ggctccagat   2820
ttatcagcaa taaaccagcc agccggaagg gccgagcgca gaagtggtcc tgcaacttta   2880
tccgcctcca tccagtctat taattgttgc cgggaagcta gagtaagtag ttcgccagtt   2940
aatagtttgc gcaacgttgt tgccattgct acaggcatcg tggtgtcacg ctcgtcgttt   3000
ggtatggctt cattcagctc cggttcccaa cgatcaaggc gagttacatg atcccccatg   3060
ttgtgcaaaa aagcggttag ctccttcggt cctccgatcg ttgtcagaag taagttggcc   3120
gcagtgttat cactcatggt tatggcagca ctgcataatt ctcttactgt catgccatcc   3180
gtaagatgct tttctgtgac tggtgagtac tcaaccaagt cattctgaga atagtgtatg   3240
cggcgaccga gttgctcttg cccggcgtca tacgggata ataccgcgcc acatagcaga   3300
actttaaaag tgctcatcat tggaaaacgt tcttcgggc gaaaactctc aaggatctta   3360
ccgctgttga tccagttc gatgtaaccc actcgtgcac ccaactgatc ttcagcatct   3420
tttactttca ccagcgtttc tgggtgagca aaaacaggaa ggcaaaatgc cgcaaaaaag   3480
ggaataaggg cgacacggaa atgttgaata ctcatactct tccttttca atattattga   3540
agcatttatc agggttattg tctcatgagc ggatacatat ttgaatgtat ttagaaaaat   3600
aaacaaatag gggttccgcg cacatttccc cgaaaagtgc cacctgacgt ctaagaaacc   3660
attattatca tgacattaac ctataaaaat aggcgtatca cgaggccctt tcgtctcgcg   3720
cgtttcggtg atgacggtga aaacctctga cacatgcagc tcccggagac ggtcacagct   3780
tgtctgtaag cggatgccgg gagcagacaa gcccgtcagg gcgcgtcagc gggtgttggc   3840
gggtgtcggg gctggcttaa ctatgcggca tcagagcaga ttgtactgag agtgcacca    3899
```